United States Patent
Yamazaki et al.

(10) Patent No.: US 11,667,605 B2
(45) Date of Patent: Jun. 6, 2023

(54) RESIST COMPOSITION, METHOD OF FORMING RESIST PATTERN, COMPOUND, ACID GENERATOR, AND METHOD OF PRODUCING COMPOUND

(71) Applicant: TOKYO OHKA KOGYO CO., LTD., Kawasaki (JP)

(72) Inventors: Hiroto Yamazaki, Kawasaki (JP); Masatoshi Arai, Kawasaki (JP); Yoshitaka Komuro, Kawasaki (JP)

(73) Assignee: TOKYO OHKA KOGYO CO., LTD., Kawasaki (JP)

( * ) Notice: Subject to any disclaimer, the term of this patent is extended or adjusted under 35 U.S.C. 154(b) by 0 days.

(21) Appl. No.: 17/444,446

(22) Filed: Aug. 4, 2021

(65) Prior Publication Data

US 2021/0389668 A1 Dec. 16, 2021

Related U.S. Application Data

(62) Division of application No. 16/420,956, filed on May 23, 2019, now Pat. No. 11,281,099.

(30) Foreign Application Priority Data

May 28, 2018 (JP) .............................. JP2018-101876

(51) Int. Cl.
| | |
|---|---|
| C07C 381/12 | (2006.01) |
| G03F 7/004 | (2006.01) |
| G03F 7/039 | (2006.01) |
| C07C 309/12 | (2006.01) |
| C07C 303/22 | (2006.01) |
| C07D 339/08 | (2006.01) |
| C07D 333/54 | (2006.01) |
| C07D 327/04 | (2006.01) |
| G03F 7/038 | (2006.01) |
| G03F 7/32 | (2006.01) |
| G03F 7/16 | (2006.01) |
| G03F 7/20 | (2006.01) |
| G03F 7/38 | (2006.01) |

(52) U.S. Cl.
CPC .......... *C07C 381/12* (2013.01); *C07C 303/22* (2013.01); *C07C 309/12* (2013.01); *C07D 327/04* (2013.01); *C07D 333/54* (2013.01); *C07D 339/08* (2013.01); *G03F 7/0045* (2013.01); *G03F 7/0382* (2013.01); *G03F 7/0392* (2013.01); *C07C 2603/74* (2017.05); *G03F 7/16* (2013.01); *G03F 7/162* (2013.01); *G03F 7/168* (2013.01); *G03F 7/2004* (2013.01); *G03F 7/2037* (2013.01); *G03F 7/322* (2013.01); *G03F 7/38* (2013.01)

(58) Field of Classification Search
CPC ............................ C07C 381/12; C07C 309/25
See application file for complete search history.

(56) References Cited

U.S. PATENT DOCUMENTS

| | | | |
|---|---|---|---|
| 8,012,672 B2 * | 9/2011 | Hayoz | ..................... B33Y 70/00 |
| | | | 568/18 |
| 9,023,584 B2 | 5/2015 | Maruyama et al. | |
| 9,244,347 B2 | 1/2016 | Komuro et al. | |
| 9,366,958 B2 | 6/2016 | Ohashi et al. | |
| 9,500,947 B2 | 11/2016 | LaBeaume et al. | |
| 9,557,642 B2 | 1/2017 | LaBeaume et al. | |
| 9,720,323 B2 | 8/2017 | Kotake et al. | |
| 9,766,541 B2 | 9/2017 | Yamazaki et al. | |
| 9,904,167 B2 | 2/2018 | Tsuchimura et al. | |
| 10,018,911 B2 | 7/2018 | Nakagawa et al. | |
| 10,101,658 B2 * | 10/2018 | Hirayama | ................ G03F 7/322 |
| 10,324,377 B2 * | 6/2019 | Hirayama | .............. G03F 7/0397 |
| 10,394,122 B2 | 8/2019 | Suzuki et al. | |
| 10,437,147 B2 | 10/2019 | Nagamine et al. | |
| 10,613,436 B2 | 4/2020 | Hatekeyama et al. | |
| 10,620,533 B2 | 4/2020 | Hatekeyama et al. | |
| 2005/0053861 A1 | 3/2005 | Yoneda et al. | |

(Continued)

FOREIGN PATENT DOCUMENTS

| | | | | |
|---|---|---|---|---|
| EP | | 972761 A1 * | 1/2000 | ........... C07C 381/12 |
| JP | A-2009-093137 | | 4/2009 | |

(Continued)

OTHER PUBLICATIONS

Office Action in U.S. Appl. No. 16/420,956 dated Aug. 18, 2021.
Office Action received in Japanese Patent Application No. 2019-097133, dated Jan. 17, 2023.

*Primary Examiner* — Amanda C. Walke

(74) *Attorney, Agent, or Firm* — Knobbe, Martens, Olson & Bear LLP

(57) ABSTRACT

A resist composition including a compound represented by formula (b1) in which $R^{b1}$ represents an aryl group which may have a substituent; $R^{b2}$ and $R^{b3}$ each independently represents an aryl group which may have a substituent or an alkyl group which may have a substituent; provided that at least one of the aryl group represented by $R^{b1}$ and the aryl group or the alkyl group represented by $R^{b2}$ or $R^{b3}$ has a substituent containing a halogen atom, and at least one of the aryl group represented by $R^{b1}$ and the aryl group or the alkyl group represented by $R^{b2}$ or $R^{b3}$ has a substituent containing a sulfonyl group; and $X^-$ represents a counteranion

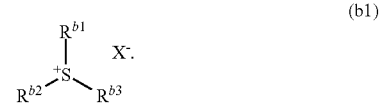

(b1)

18 Claims, No Drawings

(56) References Cited

U.S. PATENT DOCUMENTS

| | | |
|---|---|---|
| 2005/0064329 A1 | 3/2005 | Takahashi |
| 2010/0075256 A1* | 3/2010 | Joo .................... C07C 309/12 430/286.1 |
| 2010/0233617 A1 | 9/2010 | Wada |
| 2012/0237874 A1 | 9/2012 | Yamaguchi et al. |
| 2013/0078579 A1* | 3/2013 | Asano ................ C07D 333/78 430/325 |

FOREIGN PATENT DOCUMENTS

| | | | |
|---|---|---|---|
| JP | 4292981 B | 7/2009 | |
| JP | 4411042 B | 2/2010 | |
| JP | 2012141578 A * | 7/2012 | ............ G03F 7/004 |
| JP | A-2019-182813 | 10/2019 | |
| WO | WO-2008040648 A1 * | 4/2008 | ............ B33Y 70/00 |
| WO | WO-2009047151 A1 * | 4/2009 | ............ C07C 321/28 |
| WO | WO-2011048919 A1 * | 4/2011 | ............ C07C 309/06 |

* cited by examiner

RESIST COMPOSITION, METHOD OF FORMING RESIST PATTERN, COMPOUND, ACID GENERATOR, AND METHOD OF PRODUCING COMPOUND

This application is a divisional of U.S. application Ser. No. 16/420,956, filed May 23, 2019, which claims priority to Japanese Patent Application No. 2018-101876, filed May 28, 2018, the contents of which are incorporated herein by reference.

TECHNICAL FIELD

The present invention relates to a resist composition, a method of forming a resist pattern, a compound, an acid generator, and a method of producing a compound.

DESCRIPTION OF RELATED ART

In lithography techniques, for example, a resist film composed of a resist material is formed on a substrate, and the resist film is subjected to selective exposure, followed by development, thereby forming a resist pattern having a predetermined shape on the resist film. A resist material in which the exposed portions of the resist film become soluble in a developing solution is called a positive-type, and a resist material in which the exposed portions of the resist film become insoluble in a developing solution is called a negative-type.

In recent years, in the production of semiconductor elements and liquid crystal display elements, advances in lithography techniques have led to rapid progress in the field of pattern miniaturization. Typically, these miniaturization techniques involve shortening the wavelength (increasing the energy) of the exposure light source. Conventionally, ultraviolet radiation typified by g-line and i-line radiation has been used, but nowadays KrF excimer lasers and ArF excimer lasers are used in mass production. Furthermore, research is also being conducted into lithography techniques that use an exposure light source having a wavelength shorter (energy higher) than these excimer lasers, such as electron beam (EB), extreme ultraviolet radiation (EUV), and X ray.

Resist materials for use with these types of exposure light sources require lithography properties such as a high resolution capable of reproducing patterns of minute dimensions, and a high level of sensitivity to these types of exposure light sources.

As a resist material that satisfies these conditions, a chemically amplified composition is used, which includes a base material component that exhibits a changed solubility in a developing solution under the action of acid and an acid-generator component that generates acid upon exposure.

For example, in the case where the developing solution is an alkali developing solution (alkali developing process), a chemically amplified positive resist which contains, as a base component (base resin), a resin which exhibits increased solubility in an alkali developing solution under action of acid, and an acid generator is typically used. If a resist film formed using such a resist composition is selectively exposed at the time of forming a resist pattern, in exposed areas, acid is generated from the acid generator component, and the polarity of the base resin increases by the action of the generated acid, thereby making the exposed areas of the resist film soluble in the alkali developing solution. Thus, by conducting alkali developing, the unexposed portions of the resist film remain to form a positive resist pattern.

On the other hand, when such a base resin is applied to a solvent developing process using a developing solution containing an organic solvent (organic developing solution), the solubility of the exposed portions in an organic developing solution is decreased. As a result, the unexposed portions of the resist film are dissolved and removed by the organic developing solution, and a negative resist pattern in which the exposed portions of the resist film are remaining is formed. Such a solvent developing process for forming a negative-tone resist composition is sometimes referred to as "negative-tone developing process".

In general, the base resin used for a chemically amplified resist composition contains a plurality of structural units for improving lithography properties and the like.

For example, in the case of a resin composition which exhibits increased solubility in an alkali developing solution by the action of acid, a structural unit containing an acid decomposable group which is decomposed by the action of acid generated from an acid generator component and exhibits increased polarity. Further, a structural unit containing a lactone-containing cyclic group or a structural unit containing a polar group such as a hydroxy group is used in combination.

Further, in the formation of a resist pattern, the behavior of acid generated from the acid generator component upon exposure is one of the factors which has large influence on the lithography properties.

As the acid generator used in a chemically amplified resist composition, various kinds have been proposed. For example, onium salt acid generators such as iodonium salts and sulfonium salts; oxime sulfonate acid generators; diazomethane acid generators; nitrobenzylsulfonate acid generators; iminosulfonate acid generators; and disulfone acid generators are known.

As onium salt acid generators, those which have an onium ion such as triphenylsulfonium in the cation moiety are mainly used. Generally, as the anion moiety for onium salt acid generators, an alkylsulfonate ion or a fluorinated alkylsulfonate ion in which part or all of the hydrogen atoms within the aforementioned alkylsulfonate ion has been substituted with fluorine atoms is typically used.

As the lithography technique further progresses and the miniaturization of the resist pattern progresses more and more, for example, a target of the lithography performed by electron beams and EUV is to form fine resist patterns of several tens of nanometers. As the size of the resist pattern becomes smaller, the resist composition is required to have a high sensitivity to the exposure dose, and good lithography properties such as reduced roughness.

Patent Literature 1 describes using an onium salt acid generator having a sulfonium cation with a sulfonyl group introduced in order to enhance the sensitivity of the resist.

Further, Patent Literature 2 describes using an onium salt acid generator having a sulfonium cation with a fluorine atom introduced in order to enhance the sensitivity of the resist.

DOCUMENTS OF RELATED ART

Patent Literature

[Patent Literature 1] Japanese Patent No. 4292981
[Patent Literature 2] Japanese Patent No. 4411042

SUMMARY OF THE INVENTION

However, an onium salt acid generator having a sulfonium cation with a sulfonyl group or a fluorine atom introduced had concerns in that lithography properties such as roughness may be adversely affected.

The present invention takes the above circumstances into consideration, with an object of providing a novel compound useful as an acid generator for a resist composition, an acid generator using the compound, an intermediate compound useful as an intermediate of the compound, a resist composition containing the acid generator, and a method of forming a resist pattern using the resist composition.

For solving the above-mentioned problems, the present invention employs the following aspects.

A first aspect of the present invention is a resist composition which generates acid upon exposure and exhibits changed solubility in a developing solution under action of acid, the resist composition including a base component (A) which exhibits changed solubility in a developing solution under action of acid, and an acid generator (B1) containing a compound represented by general formula (b1) shown below.

[Chemical Formula 1.]

(b1)

In the formula, $R^{b1}$ represents an aryl group which may have a substituent; $R^{b2}$ and $R^{b3}$ each independently represents an aryl group which may have a substituent or an alkyl group which may have a substituent; $R^{b2}$ and $R^{b3}$ may be mutually bonded to form a ring with the sulfur atom; provided that at least one of the aryl group represented by $R^{b1}$ and the aryl group or the alkyl group represented by $R^{b2}$ or $R^{b3}$ has a substituent containing a halogen atom, and at least one of the aryl group represented by $R^{b1}$ and the aryl group or the alkyl group represented by $R^{b2}$ or $R^{b3}$ has a substituent containing a sulfonyl group; and $X^-$ represents a counteranion.

A second aspect of the present invention is a method of forming a resist pattern, including: using a resist composition according to the first aspect to form a resist film, exposing the resist film, and developing the exposed resist film to form a resist pattern.

A third aspect of the present invention is a compound represented by general formula (b1) shown below.

[Chemical Formula 2.]

(b1)

In the formula, $R^{b1}$ represents an aryl group which may have a substituent; $R^{b2}$ and $R^{b3}$ each independently represents an aryl group which may have a substituent or an alkyl group which may have a substituent;

$R^{b2}$ and $R^{b3}$ may be mutually bonded to form a ring with the sulfur atom; provided that at least one of the aryl group represented by $R^{b1}$ and the aryl group or the alkyl group represented by $R^{b2}$ or $R^{b3}$ has a substituent containing a halogen atom, and at least one of the aryl group represented by $R^{b1}$ and the aryl group or the alkyl group represented by $R^{b2}$ or $R^{b3}$ has a substituent containing a sulfonyl group; and $X^-$ represents a counteranion.

A fourth aspect of the present invention is an acid generator including a compound of the third aspect.

A fifth aspect of the present invention is a compound represented by general formula (bp-1) shown below.

[Chemical Formula 3.]

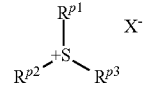
(bp-1)

In the formula, $R^{p1}$ represents an aryl group which may have a substituent; $R^{p2}$ and $R^{p3}$ each independently represents an aryl group which may have a substituent or an alkyl group which may have a substituent;

$R^{p2}$ and $R^{p3}$ may be mutually bonded to form a ring with the sulfur atom; provided that at least one of the aryl group represented by $R^{p1}$ and the aryl group or the alkyl group represented by $R^{p2}$ or $R^{p3}$ has a substituent containing a halogen atom, and at least one of the aryl group represented by $R^{p1}$ and the aryl group or the alkyl group represented by $R^{p2}$ or $R^{p3}$ has a group represented by the formula: $-SR^{p4}$ as a substituent; $R^{p4}$ represents an alkyl group; and $Xp^-$ represents a counteranion.

A sixth aspect of the present invention is a method of producing a compound, the method including: oxidizing a compound represented by general formula (bp-1) shown below to obtain a compound represented by general formula (b1-1) shown below.

[Chemical Formula 4.]

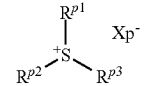
(bp-1)

In the formula, $R^{p1}$ represents an aryl group which may have a substituent; $R^{p2}$ and $R^{p3}$ each independently represents an aryl group which may have a substituent or an alkyl group which may have a substituent;

$R^{p2}$ and $R^{p3}$ may be mutually bonded to form a ring with the sulfur atom; provided that at least one of the aryl group represented by $R^{p1}$ and the aryl group or the alkyl group represented by $R^{p2}$ or $R^{p3}$ has a substituent containing a halogen atom, and at least one of the aryl group represented by $R^{p1}$ and the aryl group or the alkyl group represented by $R^{p2}$ or $R^{p3}$ has a group represented by the formula: $-SO_2-R^{p4}$ as a substituent; $R^{p4}$ represents an alkyl group; and $Xp^-$ represents a counteranion.

[Chemical Formula 5.]

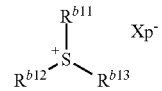
(b1-1)

In the formula, $R^{b11}$ represents an aryl group which may have a substituent; $R^{b12}$ and $R^{b13}$ each independently represents an aryl group which may have a substituent or an alkyl group which may have a substituent; $R^{b12}$ and $R^{b13}$ may be mutually bonded to form a ring with the sulfur atom; provided that at least one of the aryl group represented by $R^{b1}$ and the aryl group or the alkyl group represented by $R^{b12}$ or $R^{b13}$ has a substituent containing a halogen atom, and at least one of the aryl group represented by $R^{b11}$ and the aryl group or the alkyl group represented by $R^{b12}$ or $R^{b13}$ has a group represented by the formula: —$SR^{p4}$ as a substituent; $R^{p4}$ represents an alkyl group; and $Xp^-$ represents a counteranion.

Another aspect of the present invention is a resist composition which generates acid upon exposure and exhibits changed solubility in a developing solution under action of acid, the resist composition including a base component (A) which exhibits changed solubility in a developing solution under action of acid, and at least one compound (D11) selected from the group consisting of a compound represented by general formula (d1-1) shown below, a compound represented by general formula (d1-2) shown below and a compound represented by general formula (d1-3) shown below.

[Chemical Formula 6.]

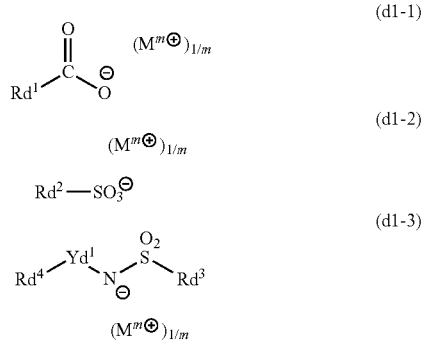

In the formulae, $Rd^1$ to $Rd^4$ represent a cyclic group which may have a substituent, a chain-like alkyl group which may have a substituent or a chain-like alkenyl group which may have a substituent, provided that, the carbon atom adjacent to the sulfur atom within the $Rd^2$ in the formula (d1-2) has no fluorine atom bonded thereto; $Yd^1$ represents a single bond or a divalent linking group; m is an integer of 1 or more; and each $M^{m+}$ independently represents the sulfonium cation in the aforementioned formula (b1).

According to the present invention, there is provided a novel compound useful as an acid generator for a resist composition, an acid generator using the compound, an intermediate compound useful as an intermediate of the compound, a resist composition containing the acid generator, and a method of forming a resist pattern using the resist composition.

According to the resist composition of the present invention, sensitivity can be enhanced in the formation of a resist pattern, and it becomes possible to form a resist pattern exhibiting good lithography properties (reduced roughness, and the like).

DETAILED DESCRIPTION OF THE INVENTION

In the present description and claims, the term "aliphatic" is a relative concept used in relation to the term "aromatic", and defines a group or compound that has no aromaticity.

The term "alkyl group" includes linear, branched or cyclic, monovalent saturated hydrocarbon, unless otherwise specified. The same applies for the alkyl group within an alkoxy group.

The term "alkylene group" includes linear, branched or cyclic, divalent saturated hydrocarbon, unless otherwise specified.

A "halogenated alkyl group" is a group in which part or all of the hydrogen atoms of an alkyl group is substituted with a halogen atom. Examples of the halogen atom include a fluorine atom, a chlorine atom, a bromine atom and an iodine atom.

A "fluorinated alkyl group" or a "fluorinated alkylene group" is a group in which part or all of the hydrogen atoms of an alkyl group or an alkylene group have been substituted with a fluorine atom.

The term "structural unit" refers to a monomer unit that contributes to the formation of a polymeric compound (resin, polymer, copolymer).

The case of describing "may have a substituent" includes both of the case where the hydrogen atom (—H) is substituted with a monovalent group and the case where the methylene group (—$CH_2$—) is substituted with a divalent group.

The term "exposure" is used as a general concept that includes irradiation with any form of radiation.

A "structural unit derived from an acrylate ester" refers to a structural unit that is formed by the cleavage of the ethylenic double bond of an acrylate ester.

An "acrylate ester" refers to a compound in which the terminal hydrogen atom of the carboxy group of acrylic acid ($CH_2$=CH—COOH) has been substituted with an organic group.

The acrylate ester may have the hydrogen atom bonded to the carbon atom on the α-position substituted with a substituent. The substituent ($R^{\alpha 0}$) that substitutes the hydrogen atom bonded to the carbon atom on the α-position is an atom other than hydrogen or a group, and examples thereof include an alkyl group of 1 to 5 carbon atoms and a halogenated alkyl group of 1 to 5 carbon atoms. Further, an acrylate ester having the hydrogen atom bonded to the carbon atom on the α-position substituted with a substituent ($R^{\alpha 0}$) in which the substituent has been substituted with a substituent containing an ester bond (e.g., an itaconic acid diester), or an acrylic acid having the hydrogen atom bonded to the carbon atom on the α-position substituted with a substituent ($R^{\alpha 0}$) in which the substituent has been substituted with a hydroxyalkylgroup or a group in which the hydroxy group within a hydroxyalkyl group has been modified (e.g., α-hydroxyalkyl acrylate ester) can be mentioned as an acrylate ester having the hydrogen atom bonded to the carbon atom on the α-position substituted with a substituent. A carbon atom on the α-position of an acrylate ester refers to the carbon atom bonded to the carbonyl group, unless specified otherwise.

Hereafter, an acrylate ester having the hydrogen atom bonded to the carbon atom on the α-position substituted with a substituent is sometimes referred to as "α-substituted acrylate ester". Further, acrylate esters and α-substituted acrylate esters are collectively referred to as "(α-substituted) acrylate ester".

A "structural unit derived from acrylamide" refers to a structural unit that is formed by the cleavage of the ethylenic double bond of acrylamide.

The acrylamide may have the hydrogen atom bonded to the carbon atom on the α-position substituted with a substituent, and may have either or both terminal hydrogen atoms on the amino group of acrylamide substituted with a substituent. A carbon atom on the α-position of an acrylamide refers to the carbon atom bonded to the carbonyl group, unless specified otherwise.

As the substituent which substitutes the hydrogen atom on the α-position of acrylamide, the same substituents as those described above for the substituent ($R^{\alpha 0}$) on the α-position of the aforementioned α-position of the aforementioned α-substituted acrylate ester can be mentioned.

A "structural unit derived from hydroxystyrene" refers to a structural unit that is formed by the cleavage of the ethylenic double bond of hydroxystyrene. A "structural unit derived from a hydroxystyrene derivative" refers to a structural unit that is formed by the cleavage of the ethylenic double bond of a hydroxystyrene derivative.

The term "hydroxystyrene derivative" includes compounds in which the hydrogen atom at the α-position of hydroxystyrene has been substituted with another substituent such as an alkyl group or a halogenated alkyl group; and derivatives thereof. Examples of the derivatives thereof include hydroxystyrene in which the hydrogen atom of the hydroxy group has been substituted with an organic group and may have the hydrogen atom on the α-position substituted with a substituent; and hydroxystyrene which has a substituent other than a hydroxy group bonded to the benzene ring and may have the hydrogen atom on the α-position substituted with a substituent. Here, the α-position (carbon atom on the α-position) refers to the carbon atom having the benzene ring bonded thereto, unless specified otherwise.

As the substituent which substitutes the hydrogen atom on the α-position of hydroxystyrene, the same substituents as those described above for the substituent on the α-position of the aforementioned α-substituted acrylate ester can be mentioned.

A "structural unit derived from vinylbenzoic acid or a vinylbenzoic acid derivative" refers to a structural unit that is formed by the cleavage of the ethylenic double bond of vinylbenzoic acid or a vinylbenzoic acid derivative.

The term "vinylbenzoic acid derivative" includes compounds in which the hydrogen atom at the α-position of vinylbenzoic acid has been substituted with another substituent such as an alkyl group or a halogenated alkyl group; and derivatives thereof. Examples of the derivatives thereof include benzoic acid in which the hydrogen atom of the carboxy group has been substituted with an organic group and may have the hydrogen atom on the α-position substituted with a substituent; and benzoic acid which has a substituent other than a hydroxy group and a carboxy group bonded to the benzene ring and may have the hydrogen atom on the α-position substituted with a substituent. Here, the α-position (carbon atom on the α-position) refers to the carbon atom having the benzene ring bonded thereto, unless specified otherwise.

The term "styrene derivative" includes compounds in which the hydrogen atom at the α-position of styrene has been substituted with another substituent such as an alkyl group or a halogenated alkyl group; and derivatives thereof. Examples of the derivatives thereof include hydroxystyrene which has a substituent other than a hydroxy group bonded to the benzene ring and may have the hydrogen atom on the α-position substituted with a substituent. Here, the α-position (carbon atom on the α-position) refers to the carbon atom having the benzene ring bonded thereto, unless specified otherwise.

A "structural unit derived from styrene" or "structural unit derived from a styrene derivative" refers to a structural unit that is formed by the cleavage of the ethylenic double bond of styrene or a styrene derivative.

As the alkyl group as a substituent on the α-position, a linear or branched alkyl group is preferable, and specific examples include alkyl groups of 1 to 5 carbon atoms, such as a methyl group, an ethyl group, a propyl group, an isopropyl group, an n-butyl group, an isobutyl group, a tert-butyl group, a pentyl group, an isopentyl group and a neopentyl group.

Specific examples of the halogenated alkyl group as the substituent on the α-position include groups in which part or all of the hydrogen atoms of the aforementioned "alkyl group as the substituent on the α-position" are substituted with halogen atoms. Examples of the halogen atom include a fluorine atom, a chlorine atom, a bromine atom and an iodine atom, and a fluorine atom is particularly desirable.

Specific examples of the hydroxyalkyl group as the substituent on the α-position include groups in which part or all of the hydrogen atoms of the aforementioned "alkyl group as the substituent on the α-position" are substituted with a hydroxy group. The number of hydroxy groups within the hydroxyalkyl group is preferably 1 to 5, and most preferably 1.

In the present specification and claims, some structures represented by chemical formulae may have an asymmetric carbon, such that an enantiomer or a diastereomer may be present. In such a case, the one formula represents all isomers. The isomers may be used individually, or in the form of a mixture.

(Resist Composition)

The resist composition according to a first aspect of the present invention is a resist composition which generates acid upon exposure and exhibits changed solubility in a developing solution under action of acid. In one embodiment, the resist composition includes a base component (A) (hereafter, sometimes referred to as "component (A)") which exhibits changed solubility in a developing solution under action of acid, and an acid-generator component (B) (hereafter, sometimes referred to as "component (B)") which generates acid upon exposure.

When a resist film is formed using the resist composition according to the present embodiment and the formed resist film is subjected to a selective exposure, acid is generated at exposed portions, and the generated acid acts on the component (A) to change the solubility of the component (A) in a developing solution, whereas the solubility of the component (A) in a developing solution is not changed at unexposed portions, thereby generating difference in solubility in a developing solution between exposed portions and unexposed portions. Therefore, by subjecting the resist film to development, the exposed portions of the resist film are dissolved and removed to form a positive-tone resist pattern in the case of a positive resist, whereas the unexposed portions of the resist film are dissolved and removed to form a negative-tone resist pattern in the case of a negative resist.

In the present specification, a resist composition which forms a positive resist pattern by dissolving and removing the exposed portions of the resist film is called a positive resist composition, and a resist composition which forms a negative resist pattern by dissolving and removing the unexposed portions of the resist film is called a negative resist composition.

The resist composition of the present embodiment may be either a positive resist composition or a negative resist composition. Further, in the present embodiment, the resist composition may be applied to an alkali developing process using an alkali developing solution in the developing treatment, or a solvent developing process using a developing solution containing an organic solvent (organic developing solution) in the developing treatment, and preferably a solvent developing process.

The resist composition of the present embodiment has a function of generating acid upon exposure, and the component (A) may generate acid upon exposure, in addition to the component (B).

In the case where the component (A) generates acid upon exposure, the component (A) is a "base component which generates acid upon exposure and exhibits changed solubility in a developing solution under action of acid".

In the case where the component (A) is a base component which generates acid upon exposure and exhibits changed solubility in a developing solution under action of acid, the component (A1) described later is preferably a polymeric compound which generates acid upon exposure and exhibits changed solubility in a developing solution under action of acid. As the polymeric compound, a resin having a structural unit which generates acid upon exposure may be mentioned. As the structural unit which generates acid upon exposure, any conventionally known structural unit may be used.

<Component (A)>

In the resist composition of the present embodiment, the component (A) is a base component which exhibits changed solubility in a developing solution under action of acid.

In the present invention, the term "base component" refers to an organic compound capable of forming a film, and is preferably an organic compound having a molecular weight of 500 or more. When the organic compound has a molecular weight of 500 or more, the film-forming ability is improved, and a resist pattern of nano level can be easily formed.

The organic compound used as the base component is broadly classified into non-polymers and polymers.

In general, as a non-polymer, any of those which have a molecular weight in the range of 500 to less than 4,000 is used. Hereafter, a "low molecular weight compound" refers to a non-polymer having a molecular weight in the range of 500 to less than 4,000.

As a polymer, any of those which have a molecular weight of 1,000 or more is generally used. Hereafter, a "resin" or a "polymer" refers to a polymer having a molecular weight of 1,000 or more.

As the molecular weight of the polymer, the weight average molecular weight in terms of the polystyrene equivalent value determined by gel permeation chromatography (GPC) is used.

In the case where the resist composition of the present embodiment is a "negative resist composition for alkali developing process" which forms a negative resist pattern in an alkali developing process, or a "positive resist composition for solvent developing process", as the component (A), a base component (A-2) which is soluble in an alkali developing solution (hereafter, referred to as "component (A-2)") may be preferably used, and a cross-linking agent is blended. In such a resist composition, for example, when acid is generated from the component (B) upon exposure, the action of the acid causes cross-linking between the component (A-2) and the cross-linking component. As a result, the solubility of the resist composition in an alkali developing solution is decreased (the solubility of the resist composition in an organic developing solution is increased).

Therefore, in the formation of a resist pattern, by conducting selective exposure of a resist film formed by applying the resist composition to a substrate, the exposed portions of the resist film become insoluble in an alkali developing solution (soluble in an organic developing solution), whereas the unexposed portions of the resist film remain soluble in an alkali developing solution (insoluble in an organic developing solution), and hence, a negative resist pattern is formed by conducting development using an alkali developing solution. Alternatively, in such a case, by developing using an organic developing solution, a positive resist pattern is formed.

As the component (A-2), a resin that is soluble in an alkali developing solution (hereafter, referred to as "alkali-soluble resin") is preferably used.

Examples of the alkali soluble resin include a resin having a structural unit derived from at least one of α-(hydroxyalkyl)acrylic acid and an alkyl ester of α-(hydroxyalkyl) acrylic acid (preferably an alkyl ester having 1 to 5 carbon atoms), as disclosed in Japanese Unexamined Patent Application, First Publication No. 2000-206694; an acrylic resin which has a sulfonamide group and may have the hydrogen atom bonded to the carbon atom on the α-position substituted with a substituent or polycycloolefin resin having a sulfoneamide group, as disclosed in U.S. Pat. No. 6,949,325; an acrylic resin which may have the hydrogen atom bonded to the carbon atom on the α-position substituted with a substituent and having a fluorinated alcohol, as disclosed in U.S. Pat. No. 6,949,325, Japanese Unexamined Patent Application, First Publication No. 2005-336452 or Japanese Unexamined Patent Application, First Publication No. 2006-317803; and a polycyclolefin resin having a fluorinated alcohol, as disclosed in Japanese Unexamined Patent Application, First Publication No. 2006-259582. These resins are preferable in that a resist pattern can be formed with minimal swelling.

Here, the term "α-(hydroxyalkyl)acrylic acid" refers to one or both of acrylic acid in which a hydrogen atom is bonded to the carbon atom on the α-position having the carboxyl group bonded thereto, and α-hydroxyalkylacrylic acid in which a hydroxyalkyl group (preferably a hydroxyalkyl group of 1 to 5 carbon atoms) is bonded to the carbon atom on the α-position.

As the cross-linking agent, typically, an amino-based cross-linking agent such as a glycoluril having a methylol group or alkoxymethyl group, or a melamine-based cross-linking agent is preferable, as it enables formation of a resist pattern with minimal swelling. The amount of the cross-linker added is preferably within a range from 1 to 50 parts by weight, relative to 100 parts by weight of the alkali-soluble resin.

In the case where the resist composition of the present embodiment is a "positive resist composition for alkali developing process" which forms a positive resist pattern in an alkali developing process, or a "negative resist composition for solvent developing process", as the component (A), a base component (A-1) which exhibits increased polarity by the action of acid (hereafter, referred to as "component (A-1)") may be preferably used. By using the component (A-1), since the polarity of the base component changes prior to and after exposure, an excellent development contrast can be obtained not only in an alkali developing process, but also in a solvent developing process.

More specifically, in the case of applying an alkali developing process, the component (A-1) is substantially insoluble in an alkali developing solution prior to exposure, but when acid is generated from the component (B) upon exposure, the action of this acid causes an increase in the polarity of the base component, thereby increasing the solubility of the component (A-1) in an alkali developing solution. Therefore, in the formation of a resist pattern, by conducting selective exposure of a resist film formed by applying the resist composition to a substrate, the exposed portions of the resist film change from an insoluble state to a soluble state in an alkali developing solution, whereas the unexposed portions of the resist film remain insoluble in an alkali developing solution, and hence, a positive resist pattern is formed by alkali developing.

On the other hand, in the case of a solvent developing process, the component (A-1) exhibits high solubility in an organic developing solution prior to exposure, and when acid is generated from the component (B) upon exposure, the polarity of the component (A-1) is increased by the action of the generated acid, thereby decreasing the solubility of the component (A-1) in an organic developing solution. Therefore, in the formation of a resist pattern, by conducting selective exposure of a resist film formed by applying the resist composition to a substrate, the exposed portions of the resist film changes from an soluble state to an insoluble state in an organic developing solution, whereas the unexposed portions of the resist film remain soluble in an organic developing solution. As a result, by conducting development using an organic developing solution, a contrast can be made between the exposed portions and unexposed portions, thereby forming a negative resist pattern.

In the resist composition of the present embodiment, as the component (A), one kind of compound may be used, or two or more kinds of compounds may be used in combination.

In the resist composition of the present embodiment, the component (A) is preferably a component (A-1). That is, the resist composition of the present embodiment is preferably a resist composition which forms a positive pattern in an alkali developing process (i.e, a positive resist compound for alkali developing process) or a resist composition which forms a negative pattern in a solvent developing process (i.e., a negative type resist composition for solvent developing process). As the component (A), at least one of a polymeric compound and a low molecular weight compound may be used.

In the case where the component (A) is a component (A-1), the component (A-1) preferably contains a resin component (A1) (hereafter, referred to as "component (A1) ").

Component (A1)

The component (A1) is a resin component preferably containing a polymeric compound having a structural unit (a1) containing an acid decomposable group that exhibits increased polarity by the action of acid.

The component (A1) preferably has, in addition to the structural unit (a1), a structural unit (a10) containing a hydroxystyrene skeleton.

Further, the component (A1) may have, in addition to the structural unit (a1), a structural unit (a2) containing a lactone-containing cyclic group, an —$SO_2$— containing cyclic group or a carbonate-containing cyclic group.

Further, the component (A1) may have, in addition to the structural unit (a1), a structural unit (a3) containing a polar group-containing aliphatic hydrocarbon group (provided that the structural units that fall under the definition of structural units (a1) and (a2) are excluded).

The component (A1) may further include a structural unit other than the structural units (a1), (a2), (a3) and (a10).

<<Structural Unit (a1)>>

The structural unit (a1) is a structural unit containing an acid decomposable group that exhibits increased polarity by the action of acid.

The term "acid decomposable group" refers to a group in which at least a part of the bond within the structure thereof is cleaved by the action of an acid.

Examples of acid decomposable groups which exhibit increased polarity by the action of an acid include groups which are decomposed by the action of an acid to form a polar group.

Examples of the polar group include a carboxy group, a hydroxy group, an amino group and a sulfo group (—$SO_3H$). Among these, a polar group containing —OH in the structure thereof (hereafter, referred to as "OH-containing polar group") is preferable, a carboxy group or a hydroxy group is more preferable, and a carboxy group is particularly desirable.

More specifically, as an example of an acid decomposable group, a group in which the aforementioned polar group has been protected with an acid dissociable group (such as a group in which the hydrogen atom of the OH-containing polar group has been protected with an acid dissociable group) can be given.

The "acid dissociable group" refers to both (i) a group in which the bond between the acid dissociable group and the adjacent atom is cleaved by the action of acid; and (ii) a group in which one of the bonds is cleaved by the action of acid, and then a decarboxylation reaction occurs, thereby cleaving the bond between the acid dissociable group and the adjacent atom.

It is necessary that the acid dissociable group that constitutes the acid decomposable group is a group which exhibits a lower polarity than the polar group generated by the dissociation of the acid dissociable group. Thus, when the acid dissociable group is dissociated by the action of acid, a polar group exhibiting a higher polarity than that of the acid dissociable group is generated, thereby increasing the polarity. As a result, the polarity of the entire component (A1) is increased. By the increase in the polarity, the solubility in an alkali developing solution changes, and the solubility in an alkali developing solution is relatively increased, whereas the solubility in an organic developing solution is relatively decreased.

Examples of the acid dissociable group include groups which have been proposed as acid dissociable groups for the base resin of a conventional chemically amplified resist composition.

Specific examples of acid dissociable groups for the base resin of a conventional chemically amplified resist composition include "acetal-type acid dissociable group", "tertiary alkyl ester-type acid dissociable group" and "tertiary alkyloxycarbonyl acid dissociable group" described below.

Acetal-Type Acid Dissociable Group

Examples of the acid dissociable group for protecting the carboxy group or hydroxy group as a polar group include the acid dissociable group represented by general formula (a1-r-1) shown below (hereafter, referred to as "acetal-type acid dissociable group").

[Chemical Formula 7.]

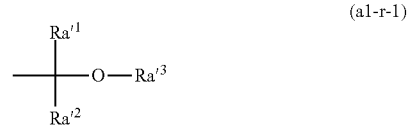

(a1-r-1)

In the formula, $Ra^{t1}$ and $Ra^{t2}$ each independently represents a hydrogen atom or an alkyl group; $Ra^{t3}$ represents a hydrocarbon group, provided that $Ra^{t3}$ may be bonded to $Ra^{t1}$ or $Ra^{t2}$ to form a ring.

In the formula (a1-r-1), it is preferable that at least one of $Ra^{t1}$ and $Ra^{t2}$ represents a hydrogen atom, and it is more preferable that both of $Ra^{t1}$ and $Ra^{t2}$ represent a hydrogen atom.

In the case where $Ra^{t1}$ or $Ra^{t2}$ is an alkyl group, as the alkyl group, the same alkyl groups as those described above the for the substituent which may be bonded to the carbon atom on the α-position of the aforementioned α-substituted acrylate ester can be mentioned, and an alkyl group of 1 to 5 carbon atoms is preferable. Specific examples include linear or branched alkyl groups. Specific examples of the alkyl group include a methyl group, an ethyl group, a propyl group, an isopropyl group, an n-butyl group, an isobutyl group, a tert-butyl group, a pentyl group, an isopentyl group and a neopentyl group. Of these, a methyl group or an ethyl group is preferable, and a methyl group is particularly preferable.

In formula (a1-r-1), examples of the hydrocarbon group for $Ra^{t3}$ include a linear or branched alkyl group and a cyclic hydrocarbon group.

The linear alkyl group preferably has 1 to 5 carbon atoms, more preferably 1 to 4 carbon atoms, and still more preferably 1 or 2 carbon atoms. Specific examples include a methyl group, an ethyl group, an n-propyl group, an n-butyl group and an n-pentyl group. Among these, a methyl group, an ethyl group or an n-butyl group is preferable, and a methyl group or an ethyl group is more preferable.

The branched alkyl group preferably has 3 to 10 carbon atoms, and more preferably 3 to 5 carbon atoms. Specific examples include an isopropyl group, an isobutyl group, a tert-butyl group, an isopentyl group, a neopentyl group a 1,1-diethylpropyl group and a 2,2-dimethylbutyl group. Among these, an isopropyl group is preferable.

In the case where $Ra^{t3}$ represents a cyclic hydrocarbon group, the cyclic hydrocarbon group may be an aliphatic hydrocarbon group or an aromatic hydrocarbon group, and may be polycyclic or monocyclic.

As the monocyclic aliphatic hydrocarbon group, a group in which 1 hydrogen atom has been removed from a monocycloalkane is preferable. The monocycloalkane preferably has 3 to 6 carbon atoms, and specific examples thereof include cyclopentane and cyclohexane.

As the polycyclic aliphatic hydrocarbon group, a group in which 1 hydrogen atom has been removed from a polycycloalkane is preferable, and the polycyclic group preferably has 7 to 12 carbon atoms. Examples of the polycycloalkane include adamantane, norbornane, isobornane, tricyclodecane and tetracyclododecane.

When the monovalent hydrocarbon group for $Ra^{t3}$ is an aromatic hydrocarbon group, the aromatic hydrocarbon group is a hydrocarbon group having at least one aromatic ring.

The aromatic ring is not particularly limited, as long as it is a cyclic conjugated compound having (4n+2)π electrons, and may be either monocyclic or polycyclic. The aromatic ring preferably has 5 to 30 carbon atoms, more preferably 5 to 20 carbon atoms, and still more preferably 6 to 15 carbon atoms, and most preferably 6 to 12 carbon atoms.

Examples of the aromatic ring include aromatic hydrocarbon rings, such as benzene, naphthalene, anthracene and phenanthrene; and aromatic hetero rings in which part of the carbon atoms constituting the aforementioned aromatic hydrocarbon rings has been substituted with a hetero atom. Examples of the hetero atom within the aromatic hetero rings include an oxygen atom, a sulfur atom and a nitrogen atom. Specific examples of the aromatic hetero ring include a pyridine ring and a thiophene ring.

Specific examples of the aromatic hydrocarbon group for $Ra^{t3}$ include a group in which one hydrogen atom has been removed from the aforementioned aromatic hydrocarbon ring or aromatic hetero ring (aryl group or heteroaryl group); a group in which one hydrogen atom has been removed from an aromatic compound having two or more aromatic rings (biphenyl, fluorene or the like); and a group in which one hydrogen atom of the aforementioned aromatic hydrocarbon ring or aromatic hetero ring has been substituted with an alkylene group (an arylalkyl group such as a benzyl group, a phenethyl group, a 1-naphthylmethyl group, a 2-naphthylmethyl group, a 1-naphthylethyl group, or a 2-naphthylethyl group). The alkylene group bonded to the aforementioned aromatic hydrocarbon ring or the aromatic hetero ring preferably has 1 to 4 carbon atoms, more preferably 1 or 2 carbon atoms, and most preferably 1 carbon atom.

The cyclic hydrocarbon group for $Ra^{t3}$ may have a substituent. Examples of the substituent include $—R^{P1}$, $—R^{P2}—O—R^{P1}$, $—R^{P2}—CO—R^{P1}$, $—R^{P2}—CO—OR^{P1}$, $—R^{P2}—O—CO—R^{P1}$, $—R^{P2}—OH$, $—R^{P2}—CN$ or $—R^{P2}—COOH$ (hereafter, these substituents are sometimes collectively referred to as "$Ra^{05}$").

Here, $R^{P1}$ is a monovalent chain saturated hydrocarbon group having 1 to 10 carbon atoms, a monovalent aliphatic cyclic saturated hydrocarbon group having 3 to 20 carbon atoms, or a monovalent aromatic hydrocarbon group having 6 to 30 carbon atoms. Further, $R^{P2}$ is a single bond, a divalent chain saturated hydrocarbon group having 1 to 10 carbon atoms, a divalent aliphatic cyclic saturated hydrocarbon group having 3 to 20 carbon atoms, or a divalent aromatic hydrocarbon group having 6 to 30 carbon atoms.

Here, a portion or all of the hydrogen atoms having the chain saturated hydrocarbon group, the aliphatic cyclic saturated hydrocarbon group, and the aromatic hydrocarbon group for $R^{P1}$ and $R^{P2}$ may be substituted with a fluorine atom. The aliphatic cyclic hydrocarbon group may have 1 or more substituents of 1 kind, or 1 or more substituents of a plurality of kinds.

Examples of the monovalent chain saturated hydrocarbon group having 1 to 10 carbon atoms include a methyl group, an ethyl group, a propyl group, a butyl group, a pentyl group, a hexyl group, a heptyl group, an octyl group, and a decyl group.

Examples of the monovalent aliphatic cyclic saturated hydrocarbon group having 3 to 20 carbon atoms include a monocyclic aliphatic saturated hydrocarbon group such as a cyclopropyl group, a cyclobutyl group, a cyclopentyl group, a cyclohexyl group, a cycloheptyl group, a cyclooctyl group, a cyclodecyl group, and a cyclododecyl group; and a polycyclic aliphatic saturated hydrocarbon group such as a bicyclo[2.2.2]octanyl group, a tricyclo[5.2.1.02,6]decanyl group, a tricyclo[3.3.1.13,7]decanyl group, a tetracyclo[6.2.1.13,6.02,7]dodecanyl group, and an adamantyl group.

Examples of the monovalent aromatic hydrocarbon group having 6 to 30 carbon atoms include a group obtained by removing one hydrogen atom from the aromatic hydrocarbon ring such as benzene, biphenyl, fluorene, naphthalene, anthracene, and phenanthrene.

In the case where $Ra^{t3}$ is bonded to $Ra^{t1}$ or $Ra^{t2}$ to form a ring, the cyclic group is preferably a 4 to 7-membered ring, and more preferably a 4 to 6-membered ring. Specific examples of the cyclic group include tetrahydropyranyl group and tetrahydrofuranyl group.

Tertiary Alkyl Ester-Type Acid Dissociable Group

Examples of the acid dissociable group for protecting the carboxy group as a polar group include the acid dissociable group represented by general formula (a1-r-2) shown below.

Among the acid dissociable groups represented by general formula (a1-r-2), for convenience, a group which is constituted of alkyl groups is referred to as "tertiary ester-type acid dissociable group".

[Chemical Formula 8.]

(a1-r-2)

In the formula, $Ra'^4$ to $Ra'^6$ each independently represents a hydrocarbon group, provided that $Ra'^5$ and $Ra'^6$ may be mutually bonded to form a ring.

Examples of the hydrocarbon group for $Ra'^4$ include a linear or branched alkyl group, a chain or cyclic alkenyl group, and a cyclic hydrocarbon group.

The linear or branched alkyl group and the cyclic hydrocarbon group (monocyclic aliphatic hydrocarbon group, polycyclic aliphatic hydrocarbon group or aromatic hydrocarbon group) for $Ra'^4$ are the same as defined for $Ra'^3$.

The chain or cyclic alkenyl group for $Ra'^4$ is preferably an alkenyl group having 2 to 10 carbon atoms.

The hydrocarbon group for $Ra'^5$ and $Ra'^6$ is the same as defined for $Ra'^3$.

In the case where $Ra'^5$ and $Ra'^6$ are mutually bonded to form a ring, a group represented by general formula (a1-r2-1) shown below, a group represented by general formula (a1-r2-2) shown below, and a group represented by general formula (a1-r2-3) shown below may be given as preferable examples.

On the other hand, in the case where $Ra'^4$ to $Ra'^6$ are not mutually bonded and independently represent a hydrocarbon group, the group represented by general formula (a1-r2-4) shown below may be given as a preferable example.

[Chemical Formula 9.]

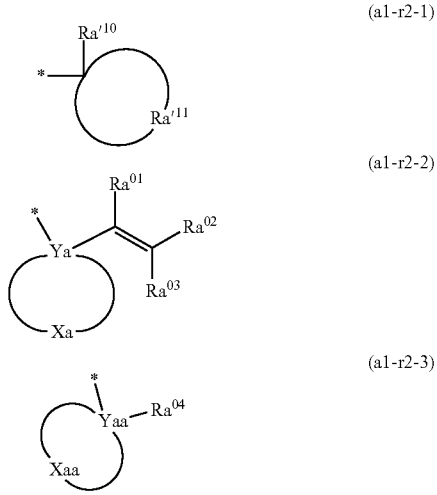

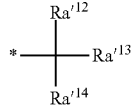

(a1-r2-4)

In formula (a1-r2-1), $Ra'^{10}$ represents an alkyl group of 1 to 10 carbon atoms, or a group represented by general formula (a1-r2-r1) shown below; $Ra'^{11}$ is a group which forms an aliphatic cyclic group together with a carbon atom having $Ra'^{10}$ bonded thereto. In formula (a1-r2-2), Ya represents a carbon atom; Xa represents a group which forms a cyclic hydrocarbon group together with Ya, provided that part or all of the hydrogen atoms of the cyclic hydrocarbon group may be substituted; $Ra^{01}$ to $Ra^{03}$ each independently represents a hydrogen atom, a monovalent saturated chain hydrocarbon group of 1 to 10 carbon atoms or a monovalent saturated aliphatic cyclic hydrocarbon group of 3 to 20 carbon atoms, provided that part or all of the hydrogen atoms of the saturated chain hydrocarbon or the saturated aliphatic cyclic hydrocarbon may be substituted; two or more of $Ra^{01}$ to $Ra^{03}$ may be mutually bonded to form a cyclic structure. In formula (a1-r2-3), Yaa represents a carbon atom; Xaa represents a group which forms an aliphatic cyclic group together with Yaa; $Ra^{04}$ represents an aromatic hydrocarbon group which may have a substituent. In formula (a1-r2-4), $Ra'^{12}$ and $Ra'^{13}$ each independently represents a hydrogen atom or a monovalent saturated hydrocarbon group of 1 to 10 carbon atoms, provided that part or all of the hydrogen atoms of the saturated hydrocarbon group may be substituted; $Ra'^{14}$ represents a hydrocarbon group which may have a substituent; and * represents a valence bond (the same definition hereafter).

[Chemical Formula 10.]

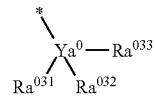

(a1-r2-r1)

In the formula, $Ya^0$ represents a quaternary carbon atom; $Ra^{031}$, $Ra^{032}$ and $Ra^{033}$ each independently represents a hydrocarbon group which may have a substituent; provided that at least one $Ra^{031}$, $Ra^{032}$ and $Ra^{033}$ is a hydrocarbon group having a polar group.

In the formula (a1-r2-1), as the alkyl group of 1 to 10 carbon atoms for Ra'10, the same groups as described above for the linear or branched alkyl group for $Ra'^3$ in the formula (a1-r-1) are preferable. $Ra'^{10}$ is preferably an alkyl group of 1 to 5 carbon atoms.

In formula (a1-r2-r1), $Ya^0$ represents a quaternary carbon atom. That is, the number of carbon atoms bonded to $Ya^0$ (carbon atom) is 4.

In formula (a1-r2-r1), $Ra^{031}$, $Ra^{032}$ and $Ra^{033}$ each independently represents a hydrocarbon group which may have a substituent. Examples of the hydrocarbon group for $Ra^{031}$, $Ra^{032}$ and $Ra^{033}$ include a linear or branched alkyl group, a chain or cyclic alkenyl group, and a cyclic hydrocarbon group.

The linear alkyl group for $Ra^{031}$, $Ra^{032}$ and $Ra^{033}$ preferably has 1 to 5 carbon atoms, more preferably 1 to 4 carbon atoms, and still more preferably 1 or 2 carbon atoms. Specific examples include a methyl group, an ethyl group, an n-propyl group, an n-butyl group and an n-pentyl group. Among these, a methyl group, an ethyl group or an n-butyl group is preferable, and a methyl group or an ethyl group is more preferable.

The branched alkyl group for $Ra^{031}$, $Ra^{032}$ and $Ra^{033}$ preferably has 3 to 10 carbon atoms, and more preferably 3 to 5 carbon atoms. Specific examples include an isopropyl group, an isobutyl group, a tert-butyl group, an isopentyl group, a neopentyl group a 1,1-diethylpropyl group and a 2,2-dimethylbutyl group. Among these, an isopropyl group is preferable.

The chain or cyclic alkenyl group for $Ra^{031}$, $Ra^{032}$ and $Ra^{033}$ is preferably an alkenyl group having 2 to 10 carbon atoms.

The cyclic hydrocarbon group for $Ra^{031}$, $Ra^{032}$ and $Ra^{033}$ may be an aliphatic hydrocarbon group or an aromatic hydrocarbon group, and may be polycyclic or monocyclic.

As the monocyclic aliphatic hydrocarbon group, a group in which 1 hydrogen atom has been removed from a monocycloalkane is preferable. The monocycloalkane preferably has 3 to 6 carbon atoms, and specific examples thereof include cyclopentane and cyclohexane.

As the polycyclic aliphatic hydrocarbon group, a group in which 1 hydrogen atom has been removed from a polycycloalkane is preferable, and the polycyclic group preferably has 7 to 12 carbon atoms. Examples of the polycycloalkane include adamantane, norbornane, isobornane, tricyclodecane and tetracyclododecane.

The aromatic hydrocarbon group for $Ra^{031}$, $Ra^{032}$ and $Ra^{033}$ is a hydrocarbon group having at least one aromatic ring. The aromatic ring is not particularly limited, as long as it is a cyclic conjugated compound having (4n+2) π electrons, and may be either monocyclic or polycyclic. The aromatic ring preferably has 5 to 30 carbon atoms, more preferably 5 to 20, still more preferably 6 to 15, and most preferably 6 to 12. Examples of the aromatic ring include aromatic hydrocarbon rings, such as benzene, naphthalene, anthracene and phenanthrene; and aromatic hetero rings in which part of the carbon atoms constituting the aforementioned aromatic hydrocarbon rings has been substituted with a hetero atom. Examples of the hetero atom within the aromatic hetero rings include an oxygen atom, a sulfur atom and a nitrogen atom. Specific examples of the aromatic hetero ring include a pyridine ring and a thiophene ring. Specific examples of the aromatic hydrocarbon group include a group in which one hydrogen atom has been removed from the aforementioned aromatic hydrocarbon ring or aromatic hetero ring (aryl group or heteroaryl group); a group in which one hydrogen atom has been removed from an aromatic compound having two or more aromatic rings (biphenyl, fluorene or the like); and a group in which one hydrogen atom of the aforementioned aromatic hydrocarbon ring or aromatic hetero ring has been substituted with an alkylene group (an arylalkyl group such as a benzyl group, a phenethyl group, a 1-naphthylmethyl group, a 2-naphthylmethyl group, a 1-naphthylethyl group, or a 2-naphthylethyl group). The alkylene group bonded to the aforementioned aromatic hydrocarbon ring or the aromatic hetero ring preferably has 1 to 4 carbon atoms, more preferably 1 or 2 carbon atoms, and most preferably 1 carbon atom.

In the case where the hydrocarbon group for $Ra^{031}$, $Ra^{032}$ and $Ra^{033}$ is substituted, examples of the substituent include a hydroxy group, a carboxy group, a halogen atom (such as a fluorine atom, a chlorine atom or a chlorine atom), an alkoxy group (such as a methoxy group, an ethoxy group, a propoxy group or a butoxy group), and an alkyloxycarbonyl group.

Among these examples, as the hydrocarbon group (which may have a substituent) for $Ra^{031}$, $Ra^{032}$ and $Ra^{033}$, a linear or branched alkyl group which may have a substituent is preferable, and a linear alkyl group is more preferable.

However, at least one of $Ra^{031}$, $Ra^{032}$ and $Ra^{033}$ is a hydrocarbon group having a polar group.

The "hydrocarbon group having a polar group" includes a group in which a methylene group (—$CH_2$—)constituting the hydrocarbon group is substituted with a polar group, and a group in which at least one hydrogen atom constituting the hydrocarbon group has been substituted with a polar group.

Examples of the "hydrocarbon group having a polar group" include a functional group represented by general formula (a1-p1) shown below.

[Chemical Formula 11.]

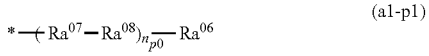

(a1-p1)

In the formula, $Ra^{07}$ represents a divalent hydrocarbon group having 2 to 12 carbon atoms; $Ra^{08}$ represents a divalent linking group containing a hetero atom; $Ra^{06}$ represents a monovalent hydrocarbon group having 1 to 12 carbon atoms;

and $n_{p0}$ represents an integer of 1 to 6.

In formula (a1-p1), $Ra^{07}$ represents a divalent hydrocarbon group having 2 to 12 carbon atoms.

$Ra^{07}$ has 2 to 12 carbon atoms, preferably 2 to 8 carbon atoms, more preferably 2 to 6 carbon atoms, still more preferably 2 to 4 carbon atoms, and most preferably 2 carbon atoms.

The hydrocarbon group for $Ra^{07}$ is preferably a chain or cyclic aliphatic hydrocarbon group, and more preferably a chain hydrocarbon group.

Examples of $Ra^{07}$ include a linear alkanediyl group, such as an ethylene group, a propane-1,3-diyl group, butane-1,4-diyl group, a pentane-1,5-diyl group, a hexane-1,6-diyl group, a heptane-1,7-diyl group, an octane-1,8-diyl group, a nonane-1,9-diyl group, a decane-1,10-diyl group, an undecane-1,11-diyl group, and a dodecane-1,12-diyl group; a branched alkanediyl group, such as a propane-1,2-diyl group, a 1-methylbutane-1,3-diyl group, a 2-methylpropane-1,3-diyl group, a pentane-1,4-diyl group, and a 2-methylbutane-1,4-diyl group; a cycloalkanediyl group, such as a cyclobutane-1,3-diyl group, a cyclopentane-1,3-diyl group, a cyclohexane-1,4-diyl group, and a cyclooctane-1,5-diyl group; and a polycyclic divalent alicyclic hydrocarbon group, such as a norbornane-1,4-diyl group, a norbornane-2,5-diyl group, an adamantane-1,5-diyl group, and an adamantane-2,6-diyl group.

Among these examples, an alkanediyl group is preferable, and a linear alkanediyl group is more preferable.

In formula (a1-p1), $Ra^{08}$ represents a divalent linking group containing a hetero atom.

Examples of $Ra^{08}$ include —O—, —C(=O)—O—, —C(=O)—, —O—C(=O)—O—, —C(=O)—NH—, —NH—, –NH—C(=NH)— (H may be substituted with a substituent such as an alkyl group or an acyl group), —S—, —S(=O)$_2$—, and —S(=O)$_2$—O—.

Among these examples, in terms of solubility in a developing solution, —O—, —C(=O)—O—, —C(=O)—, or —O—C(=O)—O— are preferable, and —O— or —C(=O)— is most preferable.

In formula (a1-p1), $Ra^{06}$ represents a monovalent hydrocarbon group having 1 to 12 carbon atoms.

$Ra^{06}$ has 1 to 12 carbon atoms. In terms of solubility in a developing solution, $Ra^{06}$ preferably has 1 to 8 carbon atoms, more preferably 1 to 5 carbon atoms, still more preferably 1 to 3 carbon atoms, still more preferably 1 or 2 carbon atoms, and most preferably 1 carbon atoms.

Examples of the hydrocarbon group for $Ra^{06}$ include a chain hydrocarbon group, a cyclic hydrocarbon group, and a combination of a chain hydrocarbon group and a cyclic hydrocarbon group.

Examples of the chain hydrocarbon group include a methyl group, an ethyl group, an n-propyl group, an isopropyl group, an n-butyl group, a sec-butyl group, a tert-butyl group, an n-pentyl group, an n-hexyl group, an n-heptyl group, a 2-ethylhexyl group, an n-octyl group, an n-nonyl group, an n-decyl group, an n-undecyl group and an n-dodecyl group.

The cyclic hydrocarbon group may be an alicyclic hydrocarbon group or an aromatic hydrocarbon group.

The alicyclic hydrocarbon group may be monocyclic or polycyclic. Examples of monocyclic alicyclic hydrocarbon groups include cycloalkyl groups, such as a cyclopropyl group, a cyclobutyl group, a cyclopentyl group, a cyclohexyl group, a dimethylcyclohexyl group, a cycloheptyl group, a cyclooctyl group, a cycloheptyl group, and a cyclodecyl group. Examples of polycyclic alicyclic hydrocarbon groups include a decahydronaphthyl group, an adamantyl group, a 2-alkyladamantan-2-yl group, a 1-(adamantan-1-yl)alkan-1-yl group, a norbornyl group, a methylnorbornyl group, and an isonorbornyl group.

Examples of aromatic hydrocarbon groups include a phenyl group, a naphthyl group, an anthryl group, a p-methylphenyl group, a p-tert-butylphenyl group, a p-adamantylphenyl group, a tolyl group, a xylyl group, a cumenyl group, a mesityl group, a biphenyl group, a phenanthryl group, 2,6-diethylphenyl group, and 2-methyl-6-ethyl phenyl group.

In terms of solubility in a developing solution, $Ra^{06}$ is preferably a chain hydrocarbon group, more preferably an alkyl group, and still more preferably a linear alkyl group.

In formula (a1-p1), $n_{p0}$ is an integer of 1 to 6, preferably an integer of 1 to 3, more preferably 1 or 2, and still more preferably 1.

Specific examples of the hydrocarbon group having a polar group are shown below.

In the following formulae, * represents a valence bond which is bonded to the quaternary carbon atom ($Ya^0$).

[Chemical Formula 12.]

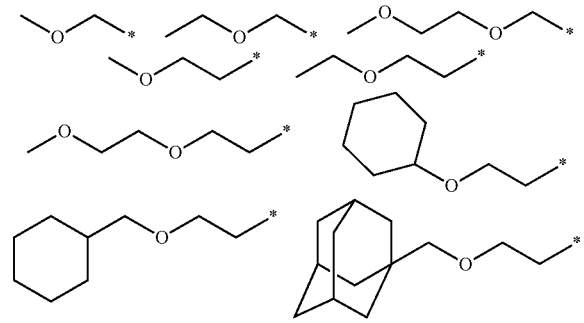

In formula (a1-r2-r1), at least one of $Ra^{031}$, $Ra^{032}$ and $Ra^{033}$ is a hydrocarbon group having a polar group. However, the number of hydrocarbon groups having a polar group may be appropriately selected depending on the solubility in the developing solution used in the formation of a resist pattern. For example, it is preferable that one or two of $Ra^{031}$, $Ra^{032}$ and $Ra^{033}$ is a hydrocarbon group having a polar group, and it is more preferable that one of $Ra^{031}$, $Ra^{032}$ and $Ra^{033}$ is hydrocarbon group having a polar group.

The hydrocarbon group having a polar group may have a substituent other than a polar group.

Examples of such substituent include a halogen atom (such as a fluorine atom, a chlorine atom or a bromine atom), and a halogenated alkyl group having 1 to 5 carbon atoms.

In formula (a1-r2-1), the aliphatic cyclic group which is formed by $Ra'^{11}$ together with the carbon atom bonded to $Ra'^{10}$, the same groups as those described above for the monocyclic or polycyclic aliphatic hydrocarbon group for $Ra'^{3}$ in formula (a1-r-1) are preferable.

In formula (a1-r2-2), as the cyclic hydrocarbon group formed by Xa together with Ya, a group in which 1 or more hydrogen atoms have been removed from the monovalent cyclic hydrocarbon group (aliphatic hydrocarbon group) for $Ra'^{3}$ in the aforementioned formula (a1-r-1) may be mentioned.

The cyclic hydrocarbon group which Xa forms with Ya may have a substituent. Examples of substituents include the same substituents as those which the cyclic hydrocarbon group for $Ra'^{3}$ may have.

In formula (a1-r2-2), examples of the monovalent saturated chain hydrocarbon group of 1 to 10 carbon atoms for $Ra^{01}$ to $Ra^{03}$ include a methyl group, an ethyl group, a propyl group, a butyl group, a pentyl group, a hexyl group, a heptyl group, an octyl group, and a decyl group.

Examples of the monovalent aliphatic cyclic saturated hydrocarbon group having 3 to 20 carbon atoms for $Ra^{01}$ to $Ra^{03}$ include a monocyclic aliphatic saturated hydrocarbon group such as a cyclopropyl group, a cyclobutyl group, a cyclopentyl group, a cyclohexyl group, a cycloheptyl group, a cyclooctyl group, a cyclodecyl group, and a cyclododecyl group; and a polycyclic aliphatic saturated hydrocarbon group such as a bicyclo[2.2.2]octanyl group, a tricyclo[5.2.1.0²,⁶]decanyl group, a tricyclo[3.3.1.1³,⁷]decanyl group, a tetracyclo[6.2.1.1³,⁶.0²,⁷]dodecanyl group, and an adamantyl group.

Among these examples, as $Ra^{01}$ to $Ra^{03}$, in terms of ease in synthesis of the monomeric compound which derives the structural unit (a1), a hydrogen atom or a saturated chain hydrocarbon group having 1 to 10 carbon atoms is preferable, a hydrogen atom, a methyl group or an ethyl group is more preferable, and a hydrogen atom is most preferable.

As the substituent for the saturated chain hydrocarbon group or saturated cyclic aliphatic hydrocarbon group represented by $Ra^{01}$ to $Ra^{03}$, for example, the same substituents as those described above for $Ra^{05}$ may be mentioned.

Examples of the group containing a carbon-carbon double bond which is generated by forming a cyclic structure in which two or more of $Ra^{01}$ to $Ra^{03}$ are bonded to each other include a cyclopentenyl group, a cyclohexenyl group, a methyl cyclopentenyl group, a methyl cyclohexenyl group, a cyclopentylideneethenyl group, and a cyclohexylideneethenyl group. Among these examples, from the viewpoint of the ease of synthesis of the monomer compound which derives the structural unit (a1), a cyclopentenyl group, a cyclohexenyl group, and a cyclopentylideneethenyl group are preferable.

In formula (a1-r2-3), an aliphatic cyclic group which is formed of Xaa together with Yaa is preferably a group exemplified as an aliphatic hydrocarbon group which is a monocyclic group or a polycyclic group of Ra$^{i3}$ in general formula (a1-r-1). In general formula (a1-r2-3), examples of the aromatic hydrocarbon group for Ra$^4$ include a group obtained by removing one or more hydrogen atoms from an aromatic hydrocarbon ring having 5 to 30 carbon atoms. Among these examples, Ra$^4$ is preferably a group obtained by removing one or more hydrogen atoms from an aromatic hydrocarbon ring having 6 to 15 carbon atoms, a group obtained by removing one or more hydrogen atoms from benzene, naphthalene, anthracene, or phenanthrene is further preferable, a group obtained by removing one or more hydrogen atoms from benzene, naphthalene, or anthracene is still further preferable, a group obtained by removing one or more hydrogen atoms from benzene and naphthalene is particularly preferable, and a group obtained by removing one or more hydrogen atoms from benzene is most preferable.

Examples of the substituent that Ra$^4$ in general formula (a1-r2-3) may have include a methyl group, an ethyl group, a propyl group, a hydroxyl group, a carboxyl group, a halogen atom (a fluorine atom, a chlorine atom, a bromine atom, or the like), an alkoxy group (a methoxy group, an ethoxy group, a propoxy group, a butoxy group, or the like), and an alkyloxycarbonyl group.

In general formula (a1-r2-4), Ra$^{i12}$ and Ra$^{i13}$ each independently represent a monovalent chain saturated hydrocarbon group having 1 to 10 carbon atoms or a hydrogen atom. With respect to Ra$^{i12}$ and Ra$^{i13}$, examples of the monovalent chain saturated hydrocarbon group having 1 to 10 carbon atoms include the same monovalent chain saturated hydrocarbon group having 1 to 10 carbon atoms as that for Ra$^{o1}$ to Ra$^{o3}$ provided that part or all of the hydrogen atoms of the saturated hydrocarbon group may be substituted;

Among these examples, as Ra$^{i12}$ and Ra$^{i13}$, a hydrogen atom and an alkyl group having 1 to 5 carbon atoms are preferable, an alkyl group having 1 to 5 carbon atoms is further preferable, a methyl group and an ethyl group are still further preferable, and a methyl group is particularly preferable.

In the case where the chain saturated hydrocarbon group represented by Ra$^{i12}$ and Ra$^{i13}$ is substituted, examples of the substituent include the same group as that of Ra$^{o5}$.

In general formula (a1-r2-4), Ra$^{i14}$ is a hydrocarbon group which may have a substituent. Examples of the hydrocarbon group for Ra$^{i14}$ include a linear or branched alkyl group and a cyclic hydrocarbon group.

The linear alkyl group for Ra$^{i14}$ preferably has 1 to 5 carbon atoms, more preferably 1 to 4 carbon atoms, and still more preferably 1 or 2 carbon atoms. Specific examples include a methyl group, an ethyl group, an n-propyl group, an n-butyl group and an n-pentyl group. Among these, a methyl group, an ethyl group or an n-butyl group is preferable, and a methyl group or an ethyl group is more preferable.

The branched alkyl group for Ra$^{i14}$ preferably has 3 to 10 carbon atoms, and more preferably 3 to 5 carbon atoms. Specific examples include an isopropyl group, an isobutyl group, a tert-butyl group, an isopentyl group, a neopentyl group a 1,1-diethylpropyl group and a 2,2-dimethylbutyl group. Among these, an isopropyl group is preferable.

In the case where Ra$^{i14}$ represents a cyclic hydrocarbon group, the cyclic hydrocarbon group may be an aliphatic hydrocarbon group or an aromatic hydrocarbon group, and may be polycyclic or monocyclic.

As the monocyclic aliphatic hydrocarbon group, a group in which 1 hydrogen atom has been removed from a monocycloalkane is preferable. The monocycloalkane preferably has 3 to 6 carbon atoms, and specific examples thereof include cyclopentane and cyclohexane.

As the polycyclic aliphatic hydrocarbon group, a group in which 1 hydrogen atom has been removed from a polycycloalkane is preferable, and the polycyclic group preferably has 7 to 12 carbon atoms. Examples of the polycycloalkane include adamantane, norbornane, isobornane, tricyclodecane and tetracyclododecane.

Examples of the aromatic hydrocarbon group for Ra$^{i14}$ include the same aromatic hydrocarbon groups as those described above for Ra$^4$. Among these examples, Ra$^{i14}$ is preferably a group formed by removing one or more hydrogen atoms from an aromatic hydrocarbon ring having 6 to 15 carbon atoms, more preferably a group formed by removing one or more hydrogen atoms from benzene, naphthalene, anthracene, or phenanthrene, still more preferably a group formed by removing one or more hydrogen atoms from benzene, naphthalene, or anthracene, still more preferably a group formed by removing one or more hydrogen atoms from naphthalene or anthracene, and most preferably a group formed by removing one or more hydrogen atoms from naphthalene.

Examples of the substituent that Ra$^{i14}$ may have include the same group as the substituent that Ra$^4$ may have.

In the case where Ra$^{i14}$ in general formula (a1-r2-4) is a naphthyl group, a position which is bonded to a tertiary carbon atom in general formula (a1-r2-4) may be 1-position and 2-position of the naphthyl group.

In the case where Ra$^{i14}$ in general formula (a1-r2-4) is an anthryl group, a position which is bonded to a tertiary carbon atom in general formula (a1-r2-4) may be any one of 1-position, 2-position, and 9-position of the anthryl group.

Specific examples of the group represented by the aforementioned formula (a1-r2-1) are shown below.

[Chemical Formula 13.]

(r-pr-m1)

(r-pr-m2)

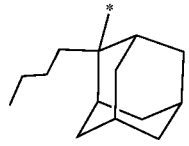

(r-pr-m3)

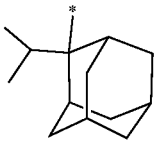

(r-pr-m4)

-continued
(r-pr-m5)
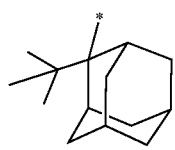
(r-pr-m6)
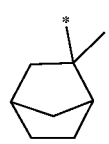
(r-pr-m7)
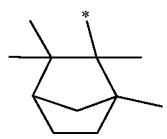
(r-pr-m8)
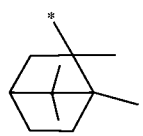
(r-pr-m9)
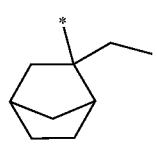
(r-pr-m10)
(r-pr-m11)
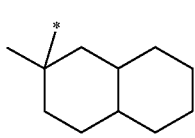
(r-pr-m12)
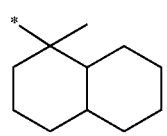
(r-pr-m13)
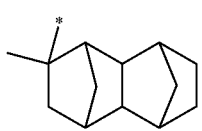
(r-pr-m14)
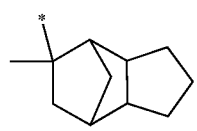
(r-pr-m15)
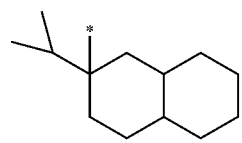
-continued
(r-pr-m16)
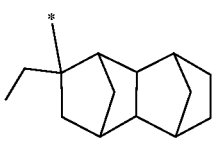
(r-pr-m17)
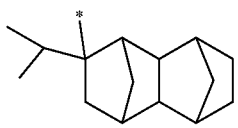
[Chemical Formula 14.]
(r-pr-s1)
(r-pr-s2)
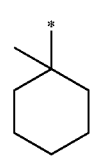
(r-pr-s3)
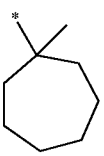
(r-pr-s4)
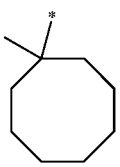
(r-pr-s5)
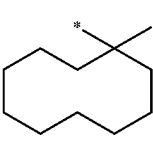
(r-pr-s6)
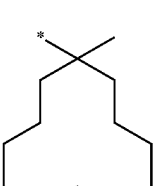
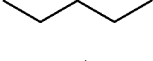
(r-pr-s7)
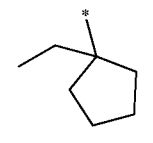
(r-pr-s8)
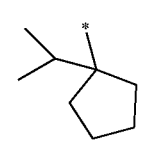

(r-pr-s9)
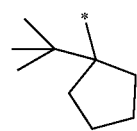
(r-pr-s10)
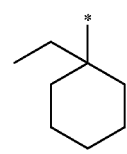
(r-pr-s11)
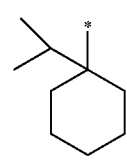
(r-pr-s12)
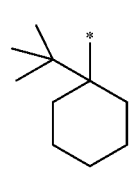
(r-pr-s13)
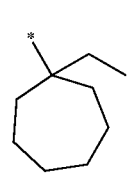
(r-pr-s14)
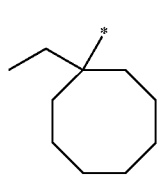
(r-pr-s15)
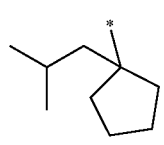
(r-pr-s16)
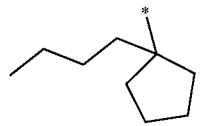
(r-pr-s17)
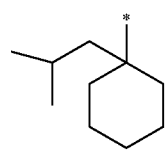
(r-pr-s18)
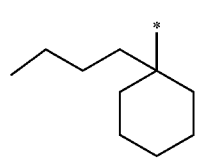
(r-pr-s19)
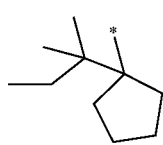
(r-pr-s20)
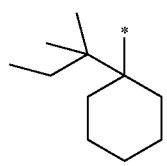
[Chemical Formula 15.]
(r-pr-sp1)
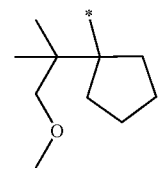
(r-pr-sp2)
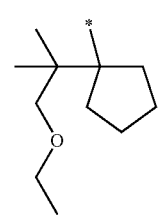
(r-pr-sp3)
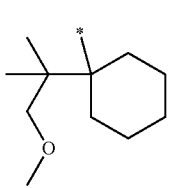
(r-pr-sp4)
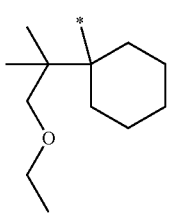
(r-pr-mp1)
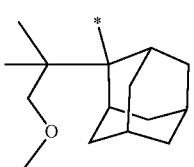
(r-pr-mp2)
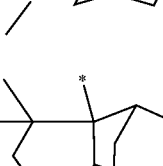
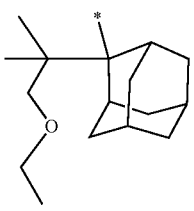

Specific examples of the group represented by the aforementioned formula (a1-r2-2) are shown below.
[Chemical Formula 16.]
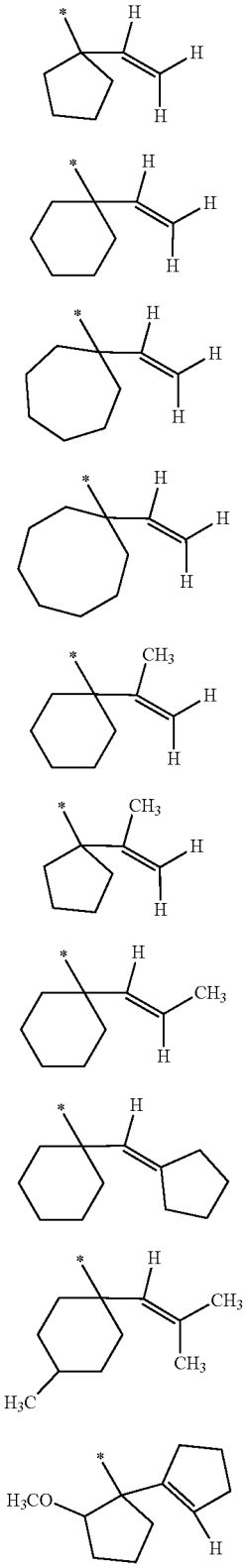
[Chemical Formula 17.]
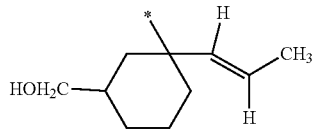
(r-pr-mv1)
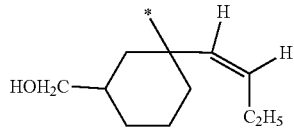
(r-pr-mv2)
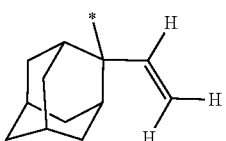
(r-pr-mv3)
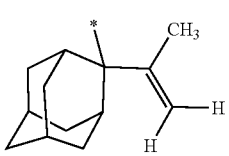
(r-pr-mv4)
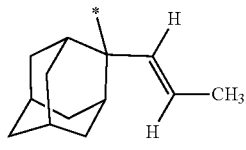
(r-pr-mv5)
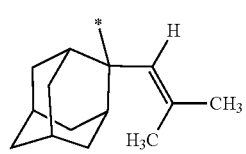
(r-pr-mv6)
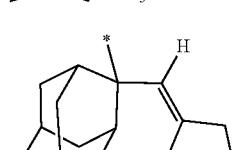
(r-pr-mv7)
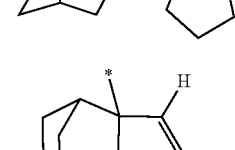
(r-pr-mv8)
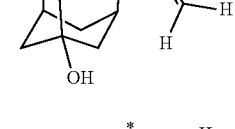
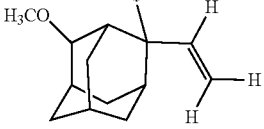
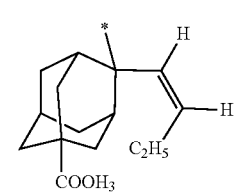

-continued
(r-pr-mv9)
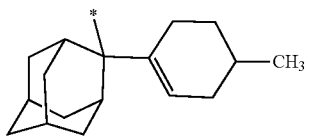
[Chemical Formula 18.]
(r-pr-mv10)
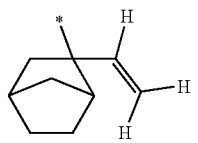
(r-pr-mv11)
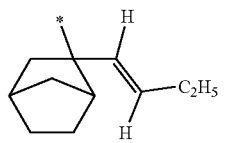
(r-pr-mv12)
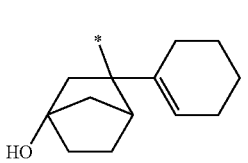
(r-pr-mv13)
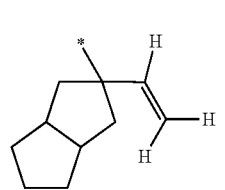
(r-pr-mv14)
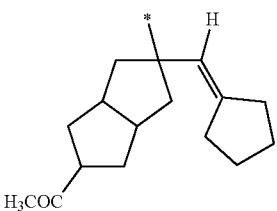
(r-pr-mv15)
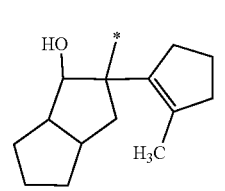
(r-pr-mv16)
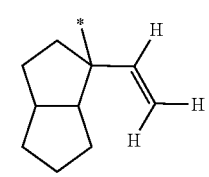
(r-pr-mv17)
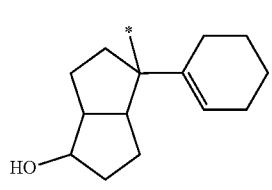
-continued
(r-pr-mv18)
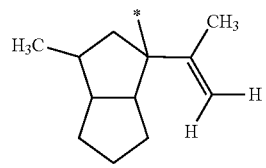
(r-pr-mv19)
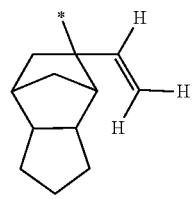
(r-pr-mv20)
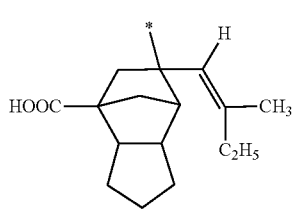
(r-pr-mv21)
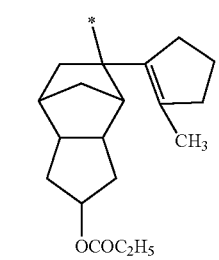
Specific examples of the group represented by the aforementioned formula (a1-r2-3) are shown below.
[Chemical Formula 19.]
(r-pr-sa1)
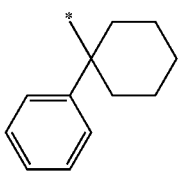
(r-pr-sa2)
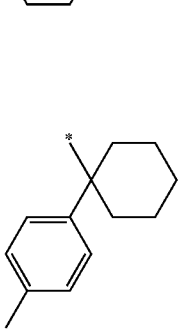

(r-pr-sa3) 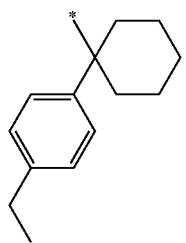
(r-pr-sa4) 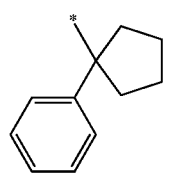
(r-pr-sa5) 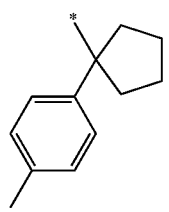
(r-pr-sa6) 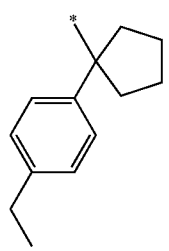
(r-pr-sa7) 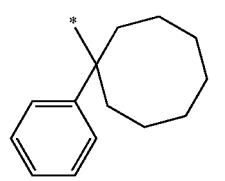
(r-pr-sa8) 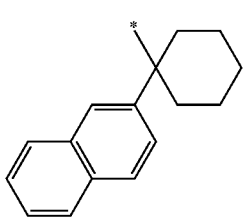
(r-pr-sa9) 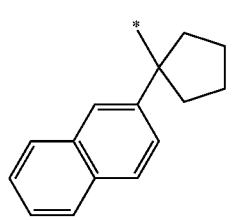
(r-pr-ma1) 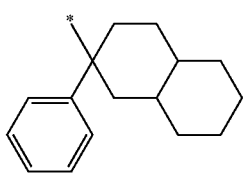
(r-pr-ma2) 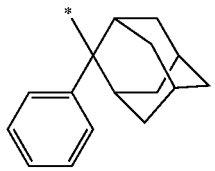
Specific examples of the group represented by the aforementioned formula (a1-r2-4) are shown below.
[Chemical Formula 20.]
(r-pr-cm1) 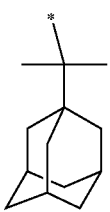
(r-pr-cm2) 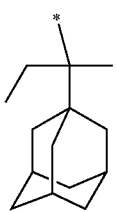
(r-pr-cm3) 
(r-pr-cm4) 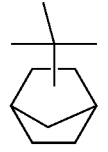
(r-pr-cm5) 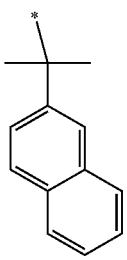

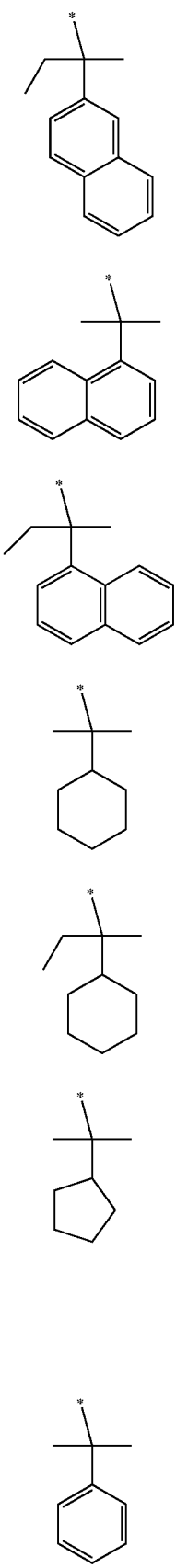

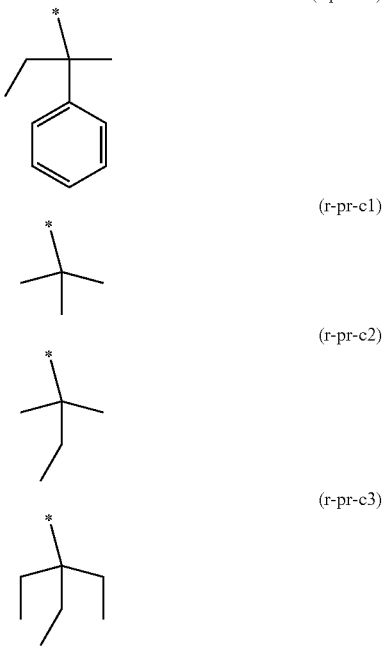

Tertiary Alkyloxycarbonyl Acid Dissociable Group

Examples of the acid dissociable group for protecting a hydroxy group as a polar group include the acid dissociable group represented by general formula (a1-r-3) shown below (hereafter, for convenience, referred to as "tertiary alkyloxycarbonyl-type acid dissociable group").

[Chemical Formula 21.]

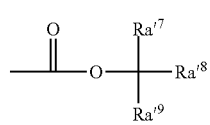

(a1-r-3)

In the formula, $Ra'^7$ to $Ra'^9$ each independently represents an alkyl group.

In formula (a1-r-3), each of $Ra'^7$ to $Ra'^9$ is preferably an alkyl group having 1 to 5 carbon atoms, and more preferably an alkyl group having 1 to 3 carbon atoms. Further, the total number of carbon atoms in the alkyl groups is preferably 3 to 7, more preferably 3 to 5, and still more preferably 3 or 4.

Examples of the structural unit (a1) include a structural unit derived from an acrylate ester which may have the hydrogen atom bonded to the carbon atom on the α-position substituted with a substituent; a structural unit derived from an acrylamide; a structural unit derived from hydroxystyrene or a hydroxystyrene derivative in which at least a part of the hydrogen atom of the hydroxy group is protected with a substituent containing an acid decomposable group; and a structural unit derived from vinylbenzoic acid or a vinylbenzoic acid derivative in which at least a part of the hydrogen atom within —C(=O)—OH is protected with a substituent containing an acid decomposable group.

As the structural unit (a1), a structural unit derived from an acrylate ester which may have the hydrogen atom bonded to the carbon atom on the α-position substituted with a substituent is preferable.

Specific examples of preferable structural units for the structural unit (a1) include structural units represented by general formula (a1-1) or (a1-2) shown below.

[Chemical Formula 22.]

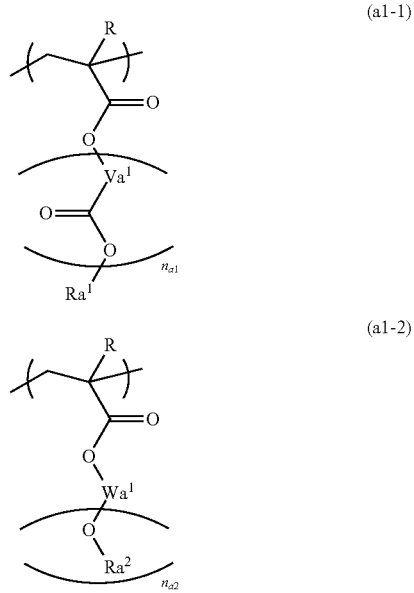

In the formula, R represents a hydrogen atom, an alkyl group of 1 to 5 carbon atoms or a halogenated alkyl group of 1 to 5 carbon atoms; $Va^1$ represents a divalent hydrocarbon group optionally having an ether bond; $n_{a1}$ represents an integer of 0 to 2; $Ra^1$ represents an acid dissociable group represented by the aforementioned formula (a1-r-1) or (a1-r-2); $Wa^1$ represents a hydrocarbon group having a valency of $n_{a2}+1$; $n_{a2}$ represents an integer of 1 to 3; and $Ra^2$ represents an acid dissociable group represented by the aforementioned general formula (a1-r-1) or (a1-r-3).

In the aforementioned formula (a1-1), as the alkyl group of 1 to 5 carbon atoms for R, a linear or branched alkyl group of 1 to 5 carbon atoms is preferable, and specific examples thereof include a methyl group, an ethyl group, a propyl group, an isopropyl group, an n-butyl group, an isobutyl group, a tert-butyl group, a pentyl group, an isopentyl group and a neopentyl group. The halogenated alkyl group of 1 to 5 carbon atoms represented by R is a group in which part or all of the hydrogen atoms of the aforementioned alkyl group of 1 to 5 carbon atoms have been substituted with halogen atoms. Examples of the halogen atom include a fluorine atom, a chlorine atom, a bromine atom and an iodine atom, and a fluorine atom is particularly desirable.

As R, a hydrogen atom, an alkyl group of 1 to 5 carbon atoms or a fluorinated alkyl group of 1 to 5 carbon atoms is preferable, and a hydrogen atom or a methyl group is particularly desirable in terms of industrial availability.

In formula (a1-1), the divalent hydrocarbon group for $V^1$ may be either an aliphatic hydrocarbon group or an aromatic hydrocarbon group.

The aliphatic hydrocarbon group as the divalent hydrocarbon group for $Va^1$ may be either saturated or unsaturated. In general, the aliphatic hydrocarbon group is preferably saturated.

As specific examples of the aliphatic hydrocarbon group, a linear or branched aliphatic hydrocarbon group, and an aliphatic hydrocarbon group containing a ring in the structure thereof can be given.

The linear aliphatic hydrocarbon group preferably has 1 to 10 carbon atoms, more preferably 1 to 6 carbon atoms, still more preferably 1 to 4 carbon atoms, and most preferably 1 to 3 carbon atoms.

As the linear aliphatic hydrocarbon group, a linear alkylene group is preferable. Specific examples thereof include a methylene group [—$CH_2$—], an ethylene group [—$(CH_2)_2$—], a trimethylene group [—$(CH_2)_3$—], a tetramethylene group [—$(CH_2)_4$—] and a pentamethylene group [—$(CH_2)_5$—].

The branched aliphatic hydrocarbon group preferably has 2 to 10 carbon atoms, more preferably 3 to 6, still more preferably 3 or 4, and most preferably 3.

As the branched aliphatic hydrocarbon group, branched alkylene groups are preferred, and specific examples include various alkylalkylene groups, including alkylmethylene groups such as —$CH(CH_3)$—, —$CH(CH_2CH_3)$—, —$C(CH_3)_2$—, —$C(CH_3)(CH_2CH_3)$—, —$C(CH_3)(CH_2CH_2CH_3)$—, and —$C(CH_2CH_3)_2$—; alkylethylene groups such as —$CH(CH_3)CH_2$—, —$CH(CH_3)CH(CH_3)$—, —$C(CH_3)_2CH_2$—, —$CH(CH_2CH_3)CH_2$—, and —$C(CH_2CH_3)_2$—$CH_2$—; alkyltrimethylene groups such as —$CH(CH_3)CH_2CH_2$—, and —$CH_2CH(CH_3)CH_2$—; and alkyltetramethylene groups such as —$CH(CH_3)CH_2CH_2CH_2$—, and —$CH_2CH(CH_3)CH_2CH_2$—. As the alkyl group within the alkylalkylene group, a linear alkyl group of 1 to 5 carbon atoms is preferable.

As examples of the hydrocarbon group containing a ring in the structure thereof, an alicyclic hydrocarbon group (a group in which two hydrogen atoms have been removed from an aliphatic hydrocarbon ring), a group in which the alicyclic hydrocarbon group is bonded to the terminal of the aforementioned chain-like aliphatic hydrocarbon group, and a group in which the alicyclic group is interposed within the aforementioned linear or branched aliphatic hydrocarbon group, can be given. The linear or branched aliphatic hydrocarbon group is the same as defined for the aforementioned linear aliphatic hydrocarbon group or the aforementioned branched aliphatic hydrocarbon group.

The alicyclic hydrocarbon group preferably has 3 to 20 carbon atoms, and more preferably 3 to 12 carbon atoms.

The alicyclic hydrocarbon group may be either a monocyclic group or a polycyclic group. As the monocyclic aliphatic hydrocarbon group, a group in which 2 hydrogen atoms have been removed from a monocycloalkane is preferable. The monocycloalkane preferably has 3 to 6 carbon atoms, and specific examples thereof include cyclopentane and cyclohexane. As the polycyclic group, a group in which two hydrogen atoms have been removed from a polycycloalkane is preferable, and the polycyclic group preferably has 7 to 12 carbon atoms. Examples of the polycycloalkane include adamantane, norbornane, isobornane, tricyclodecane and tetracyclododecane.

The aromatic hydrocarbon group as the divalent hydrocarbon group for $Va^1$ is a hydrocarbon group having an aromatic ring.

The aromatic hydrocarbon group preferably has 3 to 30 carbon atoms, more preferably 5 to 30, still more preferably 5 to 20, still more preferably 6 to 15, and most preferably 6 to 12. Here, the number of carbon atoms within a substituent(s) is not included in the number of carbon atoms of the aromatic hydrocarbon group.

Examples of the aromatic ring contained in the aromatic hydrocarbon group include aromatic hydrocarbon rings, such as benzene, biphenyl, fluorene, naphthalene, anthracene and phenanthrene; and aromatic hetero rings in which part of the carbon atoms constituting the aforementioned aromatic hydrocarbon rings has been substituted with a hetero atom. Examples of the hetero atom within the aromatic hetero rings include an oxygen atom, a sulfur atom and a nitrogen atom.

Specific examples of the aromatic hydrocarbon group include a group in which two hydrogen atoms have been removed from the aforementioned aromatic hydrocarbon ring (arylene group); and a group in which one hydrogen atom has been removed from the aforementioned aromatic hydrocarbon ring (aryl group) and one hydrogen atom has been substituted with an alkylene group (such as a benzyl group, a phenethyl group, a 1-naphthylmethyl group, a 2-naphthylmethyl group, a 1-naphthylethyl group, or a 2-naphthylethyl group). The alkylene group (alkyl chain within the arylalkyl group) preferably has 1 to 4 carbon atom, more preferably 1 or 2, and most preferably 1.

In formula (a1-1), $Ra^1$ represents an acid dissociable group represented by the aforementioned formula (a1-r-1) or (a1-r-2).

In the aforementioned formula (a1-2), the hydrocarbon group for $Wa^1$ having a valency of $n_{a2}+1$ may be either an aliphatic hydrocarbon group or an aromatic hydrocarbon group. The aliphatic cyclic group refers to a hydrocarbon group that has no aromaticity, and may be either saturated or unsaturated, but is preferably saturated. Examples of the aliphatic hydrocarbon group include a linear or branched aliphatic hydrocarbon group, an aliphatic hydrocarbon group containing a ring in the structure thereof, and a combination of the linear or branched aliphatic hydrocarbon group and the aliphatic hydrocarbon group containing a ring in the structure thereof.

The valency of $na_2+1$ is preferably divalent, trivalent or tetravalent, and divalent or trivalent is more preferable.

In formula (a1-2), $Ra^2$ represents an acid dissociable group represented by the aforementioned formula (a1-r-1) or (a1-r-3).

Specific examples of structural unit represented by formula (a1-1) are shown below. In the formulae shown below, Ra represents a hydrogen atom, a methyl group or a trifluoromethyl group.

[Chemical Formula 23.]

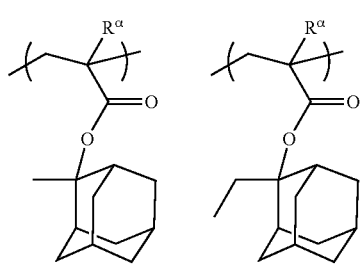

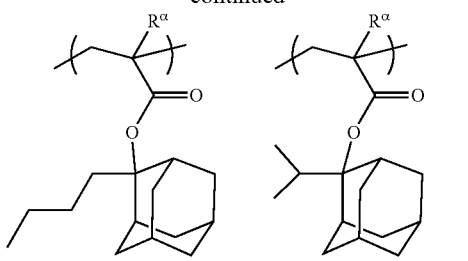

-continued

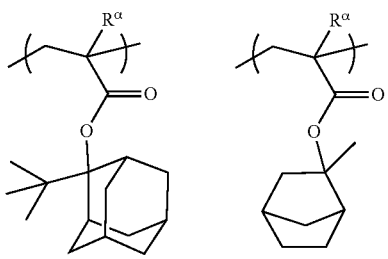

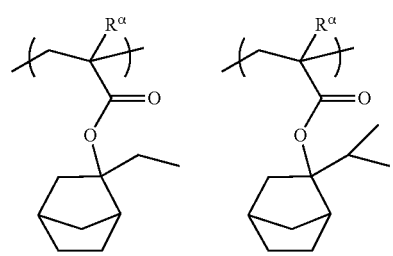

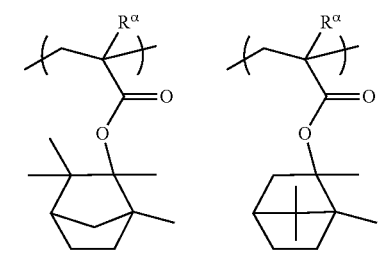

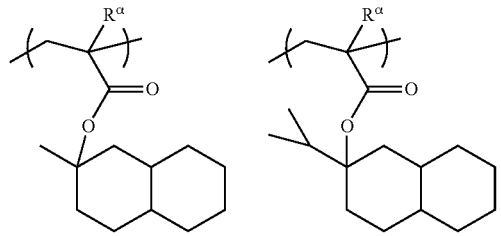

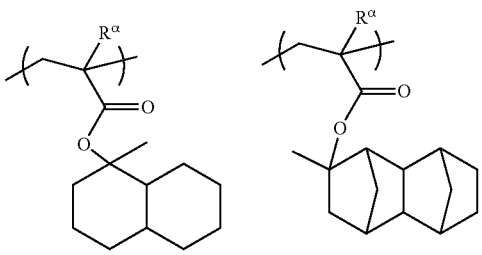

-continued
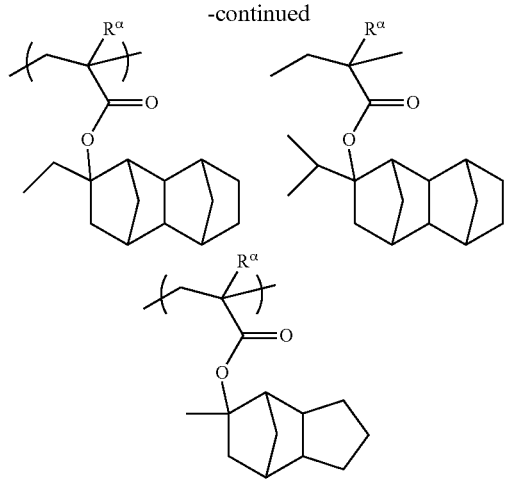
[Chemical Formula 24.]
-continued
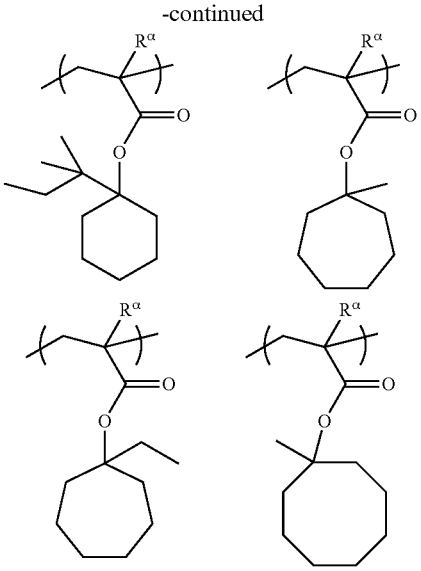
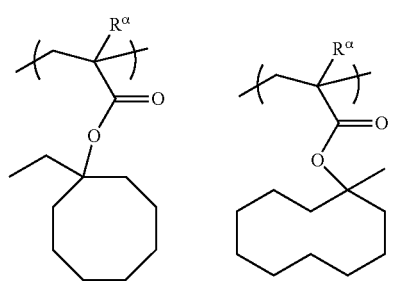
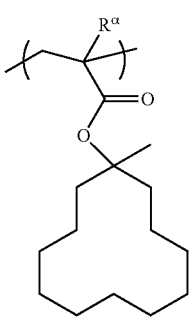
[Chemical Formula 25.]
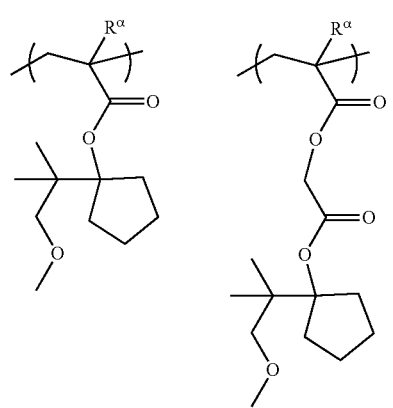

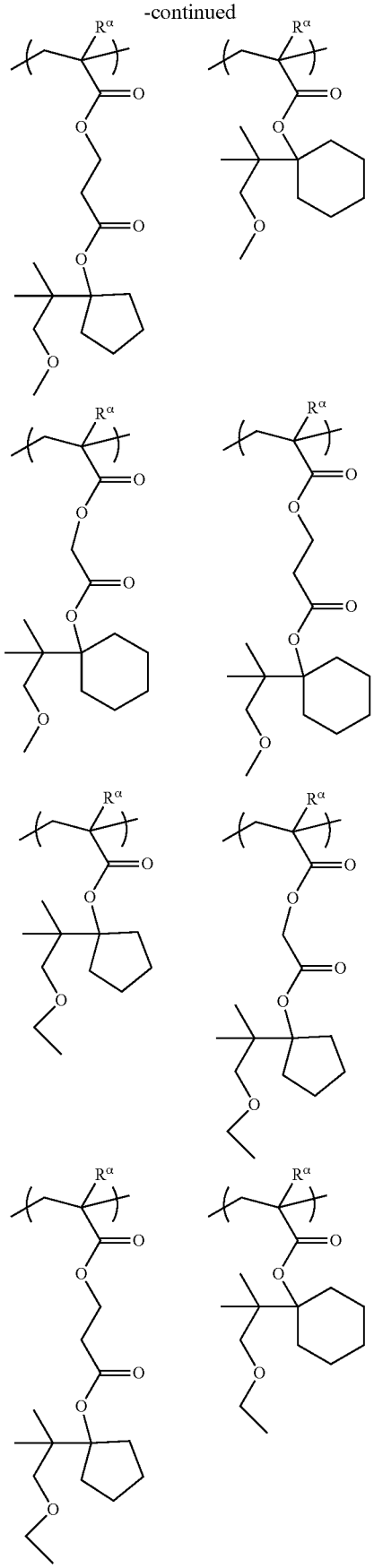
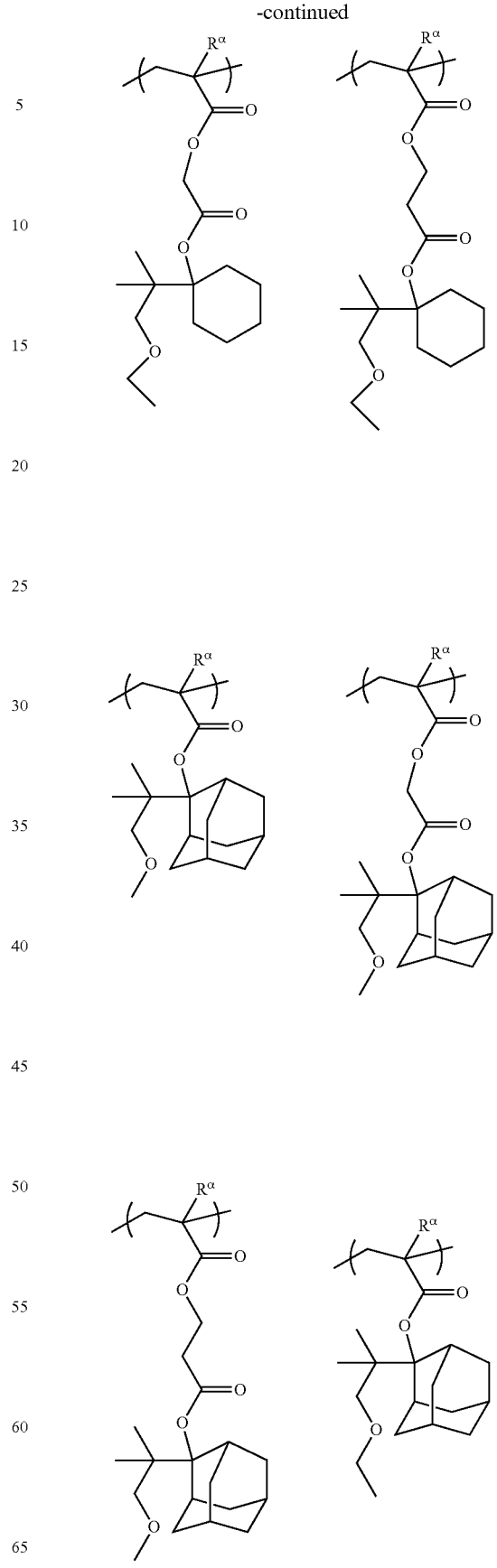

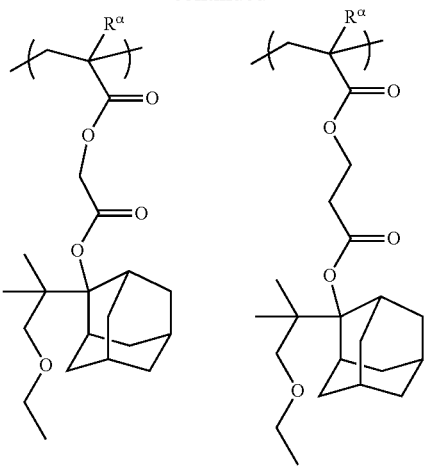
[Chemical Formula 26.]
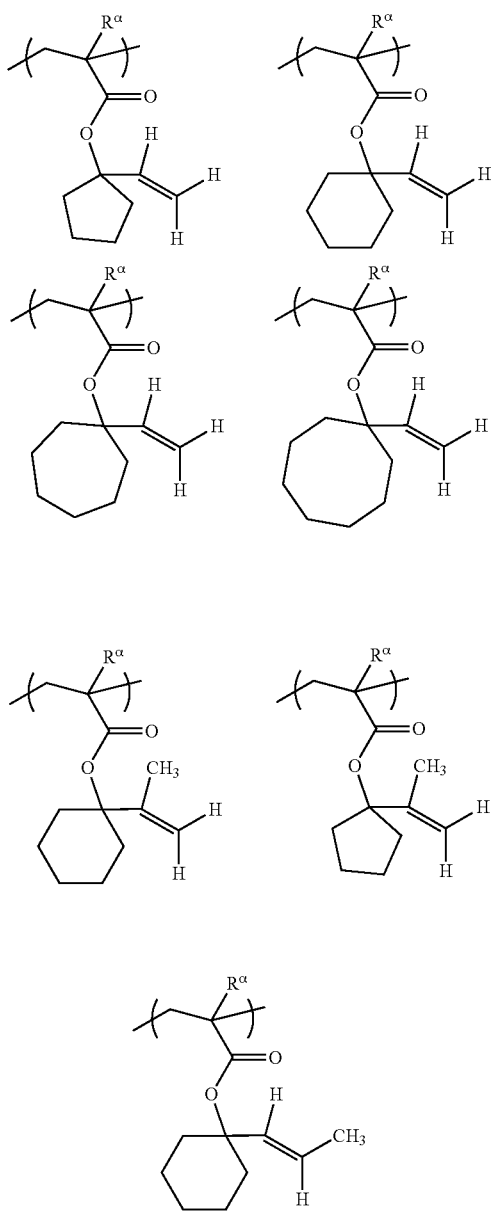
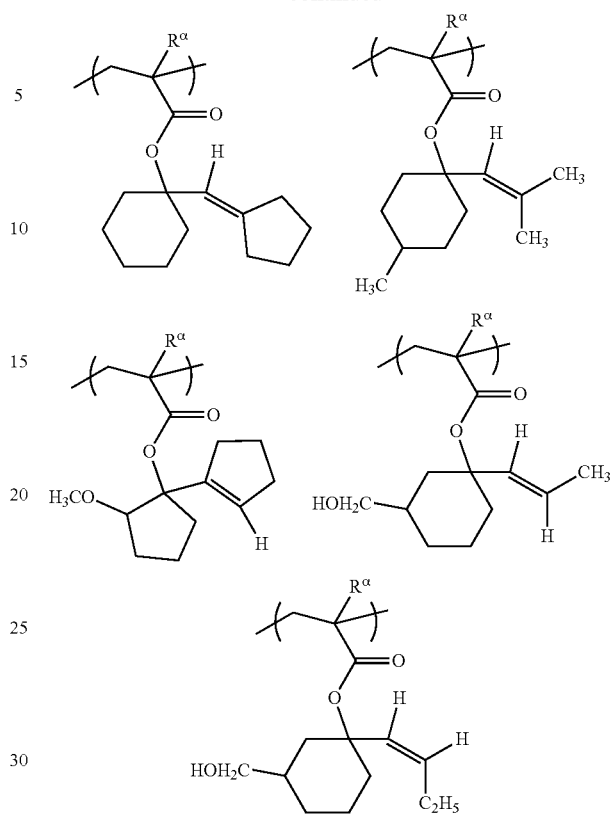
[Chemical Formula 27.]
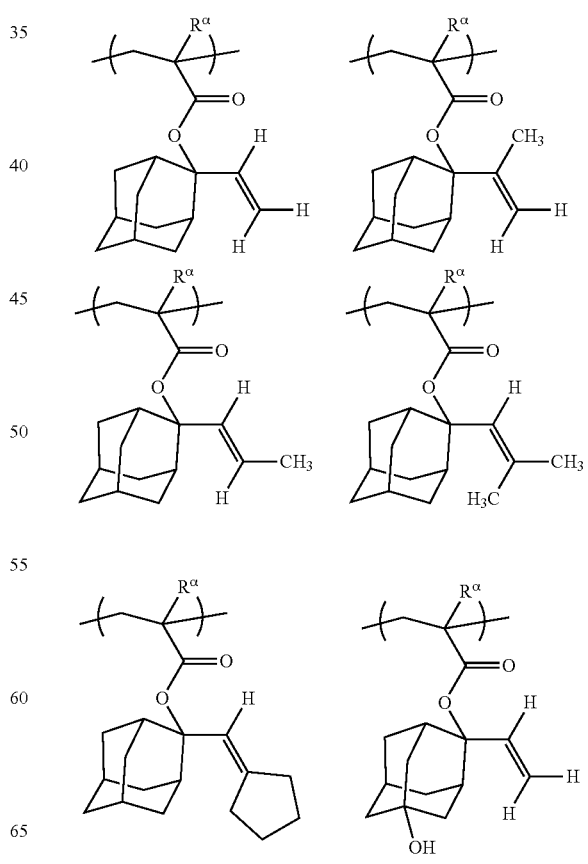

-continued
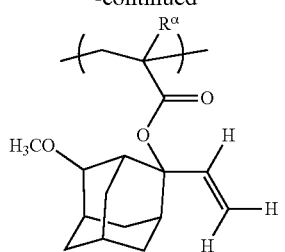
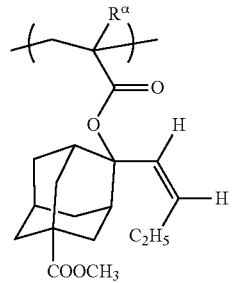
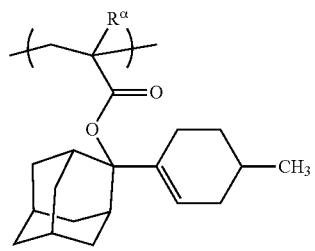
[Chemical Fomula 28.]
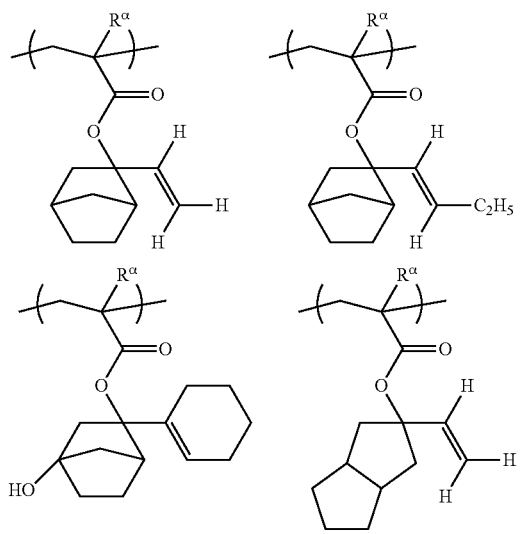
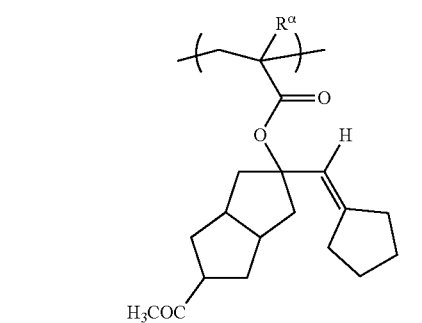
-continued
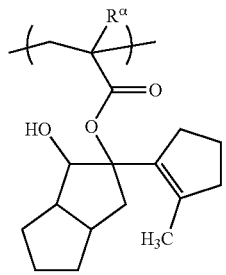
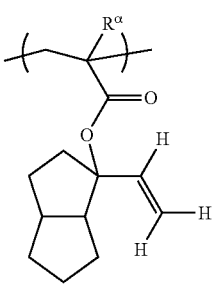
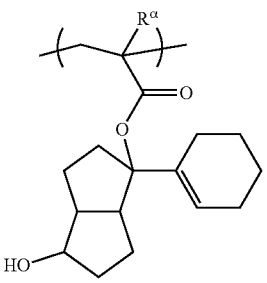
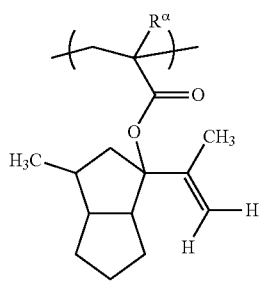
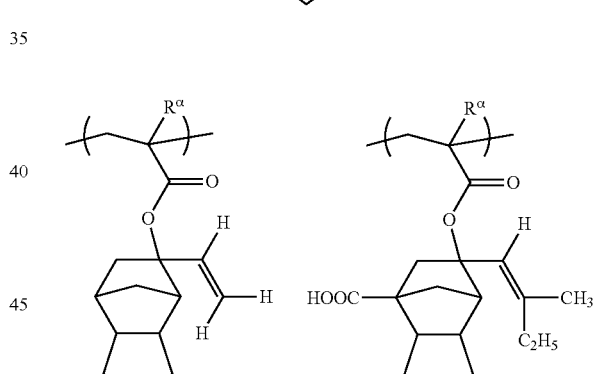
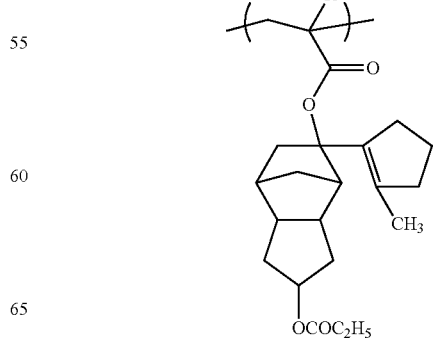

[Chemical Formula 29.]
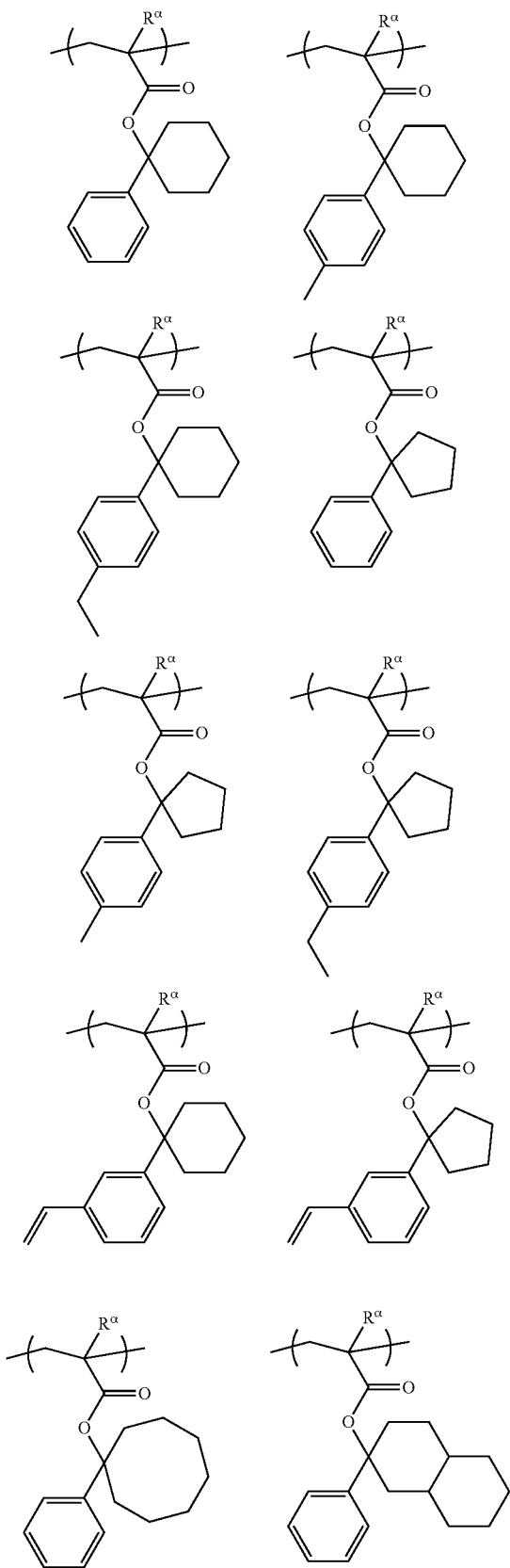
[Chemical Formula 30.]
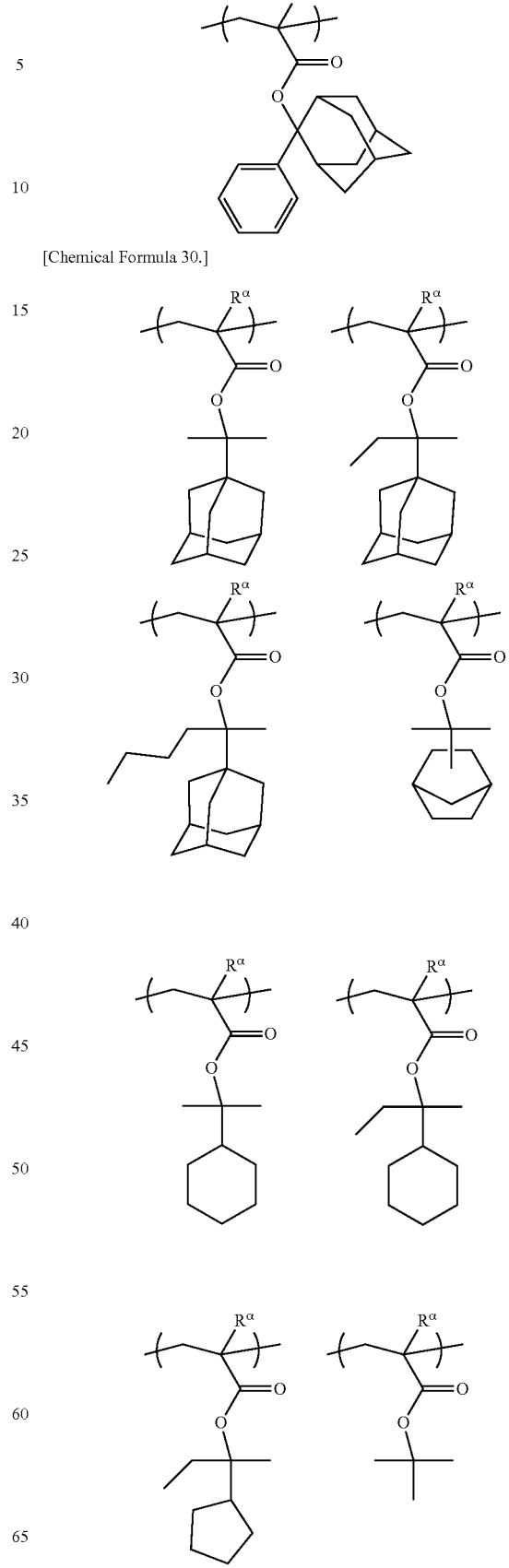

[Chemical Formula 31.]
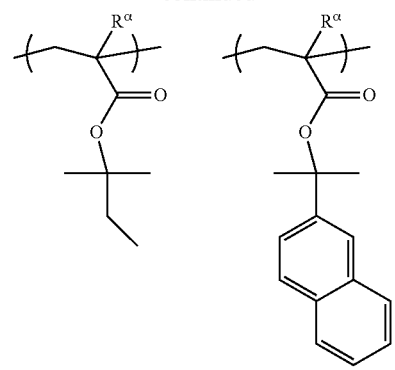
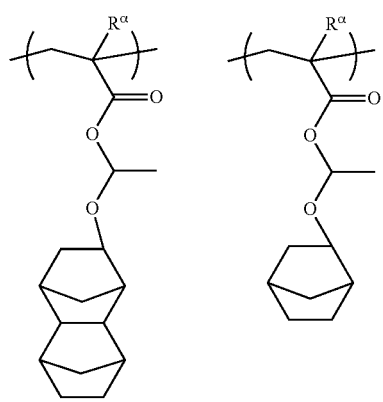
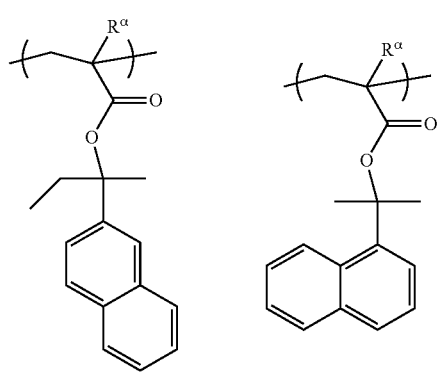
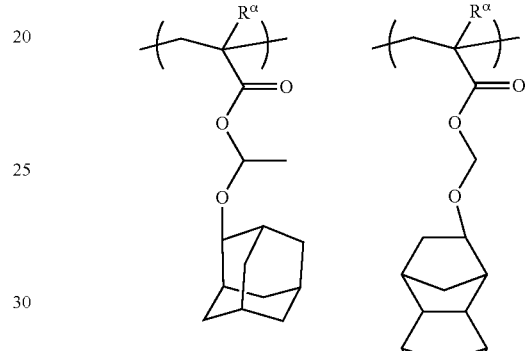
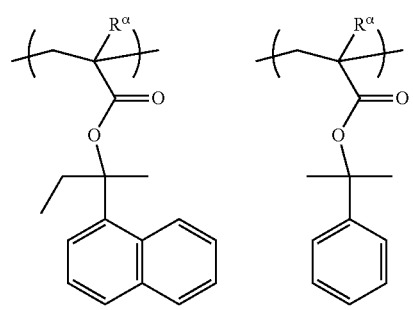
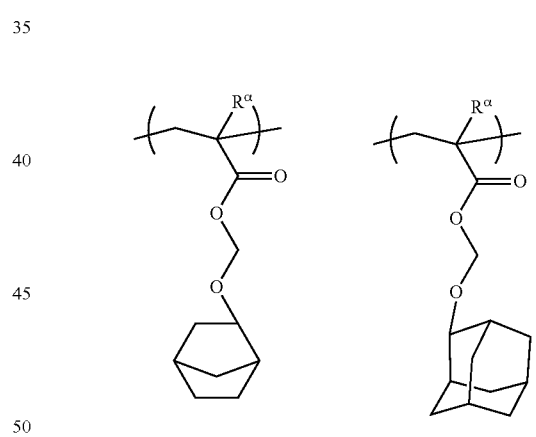
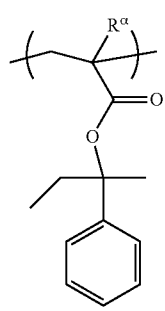
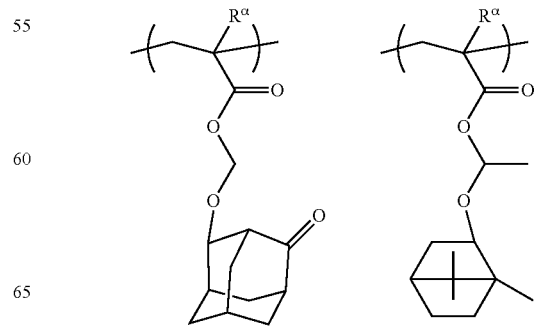

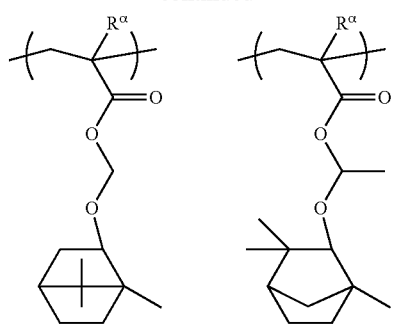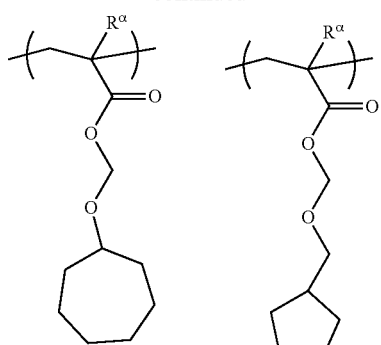
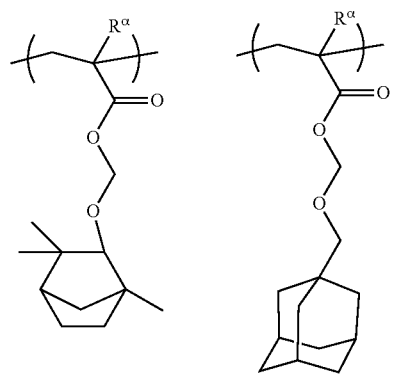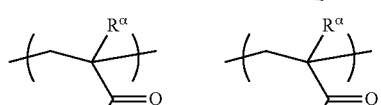
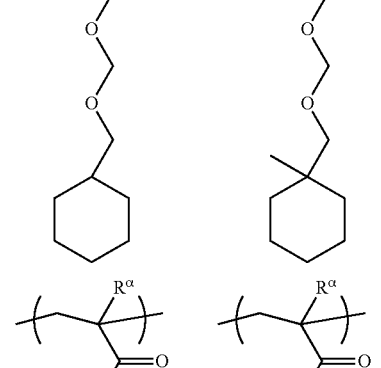
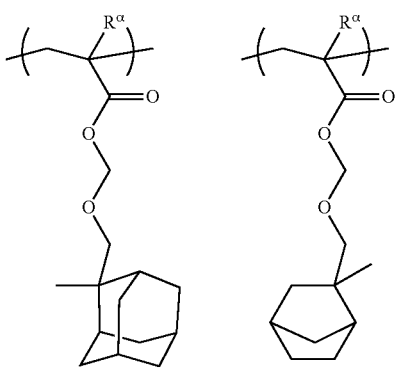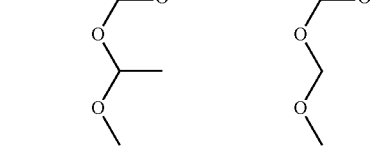
[Chemical Formula 32.]
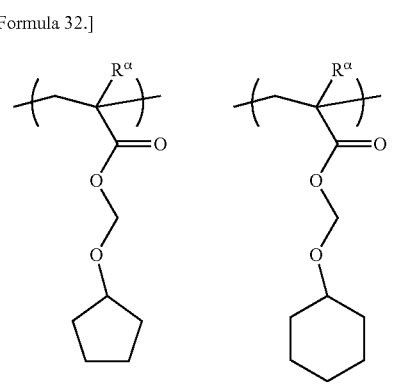
[Chemical Formula 33.]
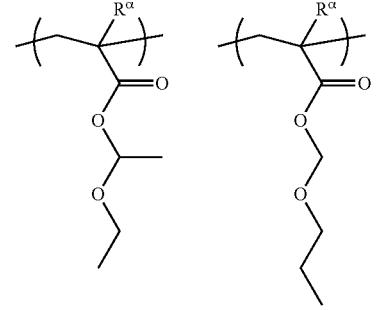

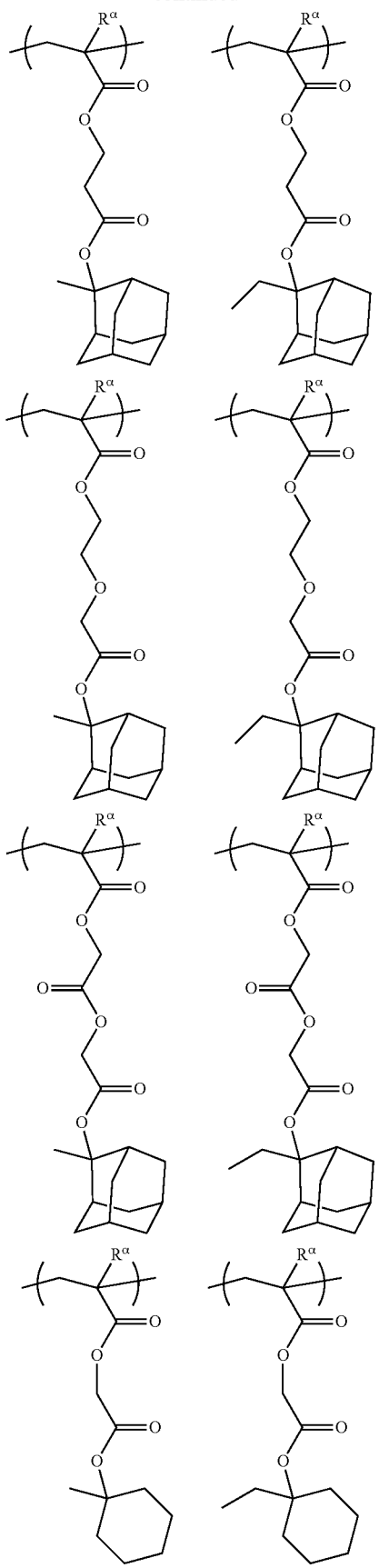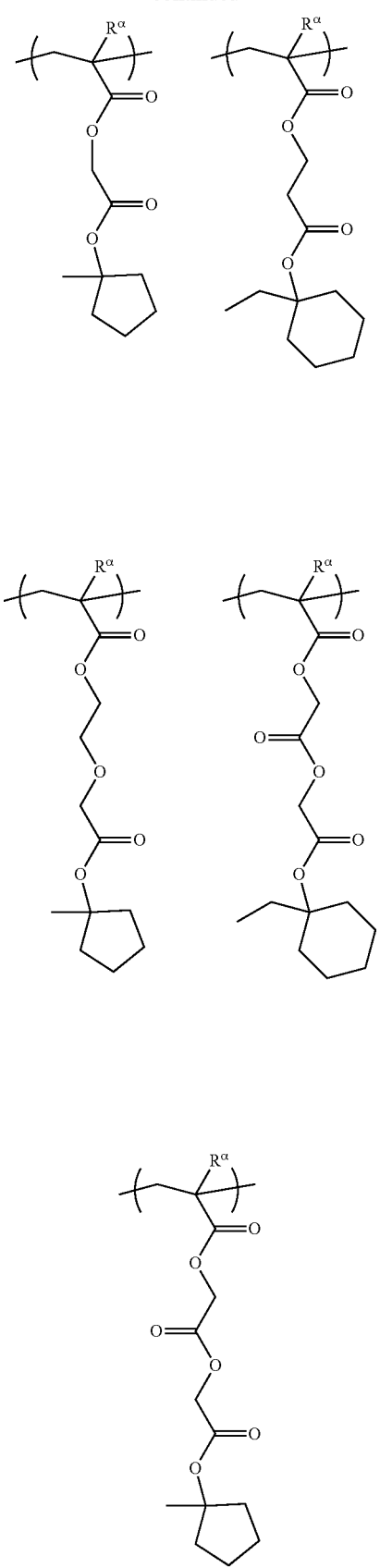

Specific examples of structural unit represented by formula (a1-2) are shown below.

[Chemical Formula 34.]

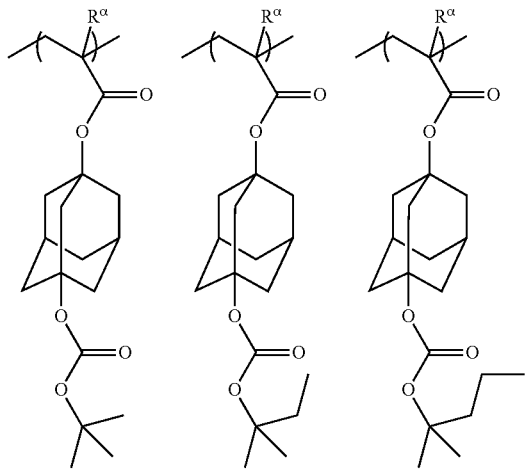
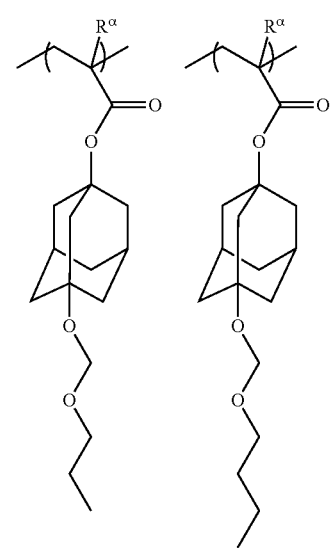
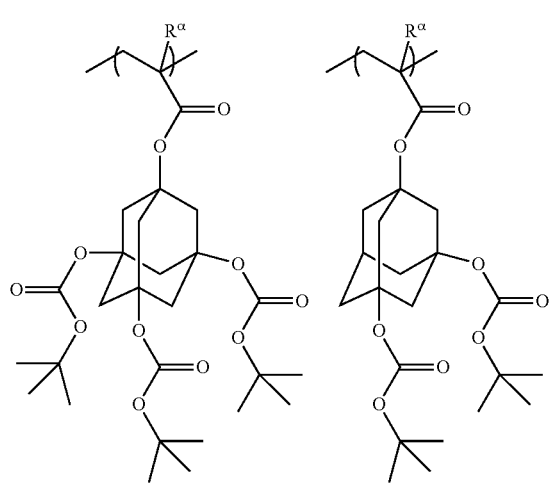
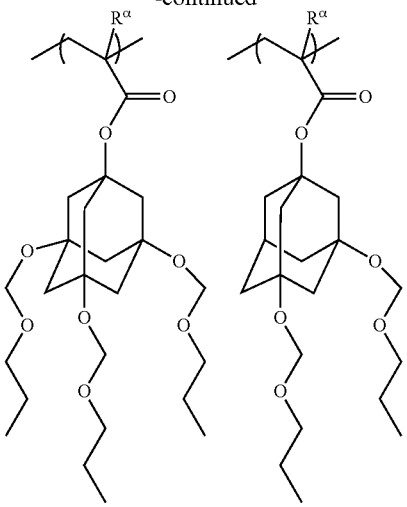

As the structural unit (a1) contained in the component (A1), 1 type of structural unit may be used, or 2 or more types may be used.

From the viewpoint that the properties of the lithography (sensitivity, shape, and the like) by electron beam and EUV are more likely to be enhanced, the structural unit (a1) is further preferably a structural unit represented by general formula (a1-1).

Among these examples, as the structural unit (a1), a structural unit represented by general formula (a1-1-1) is particularly preferable.

[Chemical Formula 35.]

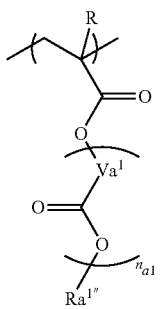

(a1-1-1)

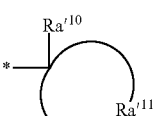

(a1-r2-1)

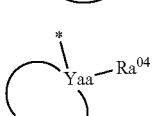

(a1-r2-3)

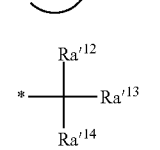

(a1-r2-4)

In the formula, $Ra^{1\prime\prime\prime}$ is an acid dissociable group represented by general formula (a1-r2-1), (a1-r2-3), or (a1-r2-4).

In general formula (a1-1-1), R, $Va^1$ and $n_{a1}$ are the same as defined for R, $Va^1$ and $n_{a1}$ in general formula (a1-1).

The description of the acid dissociable group represented by general formula (a1-r2-1), (a1-r2-3), or (a1-r2-4) is the same as described above.

In the component (A1), the amount of the structural unit (a1) based on the combined total (100 mol %) of all structural units constituting the component (A1) is preferably 5 to 80 mol %, more preferably 10 to 75 mol %, and still more preferably 30 to 70 mol %.

When the amount of the structural unit (a1) is at least as large as the lower limit of the above-mentioned range, various lithography properties such as sensitivity, resolution and roughness may be improved. On the other hand, when the amount of the structural unit (a1) is no more than the upper limit of the above-mentioned range, a good balance may be achieved with the other structural units, and the lithography properties may be improved.

<<Structural Unit (a10) Containing Hydroxystyrene Skeleton>>

The component (A1) preferably has, in addition to the structural unit (a1), a structural unit (a10) containing a hydroxystyrene skeleton.

Preferable examples of the structural unit (a10) include a structural unit represented by general formula (a10-1) shown below.

[Chemical Formula 36.]

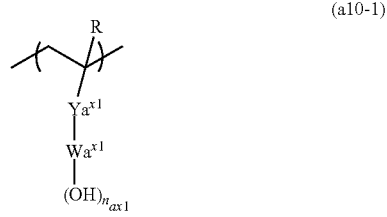

(a10-1)

In the formula, R represents a hydrogen atom, an alkyl group of 1 to 5 carbon atoms or a halogenated alkyl group of 1 to 5 carbon atoms; $Ya^{x1}$ represents a single bond or a divalent linking group; $Wa^{x1}$ represents an aromatic hydrocarbon group having a valency of ($n_{ax1}$+1); and $n_{ax1}$ represents an integer of 1 to 3.

In general formula (a10-1), R represents a hydrogen atom, an alkyl group of 1 to 5 carbon atoms or a halogenated alkyl group of 1 to 5 carbon atoms.

As the alkyl group of 1 to 5 carbon atoms for R, a linear or branched alkyl group of 1 to 5 carbon atoms is preferable, and specific examples thereof include a methyl group, an ethyl group, a propyl group, an isopropyl group, an n-butyl group, an isobutyl group, a tert-butyl group, a pentyl group, an isopentyl group and a neopentyl group. The halogenated alkyl group of 1 to 5 carbon atoms represented by R is a group in which part or all of the hydrogen atoms of the aforementioned alkyl group of 1 to 5 carbon atoms have been substituted with halogen atoms. Examples of the halogen atom include a fluorine atom, a chlorine atom, a bromine atom and an iodine atom, and a fluorine atom is particularly desirable.

As R, a hydrogen atom, an alkyl group of 1 to 5 carbon atoms or a fluorinated alkyl group of 1 to 5 carbon atoms is preferable, and a hydrogen atom or a methyl group is particularly desirable in terms of industrial availability.

In formula (a10-1), $Ya^{x1}$ represents a single bond or a divalent linking group.

Preferable examples of the divalent linking group for $Ya^{x1}$ include a divalent hydrocarbon group which may have a substituent, and a divalent linking group containing a hetero atom.

Divalent Hydrocarbon Group which May have a Substituent:

In the case where $Ya^{x1}$ is a divalent linking group which may have a substituent, the hydrocarbon group may be either an aliphatic hydrocarbon group or an aromatic hydrocarbon group.

Aliphatic Hydrocarbon Group for $Ya^{x1}$

The "aliphatic hydrocarbon group" refers to a hydrocarbon group that has no aromaticity. The aliphatic hydrocarbon group may be saturated or unsaturated. In general, the aliphatic hydrocarbon group is preferably saturated.

Examples of the aliphatic hydrocarbon group include a linear or branched aliphatic hydrocarbon group, and an aliphatic hydrocarbon group containing a ring in the structure thereof can be given.

Linear or Branched Aliphatic Hydrocarbon Group

The linear aliphatic hydrocarbon group preferably has 1 to 10 carbon atoms, more preferably 1 to 6, still more preferably 1 to 4, and most preferably 1 to 3.

As the linear aliphatic hydrocarbon group, a linear alkylene group is preferable. Specific examples thereof include a methylene group [—$CH_2$—], an ethylene group [—$(CH_2)_2$—], a trimethylene group [—$(CH_2)_3$—], a tetramethylene group [—$(CH_2)_4$—] and a pentamethylene group [—$(CH_2)_5$—].

The branched aliphatic hydrocarbon group preferably has 2 to 10 carbon atoms, more preferably 3 to 6, still more preferably 3 or 4, and most preferably 3. As the branched aliphatic hydrocarbon group, branched alkylene groups are preferred, and specific examples include various alkylalkylene groups, including alkylmethylene groups such as —$CH(CH_3)$—, —$CH(CH_2CH_3)$—, —$C(CH_3)_2$—, —$C(CH_3)(CH_2CH_3)$—, —$C(CH_3)(CH_2CH_2CH_3)$—, and —$C(CH_2CH_3)_2$—; alkylethylene groups such as —$CH(CH_3)CH_2$—, —$CH(CH_3)CH(CH_3)$—, —$C(CH_3)_2CH_2$—, —$CH(CH_2CH_3)CH_2$—, and —$C(CH_2CH_3)_2$—$CH_2$—; alkyltrimethylene groups such as —$CH(CH_3)CH_2CH_2$—, and —$CH_2CH(CH_3)CH_2$—; and alkyltetramethylene groups such as —$CH(CH_3)CH_2CH_2CH_2$—, and —$CH_2CH(CH_3)CH_2CH_2$—. As the alkyl group within the alkylalkylene group, a linear alkyl group of 1 to 5 carbon atoms is preferable.

The linear or branched aliphatic hydrocarbon group may or may not have a substituent. Examples of the substituent include a fluorine atom, a fluorinated alkyl group of 1 to 5 carbon atoms, and a carbonyl group.

Aliphatic Hydrocarbon Group Containing a Ring in the Structure Thereof

As examples of the hydrocarbon group containing a ring in the structure thereof, a cyclic aliphatic hydrocarbon group containing a hetero atom in the ring structure thereof and may have a substituent (a group in which two hydrogen atoms have been removed from an aliphatic hydrocarbon ring), a group in which the cyclic aliphatic hydrocarbon group is bonded to the terminal of the aforementioned chain-like aliphatic hydrocarbon group, and a group in which the cyclic aliphatic group is interposed within the aforementioned linear or branched aliphatic hydrocarbon group, can be given. As the linear or branched aliphatic hydrocarbon group, the same groups as those described above can be used.

The cyclic aliphatic hydrocarbon group preferably has 3 to 20 carbon atoms, and more preferably 3 to 12 carbon atoms.

The cyclic aliphatic hydrocarbon group may be either a polycyclic group or a monocyclic group. As the monocyclic aliphatic hydrocarbon group, a group in which 2 hydrogen atoms have been removed from a monocycloalkane is preferable. The monocycloalkane preferably has 3 to 6 carbon atoms, and specific examples thereof include cyclopentane and cyclohexane. As the polycyclic group, a group in which 2 hydrogen atoms have been removed from a polycycloalkane is preferable, and the polycyclic group preferably has 7 to 12 carbon atoms. Examples of the polycycloalkane include adamantane, norbornane, isobornane, tricyclodecane and tetracyclododecane.

The cyclic aliphatic hydrocarbon group may or may not have a substituent. Examples of the substituent include an alkyl group, an alkoxy group, a halogen atom, a halogenated alkyl group, a hydroxyl group and a carbonyl group.

The alkyl group as the substituent is preferably an alkyl group of 1 to 5 carbon atoms, and a methyl group, an ethyl group, a propyl group, an n-butyl group or a tert-butyl group is particularly desirable.

The alkoxy group as the substituent is preferably an alkoxy group having 1 to 5 carbon atoms, more preferably a methoxy group, ethoxy group, n-propoxy group, iso-propoxy group, n-butoxy group or tert-butoxy group, and most preferably a methoxy group or an ethoxy group.

Examples of the halogen atom for the substituent include a fluorine atom, a chlorine atom, a bromine atom and an iodine atom, and a fluorine atom is preferable.

Examples of the halogenated alkyl group for the substituent include groups in which part or all of the hydrogen atoms within the aforementioned alkyl groups has been substituted with the aforementioned halogen atoms.

The cyclic aliphatic hydrocarbon group may have part of the carbon atoms constituting the ring structure thereof substituted with a substituent containing a hetero atom. As the substituent containing a hetero atom, —O—, —C(=O)—O—, —S—, —S(=O)$_2$— or —S(=O)$_2$—O— is preferable.

Aromatic Hydrocarbon Group for Ya$^{x1}$

The aromatic hydrocarbon group is a hydrocarbon group having at least one aromatic ring.

The aromatic ring is not particularly limited, as long as it is a cyclic conjugated compound having $(4n+2)\pi$ electrons, and may be either monocyclic or polycyclic. The aromatic ring preferably has 5 to 30 carbon atoms, more preferably 5 to 20 carbon atoms, and still more preferably 6 to 15 carbon atoms, and most preferably 6 to 12 carbon atoms. Here, the number of carbon atoms within a substituent(s) is not included in the number of carbon atoms of the aromatic hydrocarbon group. Examples of the aromatic ring include aromatic hydrocarbon rings, such as benzene, naphthalene, anthracene and phenanthrene; and aromatic hetero rings in which part of the carbon atoms constituting the aforementioned aromatic hydrocarbon rings has been substituted with a hetero atom. Examples of the hetero atom within the aromatic hetero rings include an oxygen atom, a sulfur atom and a nitrogen atom. Specific examples of the aromatic hetero ring include a pyridine ring and a thiophene ring.

Specific examples of the aromatic hydrocarbon group include a group in which two hydrogen atoms have been removed from the aforementioned aromatic hydrocarbon ring or aromatic hetero ring (arylene group or heteroarylene group); a group in which two hydrogen atoms have been removed from an aromatic compound having two or more aromatic rings (biphenyl, fluorene or the like); and a group in which one hydrogen atom of the aforementioned aromatic hydrocarbon ring or aromatic hetero ring has been substituted with an alkylene group (a group in which one hydrogen atom has been removed from the aryl group within the aforementioned arylalkyl group such as a benzyl group, a phenethyl group, a 1-naphthylmethyl group, a 2-naphthylmethyl group, a 1-naphthylethyl group, or a 2-naphthylethyl group, or a heteroarylalkyl group). The alkylene group which is bonded to the aforementioned aryl group or heteroaryl group preferably has 1 to 4 carbon atoms, more preferably 1 or 2 carbon atoms, and most preferably 1 carbon atom.

With respect to the aromatic hydrocarbon group, the hydrogen atom within the aromatic hydrocarbon group may be substituted with a substituent. For example, the hydrogen atom bonded to the aromatic ring within the aromatic hydrocarbon group may be substituted with a substituent. Examples of substituents include an alkyl group, an alkoxy group, a halogen atom, a halogenated alkyl group, and a hydroxyl group.

The alkyl group as the substituent is preferably an alkyl group of 1 to 5 carbon atoms, and a methyl group, an ethyl group, a propyl group, an n-butyl group or a tert-butyl group is particularly desirable.

As the alkoxy group, the halogen atom and the halogenated alkyl group for the substituent, the same groups as the aforementioned substituent groups for substituting a hydrogen atom within the cyclic aliphatic hydrocarbon group can be used.

Divalent Linking Group Containing a Hetero Atom

In the case where Ya$^{x1}$ represents a divalent linking group containing a hetero atom, preferable examples of the linking group include —O—, —C(=O)—O—, —C(=O)—, —O—C(=O)—O—, —C(=O)—NH—, —NH—, -NH—C(=NH)— (may be substituted with a substituent such as an alkyl group, an acyl group or the like), —S—, —S(=O)$_2$—, —S(=O)$_2$—O—, and a group represented by general formula: —Y$^{21}$—O—Y$^{22}$—, —Y$^{21}$—O—, —Y$^{21}$—C(=O)—O—, —C(=O)—O—Y$^{21}$—[Y$^{21}$—C(=O)—O]$_{m''}$—Y$^{22}$—, —Y$^{21}$—O—C(=O)—Y$^{22}$— or —Y$^{21}$—S(=O)$_2$—O—Y$^{22}$— [in the formulae, Y$^{21}$ and Y$^{22}$ each independently represents a divalent hydrocarbon group which may have a substituent, 0 represents an oxygen atom, and m' represents an integer of 0 to 3].

In the case where the divalent linking group containing a hetero atom is —C(=O)—NH—, —C(=O)—NH—C(=O)—, —NH— or -NH—C(=NH)—, H may be substituted with a substituent such as an alkyl group, an acyl group or the like. The substituent (an alkyl group, an acyl group or the like) preferably has 1 to 10 carbon atoms, more preferably 1 to 8, and most preferably 1 to 5.

In general formulae —Y$^{21}$—Y$^{22}$—Y$^{21}$—, —Y$^{21}$—C(=O)—O—, —C(=O)—O—Y$^{21}$—[Y$^{21}$—C(=O)—O]$_{m''}$—Y$^{22}$—, —Y$^{21}$—C(=O)—Y$^{22}$— or —Y$^{21}$—S(=O)$_2$—O—Y$^{22}$—, Y$^{21}$ and Y$^{22}$ each independently represents a divalent hydrocarbon group which may have a substituent. Examples of the divalent hydrocarbon group include the same groups as those described above as the "divalent hydrocarbon group which may have a substituent" in the explanation of the aforementioned divalent linking group.

As Y$^{21}$, a linear aliphatic hydrocarbon group is preferable, more preferably a linear alkylene group, still more preferably a linear alkylene group of 1 to 5 carbon atoms, and a methylene group or an ethylene group is particularly desirable.

As $Y^{22}$, a linear or branched aliphatic hydrocarbon group is preferable, and a methylene group, an ethylene group or an alkylmethylene group is more preferable. The alkyl group within the alkylmethylene group is preferably a linear alkyl group of 1 to 5 carbon atoms, more preferably a linear alkyl group of 1 to 3 carbon atoms, and most preferably a methyl group.

In the group represented by the formula —[$Y^{21}$—C(=O)—O]$_{m''}$—$Y^{22}$—, m" represents an integer of 0 to 3, preferably an integer of 0 to 2, more preferably 0 or 1, and most preferably 1. Namely, it is particularly desirable that the group represented by the formula —[$Y^{21}$—C(=O)—O]$_{m''}$—$Y^{22}$— is a group represented by the formula —$Y^{21}$—C(=O)—O—$Y^{22}$—. Among these, a group represented by the formula —(CH$_2$)$_{a'}$—C(=O)—O—(CH$_2$)$_{b'}$— is preferable. In the formula, a' is an integer of 1 to 10, preferably an integer of 1 to 8, more preferably an integer of 1 to 5, still more preferably 1 or 2, and most preferably 1. b' is an integer of 1 to 10, preferably an integer of 1 to 8, more preferably an integer of 1 to 5, still more preferably 1 or 2, and most preferably 1.

$Ya^{x1}$ preferably represents an ester bond [—C(=O)—O—], an ether bond (—O—), —C(=O)—NH—, a linear or branched alkylene group, a combination of these, or a single bond, and more preferably a single bond.

In formula (a10-1), $Wa^{x1}$ represents an aromatic hydrocarbon group having a valency of ($n_{ax1}$+1).

Examples of the aromatic hydrocarbon group for $Wa^{x1}$ include a group obtained by removing ($n_{ax1}$+1) hydrogen atoms from an aromatic ring. The aromatic ring is not particularly limited, as long as it is a cyclic conjugated compound having (4n+2)π electrons, and may be either monocyclic or polycyclic. The aromatic ring preferably has 5 to 30 carbon atoms, more preferably 5 to 20 carbon atoms, and still more preferably 6 to 15 carbon atoms, and most preferably 6 to 12 carbon atoms. Examples of the aromatic ring include aromatic hydrocarbon rings, such as benzene, naphthalene, anthracene and phenanthrene; and aromatic hetero rings in which part of the carbon atoms constituting the aforementioned aromatic hydrocarbon rings has been substituted with a hetero atom. Examples of the hetero atom within the aromatic hetero rings include an oxygen atom, a sulfur atom and a nitrogen atom. Specific examples of the aromatic hetero ring include a pyridine ring and a thiophene ring.

In formula (a10-1), $n_{ax1}$ is an integer of 1 to 3, preferably 1 or 2, and more preferably 1.

Specific examples of the structural unit represented by general formula (a10-1) are shown below.

In the following formulae, $R^\alpha$ represents a hydrogen atom, a methyl group or a trifluoromethyl group.

[Chemical Formula 37.]

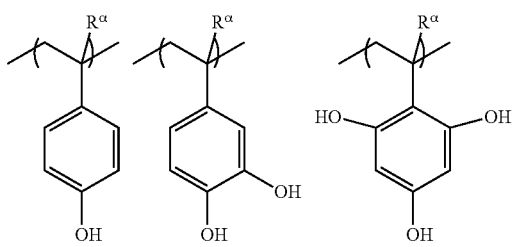

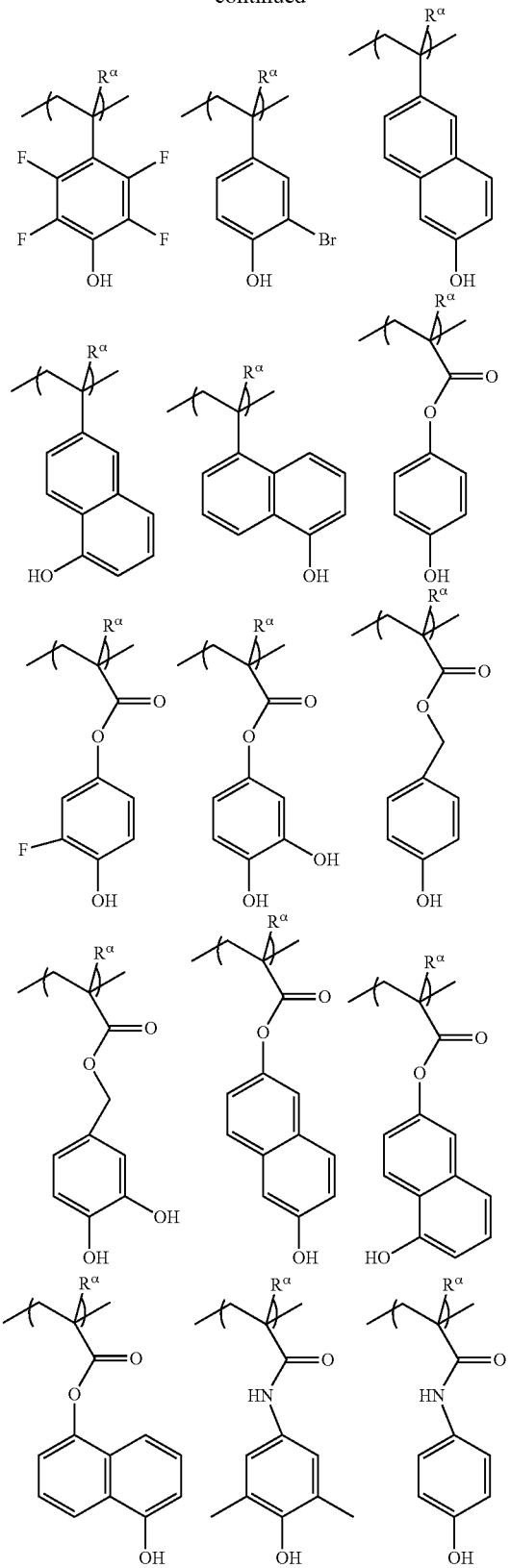

As the structural unit (a10) contained in the component (A1), 1 kind of structural unit may be used, or 2 or more kinds may be used.

In the component (A1), the amount of the structural unit (a10) based on the combined total (100 mol %) of all structural units constituting the component (A1) is, for example, 0 to 80 mol %, preferably 10 to 80 mol %, more preferably 20 to 70 mol %, and still more preferably 30 to 60 mol %.

When the amount of the structural unit (a10) is at least as large as the lower limit of the above-mentioned preferable range, various lithography properties such as sensitivity, resolution and roughness may be improved. On the other hand, when the amount of the structural unit (a10) is no more than the upper limit of the above-mentioned range, a good balance may be achieved with the other structural units, and the lithography properties may be improved.

<<Structural Unit (a2)>>

The component (A1) preferably has, in addition to the structural unit (a1), a structural unit (a2) containing a lactone-containing cyclic group, an —SO$_2$— containing cyclic group or a carbonate-containing cyclic group (provided that structural units which fall under the definition of the structural unit (a1) are excluded).

When the component (A1) is used for forming a resist film, the lactone-containing cyclic group, the —SO$_2$— containing cyclic group or the carbonate-containing cyclic group within the structural unit (a2) is effective in improving the adhesion between the resist film and the substrate. In addition, by virtue of containing the structural unit (a2), for example, the acid diffusion length is appropriately adjusted, the adhesion of the resist film to the substrate is enhanced, or the solubility during development is appropriately adjusted. As a result, the lithography properties may be enhanced.

The term "lactone-containing cyclic group" refers to a cyclic group including a ring containing a —O—C(=O)— structure (lactone ring). The term "lactone ring" refers to a single ring containing a —O—C(O)— structure, and this ring is counted as the first ring. A lactone-containing cyclic group in which the only ring structure is the lactone ring is referred to as a monocyclic group, and groups containing other ring structures are described as polycyclic groups regardless of the structure of the other rings. The lactone-containing cyclic group may be either a monocyclic group or a polycyclic group.

The lactone-containing cyclic group for the structural unit (a2) is not particularly limited, and an arbitrary structural unit may be used. Specific examples include groups represented by general formulae (a2-r-1) to (a2-r-7) shown below.

[Chemical Formula 38.]

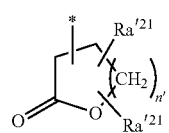
(a2-r-1)

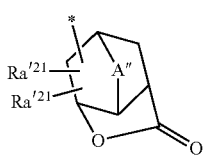
(a2-r-2)

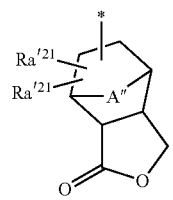
(a2-r-3)

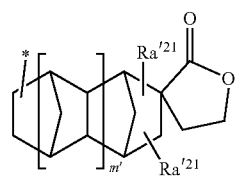
(a2-r-4)

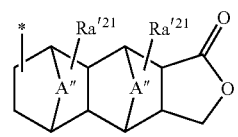
(a2-r-5)

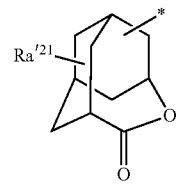
(a2-r-6)

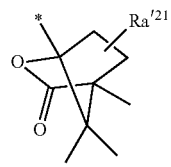
(a2-r-7)

In the formulae, each Ra'$^{21}$ independently represents a hydrogen atom, an alkyl group, an alkoxy group, a halogen atom, a halogenated alkyl group, a hydroxy group, —COOR", —OC(=O)R", a hydroxyalkyl group or a cyano group; R" represents a hydrogen atom, an alkyl group, a lactone-containing cyclic group, a carbonate-containing cyclic group or an —SO$_2$— containing cyclic group; A" represents an oxygen atom (—O—), a sulfur atom (—S—) or an alkylene group of 1 to 5 carbon atoms which may contain an oxygen atom or a sulfur atom; n' represents an integer of 0 to 2; and m' represents 0 or 1.

In formulae (a2-r-1) to (a2-r-7), the alkyl group for Ra'$^{21}$ is preferably an alkyl group of 1 to 6 carbon atoms. Further, the alkyl group is preferably a linear alkyl group or a branched alkyl group. Specific examples include a methyl group, an ethyl group, a propyl group, an isopropyl group, an n-butyl group, an isobutyl group, a tert-butyl group, a pentyl group, an isopentyl group, a neopentyl group and a hexyl group. Among these, a methyl group or ethyl group is preferable, and a methyl group is particularly desirable.

The alkoxy group for Ra'$^{21}$ is preferably an alkoxy group of 1 to 6 carbon atoms.

Further, the alkoxy group is preferably a linear or branched alkoxy group. Specific examples of the alkoxy groups include the aforementioned alkyl groups for Ra'$^{21}$ having an oxygen atom (—O—) bonded thereto.

As examples of the halogen atom for Ra'$^{21}$, a fluorine atom, chlorine atom, bromine atom and iodine atom can be given. Among these, a fluorine atom is preferable.

Examples of the halogenated alkyl group for Ra'²¹ include groups in which part or all of the hydrogen atoms within the aforementioned alkyl group for Ra'²¹ has been substituted with the aforementioned halogen atoms. As the halogenated alkyl group, a fluorinated alkyl group is preferable, and a perfluoroalkyl group is particularly desirable.

With respect to —COOR" and —OC(═O)R" for Ra'²¹, R" represents a hydrogen atom, an alkyl group, a lactone-containing cyclic group, a carbonate-containing cyclic group or an —SO₂— containing cyclic group.

The alkyl group for R" may be linear, branched or cyclic, and preferably has 1 to 15 carbon atoms.

When R" represents a linear or branched alkyl group, it is preferably an alkyl group of 1 to 10 carbon atoms, more preferably an alkyl group of 1 to 5 carbon atoms, and most preferably a methyl group or an ethyl group.

When R" is a cyclic alkyl group (cycloalkyl group), it preferably has 3 to 15 carbon atoms, more preferably 4 to 12 carbon atoms, and most preferably 5 to 10 carbon atoms. Specific examples include groups in which one or more hydrogen atoms have been removed from a monocycloalkane or a polycycloalkane such as a bicycloalkane, tricycloalkane or tetracycloalkane which may or may not be substituted with a fluorine atom or a fluorinated alkyl group. Specific examples include groups in which one or more hydrogen atoms have been removed from a monocycloalkane such as cyclopentane or cyclohexane; and groups in which one or more hydrogen atoms have been removed from a polycycloalkane such as adamantane, norbornane, isobornane, tricyclodecane or tetracyclododecane.

Examples of the lactone-containing cyclic group for R" include groups represented by the aforementioned general formulae (a2-r-1) to (a2-r-7). The carbonate-containing cyclic group for R" is the same as defined for the carbonate-containing cyclic group described later. Specific examples of the carbonate-containing cyclic group include groups represented by general formulae (ax3-r-1) to (ax3-r-3).

The —SO₂— containing cyclic group for R" is the same as defined for the —SO₂— containing cyclic group described later. Specific examples of the —SO₂— containing cyclic group include groups represented by general formulae (a5-r-1) to (a5-r-4).

The hydroxyalkyl group for Ra'²¹ preferably has 1 to 6 carbon atoms, and specific examples thereof include the alkyl groups for Ra'²¹ in which at least one hydrogen atom has been substituted with a hydroxy group.

In formulae (a2-r-2), (a2-r-3) and (a2-r-5), as the alkylene group of 1 to 5 carbon atoms represented by A", a linear or branched alkylene group is preferable, and examples thereof include a methylene group, an ethylene group, an n-propylene group and an isopropylene group. Examples of alkylene groups that contain an oxygen atom or a sulfur atom include the aforementioned alkylene groups in which —O— or —S— is bonded to the terminal of the alkylene group or present between the carbon atoms of the alkylene group. Specific examples of such alkylene groups include —O—CH₂—, —CH₂—O—CH₂—, —S—CH₂— and —CH₂—S—CH₂—. As A", an alkylene group of 1 to 5 carbon atoms or —O— is preferable, more preferably an alkylene group of 1 to 5 carbon atoms, and most preferably a methylene group.

Specific examples of the groups represented by the aforementioned general formulae (a2-r-1) to (a2-r-7) are shown below.

[Chemical Formula 39.]

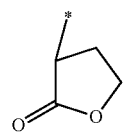 (r-Ic-1-1)

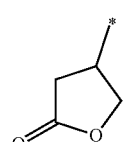 (r-Ic-1-2)

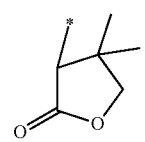 (r-Ic-1-3)

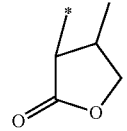 (r-Ic-1-4)

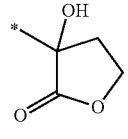 (r-Ic-1-5)

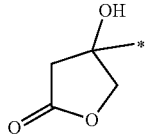 (r-Ic-1-6)

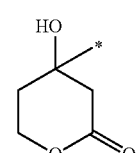 (r-Ic-1-7)

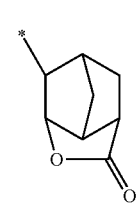 (r-Ic-2-1)

 (r-Ic-2-2)

(r-Ic-2-3)
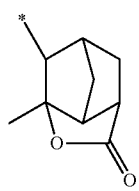
(r-Ic-2-4)
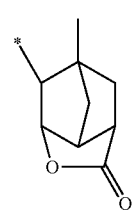
(r-Ic-2-5)
(r-Ic-2-6)
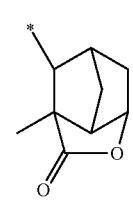
(r-Ic-2-7)
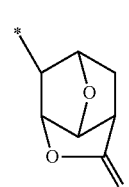
(r-Ic-2-8)
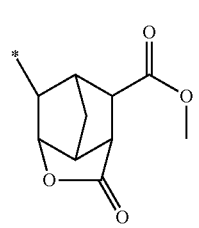
(r-Ic-2-9)
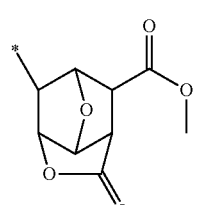
(r-Ic-2-10)
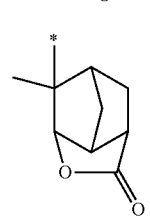
(r-Ic-2-11)
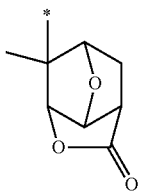
(r-Ic-2-12)
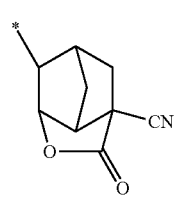
(r-Ic-2-13)
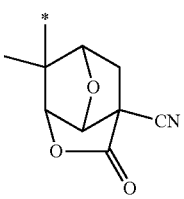
(r-Ic-2-14)
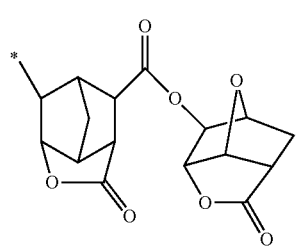
(r-Ic-2-15)
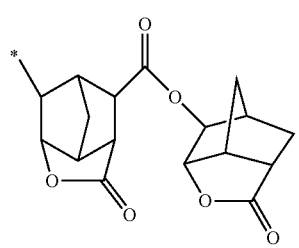
(r-Ic-2-16)
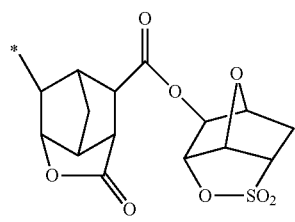
(r-Ic-2-17)
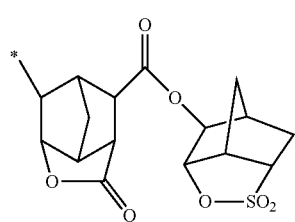

(r-Ic-2-18)
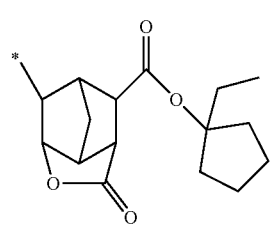
(r-Ic-3-1)
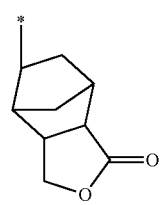
(r-Ic-3-2)
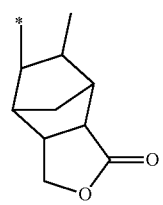
(r-Ic-3-3)
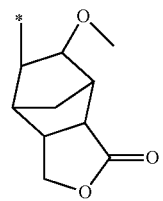
(r-Ic-3-4)
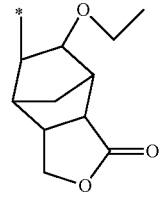
(r-Ic-3-5)
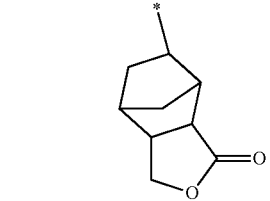
[Chemical Formula 40.]
(r-Ic-4-1)
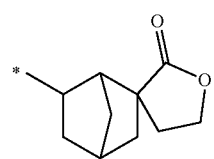
(r-Ic-4-2)
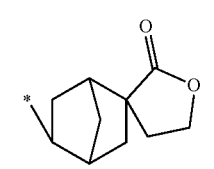
(r-Ic-4-3)
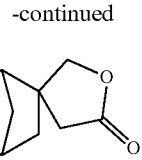
(r-Ic-4-4)
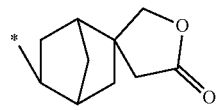
(r-Ic-4-5)
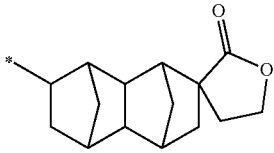
(r-Ic-4-6)
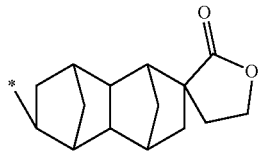
(r-Ic-4-7)
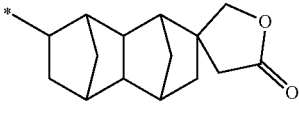
(r-Ic-4-8)
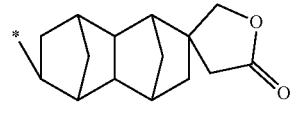
(r-Ic-4-9)
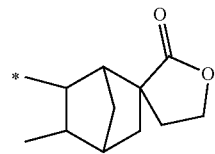
(r-Ic-5-1)
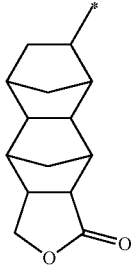
(r-Ic-5-2)
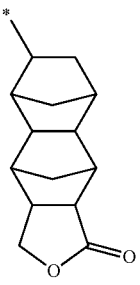

-continued (r-Ic-5-3)
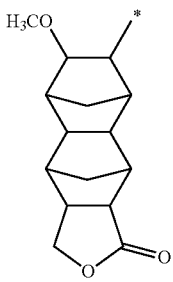

(r-Ic-5-4)
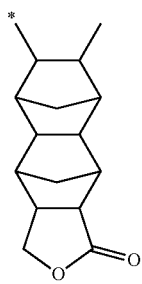

(r-Ic-6-1)
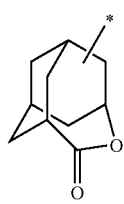

(r-Ic-7-1)
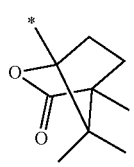

An "—$SO_2$— containing cyclic group" refers to a cyclic group having a ring containing —$SO_2$— within the ring structure thereof, i.e., a cyclic group in which the sulfur atom (S) within —$SO_2$— forms part of the ring skeleton of the cyclic group. The ring containing —$SO_2$— within the ring skeleton thereof is counted as the first ring. A cyclic group in which the only ring structure is the ring that contains —$SO_2$— in the ring skeleton thereof is referred to as a monocyclic group, and a group containing other ring structures is described as a polycyclic group regardless of the structure of the other rings. The —$SO_2$— containing cyclic group may be either a monocyclic group or a polycyclic group.

As the —$SO_2$— containing cyclic group, a cyclic group containing —O—$SO_2$— within the ring skeleton thereof, i.e., a cyclic group containing a sultone ring in which —O—S— within the —O—$SO_2$— group forms part of the ring skeleton thereof is particularly desirable.

More specific examples of the —$SO_2$— containing cyclic group include groups represented by general formulas (a5-r-1) to (a5-r-4) shown below.

[Chemical Formula 41.]

(a5-r-1)
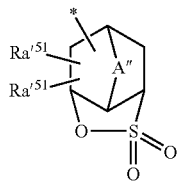

(a5-r-2)
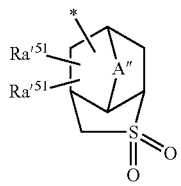

(a5-r-3)
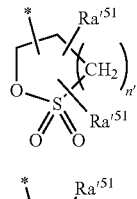

(a5-r-4)
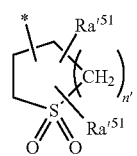

In the formulae, each $Ra'^{51}$ independently represents a hydrogen atom, an alkyl group, an alkoxy group, a halogen atom, a halogenated alkyl group, a hydroxy group, —COOR", —OC(=O)R", a hydroxyalkyl group or a cyano group; R" represents a hydrogen atom, an alkyl group, a lactone-containing cyclic group, a carbonate-containing cyclic group or an —$SO_2$— containing cyclic group; A" represents an oxygen atom, a sulfur atom or an alkylene group of 1 to 5 carbon atoms which may contain an oxygen atom or a sulfur atom; and n' represents an integer of 0 to 2.

In general formulae (a5-r-1) and (a5-r-2), A" is the same as defined for A" in general formulae (a2-r-2), (a2-r-3) and (a2-r-5).

Examples of the alkyl group, alkoxy group, halogen atom, halogenated alkyl group, —COOR", —OC(=O)R" and hydroxyalkyl group for $Ra'^{S1}$ include the same groups as those described above in the explanation of $Ra'^{21}$ in the general formulas (a2-r-1) to (a2-r-7).

Specific examples of the groups represented by the aforementioned general formulae (a5-r-1) to (a5-r-4) are shown below. In the formulae shown below, "Ac" represents an acetyl group.

[Chemical Formula 42.]

(r-sl-1-1)
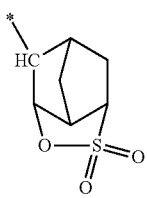

(r-sl-1-2)
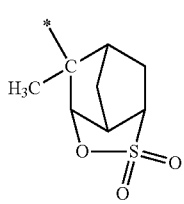
(r-sl-1-3)
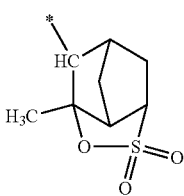
(r-sl-1-4)
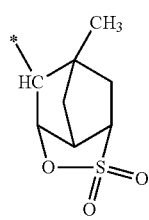
(r-sl-1-5)
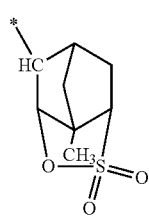
(r-sl-1-6)
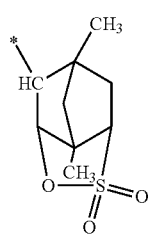
(r-sl-1-7)
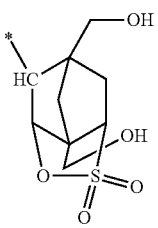
(r-sl-1-8)
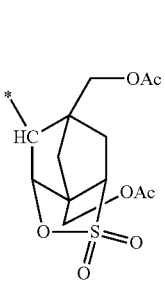
(r-sl-1-9)
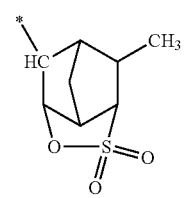
(r-sl-1-10)
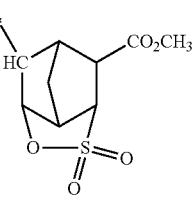
(r-sl-1-11)
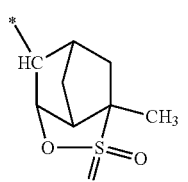
(r-sl-1-12)
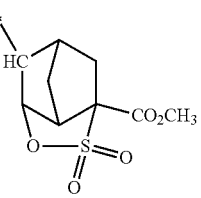
(r-sl-1-13)
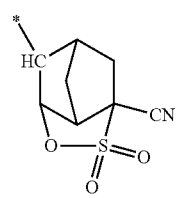
(r-sl-1-14)
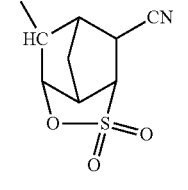
(r-sl-1-15)
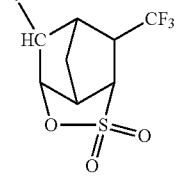
(r-sl-1-16)

-continued
(r-sl-1-17)
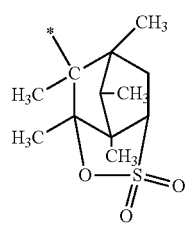
(r-sl-1-18)
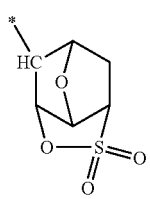
(r-sl-1-19)
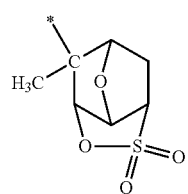
(r-sl-1-20)
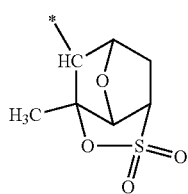
(r-sl-1-21)
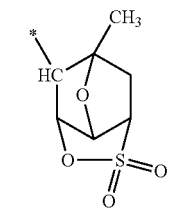
[Chemical Formula 43.]
(r-sl-1-22)
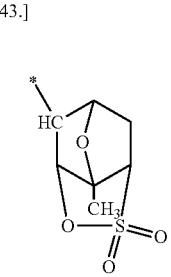
(r-sl-23)
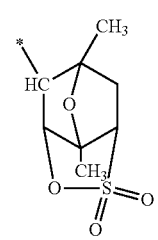
-continued
(r-sl-1-24)
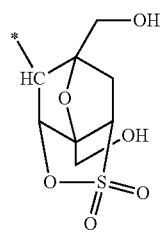
(r-sl-1-25)
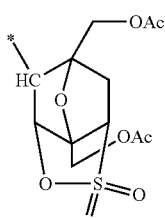
(r-sl-1-26)
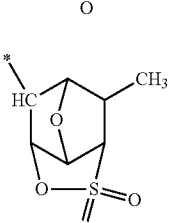
(r-sl-1-27)
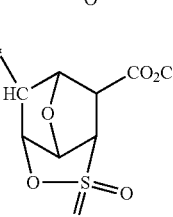
(r-sl-1-28)
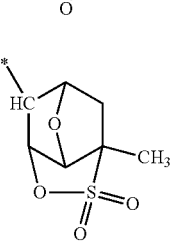
(r-sl-1-29)
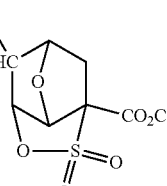
(r-sl-1-30)
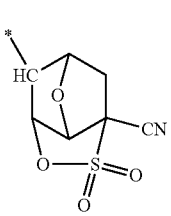

-continued (r-sl-1-31)
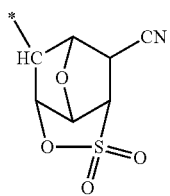

(r-sl-1-32)
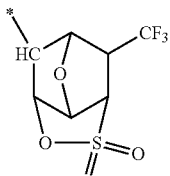

(r-sl-1-33)
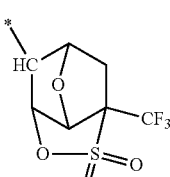

[Chemical Formula 44.]

(r-sl-2-1)
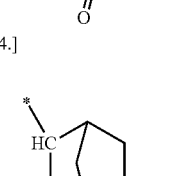

(r-sl-2-2)
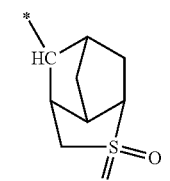

(r-sl-3-1)
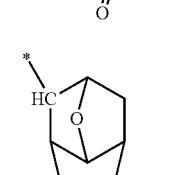

(r-sl-4-1)
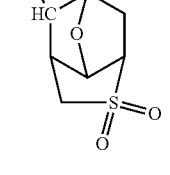

The term "carbonate-containing cyclic group" refers to a cyclic group including a ring containing a —O—C(=O)—O— structure (carbonate ring). The term "carbonate ring" refers to a single ring containing a —O—C(=O)—O— structure, and this ring is counted as the first ring. A carbonate-containing cyclic group in which the only ring structure is the carbonate ring is referred to as a monocyclic group, and groups containing other ring structures are described as polycyclic groups regardless of the structure of the other rings. The carbonate-containing cyclic group may be either a monocyclic group or a polycyclic group.

The carbonate-containing cyclic group is not particularly limited, and an arbitrary group may be used. Specific examples include groups represented by general formulae (ax3-r-1) to (ax3-r-3) shown below.

[Chemical Formula 45.]

(ax3-r-1)
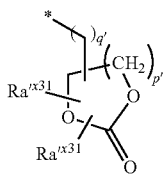

(ax3-r-2)
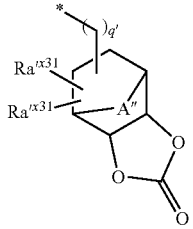

(ax3-r-3)
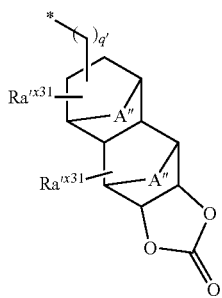

In the formulae, each $Ra'^{x31}$ independently represents a hydrogen atom, an alkyl group, an alkoxy group, a halogen atom, a halogenated alkyl group, a hydroxy group, —COOR", —OC(=O)R", a hydroxyalkyl group or a cyano group; R" represents a hydrogen atom, an alkyl group, a lactone-containing cyclic group, a carbonate-containing cyclic group or an —SO$_2$— containing cyclic group; A" represents an oxygen atom, a sulfur atom or an alkylene group of 1 to 5 carbon atoms which may contain an oxygen atom or a sulfur atom; p' represents an integer of 0 to 3; and q' represents 0 or 1.

In general formulae (ax3-r-2) and (ax3-r-3), A" is the same as defined for A" in general formulae (a2-r-2), (a2-r-3) and (a2-r-5).

Examples of the alkyl group, alkoxy group, halogen atom, halogenated alkyl group, —COOR", —OC(=O)R" and hydroxyalkyl group for $Ra'^{31}$ include the same groups as those described above in the explanation of $Ra'^{21}$ in the general formulas (a2-r-1) to (a2-r-7).

Specific examples of the groups represented by the aforementioned general formulae (ax3-r-1) to (ax3-r-3) are shown below.

[Chemical Formula 46.]
(r-cr-1-1)
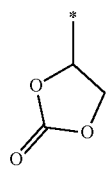
(r-cr-1-2)
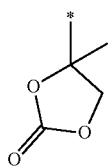
(r-cr-1-3)
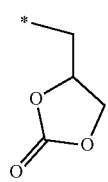
(r-cr-1-4)
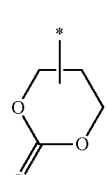
(r-cr-1-5)
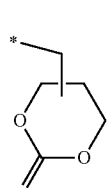
(r-cr-1-6)
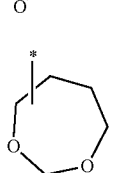
(r-cr-1-7)
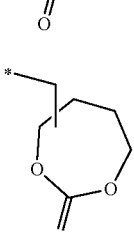
(r-cr-2-1)
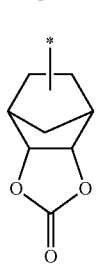
(r-cr-2-2)
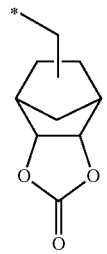
(r-cr-2-3)
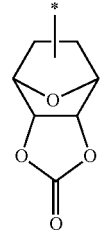
(r-cr-2-4)
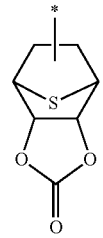
(r-cr-3-1)
(r-cr-3-2)

-continued (r-cr-3-3)
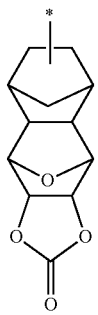

(r-cr-3-4)
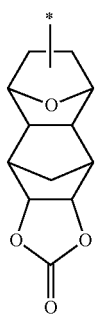

(r-cr-3-5)
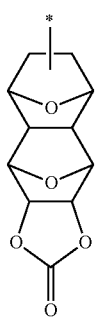

As the structural unit (a2), a structural unit derived from an acrylate ester which may have the hydrogen atom bonded to the carbon atom on the α-position substituted with a substituent is preferable.

The structural unit (a2) is preferably a structural unit represented by general formula (a2-1) shown below.

[Chemical Formula 47.]

(a2-1)
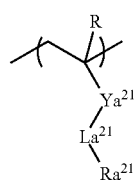

In the formula, R represents a hydrogen atom, an alkyl group of 1 to 5 carbon atoms or a halogenated alkyl group of 1 to 5 carbon atoms; $Ya^{21}$ represents a single bond or a divalent linking group; $La^{21}$ represents —O—, —COO—, —CON(R')—, —OCO—, —CONHCO— or —CONHCS—; and R' represents a hydrogen atom or a methyl group; provided that, when $La^{21}$ represents —O—, $Ya^{21}$ does not represents —CO—; and $Ra^{21}$ represents a lactone-containing cyclic group, a carbonate-containing cyclic group or an —$SO_2$— containing cyclic group.

In the formula (a2-1), R is the same as defined above. As R, a hydrogen atom, an alkyl group of 1 to 5 carbon atoms or a fluorinated alkyl group of 1 to 5 carbon atoms is preferable, and a hydrogen atom or a methyl group is particularly desirable in terms of industrial availability.

In the formula (a2-1), the divalent linking group for $Ya^{21}$ is not particularly limited, and preferable examples thereof include a divalent hydrocarbon group which may have a substituent and a divalent linking group containing a hetero atom. The divalent hydrocarbon group which may have a substituent and the divalent linking group containing a hetero atom for $Ya^{21}$ are the same as defined for the divalent hydrocarbon group which may have a substituent and the divalent linking group containing a hetero atom described above in relation to $Ya^x$ in general formula (a10-1).

$Ya^{21}$ preferably represents an ester bond [—C(=O)—O—], an ether bond (—O—), a linear or branched alkylene group, a combination of these, or a single bond.

In the formula (a2-1), $Ra^{21}$ represents a lactone-containing cyclic group, an —$SO_2$— containing cyclic group or a carbonate-containing cyclic group.

Preferable examples of the lactone-containing cyclic group, the —$SO_2$— containing cyclic group and the carbonate-containing cyclic group for $Ra^{21}$ include groups represented by general formulae (a2-r-1) to (a2-r-7), groups represented by general formulae (a5-r-1) to (a5-r-4) and groups represented by general formulae (ax3-r-1) to (ax3-r-3).

Among the above examples, a lactone-containing cyclic group or a —$SO_2$— containing cyclic group is preferable, and a group represented by general formula (a2-r-1), (a2-r-2), (a2-r-6) or (a5-r-1) is more preferable. Specifically, a group represented by any of chemical formulae (r-1c-1-1) to (r-1c-1-7), (r-1c-2-1) to (r-1c-2-18), (r-1c-6-1), (r-s1-1-1) and (r-s1-1-18) is still more preferable.

As the structural unit (a2) contained in the component (A1), 1 kind of structural unit may be used, or 2 or more kinds may be used.

When the component (A1) contains the structural unit (a2), the amount of the structural unit (a2) based on the combined total (100 mol %) of all structural units constituting the component (A1) is preferably 1 to 50 mol %, more preferably 5 to 45 mol %, still more preferably 10 to 40 mol %, and most preferably 10 to 30 mol %.

When the amount of the structural unit (a2) is at least as large as the lower limit of the above preferable range, the effect of using the structural unit (a2) can be satisfactorily achieved. On the other hand, when the amount of the structural unit (a2) is no more than the upper limit of the above preferable range, a good balance can be achieved with the other structural units, and various lithography properties and pattern shape can be improved.

<<Structural Unit (a3)>>

The component (A1) may have, in addition to the structural unit (a1), a structural unit (a3) containing a polar group-containing aliphatic hydrocarbon group (provided that the structural units that fall under the definition of structural units (a1) and (a2) are excluded). When the component (A1) includes the structural unit (a3), the hydrophilicity of the component (A1) is enhanced, thereby contributing to improvement in resolution.

Examples of the polar group include a hydroxyl group, cyano group, carboxyl group, or hydroxyalkyl group in which part of the hydrogen atoms of the alkyl group have been substituted with fluorine atoms, although a hydroxyl group is particularly desirable.

Examples of the aliphatic hydrocarbon group include linear or branched hydrocarbon groups (preferably alkylene groups) of 1 to 10 carbon atoms, and cyclic aliphatic hydrocarbon groups (cyclic groups). These cyclic groups can be selected appropriately from the multitude of groups that have been proposed for the resins of resist compositions designed for use with ArF excimer lasers. The cyclic group is preferably a polycyclic group, more preferably a polycyclic group of 7 to 30 carbon atoms.

Of the various possibilities, structural units derived from an acrylate ester that include an aliphatic polycyclic group that contains a hydroxyl group, cyano group, carboxyl group or a hydroxyalkyl group in which part of the hydrogen atoms of the alkyl group have been substituted with fluorine atoms are particularly desirable. Examples of the polycyclic group include groups in which two or more hydrogen atoms have been removed from a bicycloalkane, tricycloalkane, tetracycloalkane or the like. Specific examples include groups in which two or more hydrogen atoms have been removed from a polycycloalkane such as adamantane, norbornane, isobornane, tricyclodecane or tetracyclododecane. Of these polycyclic groups, groups in which two or more hydrogen atoms have been removed from adamantane, norbornane or tetracyclododecane are preferred industrially.

As the structural unit (a3), there is no particular limitation as long as it is a structural unit containing a polar group-containing aliphatic hydrocarbon group, and an arbitrary structural unit may be used.

The structural unit (a3) is preferably a structural unit derived from an acrylate ester which may have the hydrogen atom bonded to the carbon atom on the α-position substituted with a substituent and contains a polar group-containing aliphatic hydrocarbon group.

When the aliphatic hydrocarbon group within the polar group-containing aliphatic hydrocarbon group is a linear or branched hydrocarbon group of 1 to 10 carbon atoms, the structural unit (a3) is preferably a structural unit derived from a hydroxyethyl ester of acrylic acid.

On the other hand, in the structural unit (a3), when the hydrocarbon group within the polar group-containing aliphatic hydrocarbon group is a polycyclic group, structural units represented by formulas (a3-1), (a3-2), and (a3-3) shown below are preferable.

[Chemical Formula 48.]

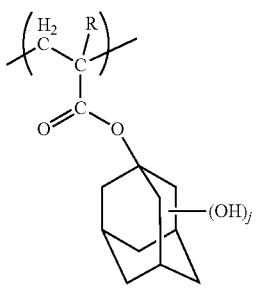
(a3-1)

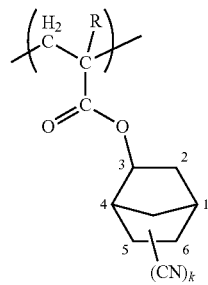
(a3-2)

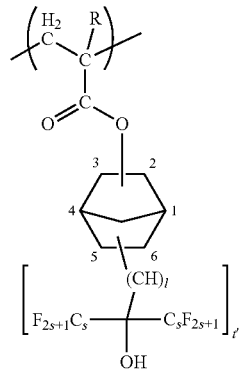
(a3-3)

In the formulas, R is the same as defined above; j is an integer of 1 to 3; k is an integer of 1 to 3; t' is an integer of 1 to 3; l is an integer of 1 to 5; and s is an integer of 1 to 3.

In formula (a3-1), j is preferably 1 or 2, and more preferably 1. When j is 2, it is preferable that the hydroxyl groups be bonded to the 3rd and 5th positions of the adamantyl group. When j is 1, it is preferable that the hydroxyl group be bonded to the 3rd position of the adamantyl group.

j is preferably 1, and it is particularly desirable that the hydroxyl group be bonded to the 3rd position of the adamantyl group.

In formula (a3-2), k is preferably 1. The cyano group is preferably bonded to the 5th or 6th position of the norbornyl group.

In formula (a3-3), t' is preferably 1. l is preferably 1. s is preferably 1. Further, it is preferable that a 2-norbornyl group or 3-norbornyl group be bonded to the terminal of the carboxy group of the acrylic acid. The fluorinated alkyl alcohol is preferably bonded to the 5th or 6th position of the norbornyl group.

As the structural unit (a3) contained in the component (A1), 1 type of structural unit may be used, or 2 or more types may be used.

When the component (A1) contains the structural unit (a3), the amount of the structural unit (a3) within the component (A1) based on the combined total of all structural units constituting the component (A1) is preferably 1 to 40 mol %, more preferably 2 to 30 mol %, still more preferably 5 to 25 mol %, and still more preferably 5 to 20 mol %.

When the amount of the structural unit (a3) is at least as large as the lower limit of the above preferable range, the effect of using the structural unit (a3) may be satisfactorily achieved. On the other hand, when the amount of the structural unit (a3) is no more than the upper limit of the above preferable range, a good balance may be achieved with the other structural units, and various lithography properties may be improved.

<<Other Structural Units>>

The component (A1) may be further include a structural unit other than the structural units (a10), (a1), (a2) and (a3).

Examples of other structural units include a structural unit derived from styrene, a structural unit derived from a styrene derivative (provided that the structural units that fall under the definition of structural unit (a10) are excluded), and a structural unit containing an acid non-dissociable, aliphatic cyclic group.

In the resist composition, as the component (A1), one kind of compound may be used, or two or more kinds of compounds may be used in combination.

The component (A1) preferably includes a polymeric compound (A1-1) having a structural unit (a1) (hereafter, sometimes referred to as "component (A1-1)").

Preferable examples of the component (A1-1) include a polymeric compound having a repeating structure of the structural units (a1) and (a2); and a polymeric compound having a repeating structure of the structural units (a1) and (a10).

In addition to the combination of the two structural units described above, the structural unit described above may be combined appropriately in order to obtain desired effects as a third structural unit, or alternatively, three or more of such structural units may be combined. The third structural unit is preferably the structural unit (a3).

The component (A1) can be produced, for example, by dissolving the monomers corresponding with each of the structural units in a polymerization solvent, followed by addition of a radical polymerization initiator such as azobisisobutyronitrile (AIBN) or dimethyl-2,2'-azobisisoutyrate (e.g., V-601). Alternatively, the component (A1) can be prepared by dissolving a monomer from which the structural unit (a1) is derived, and a precursor monomer (monomer for which the functional group is protected) from which the structural unit other than the structural unit (a1) is derived in a polymerization solvent, polymerizing the dissolved monomers using the radical polymerization initiator described above, followed by performing a deprotection reaction. In the polymerization, a chain transfer agent such as $HS-CH_2-CH_2-CH_2-C(CF_3)_2-OH$ may be used to introduce a $-C(CF_3)_2-OH$ group at the terminal(s) of the polymer. Such a copolymer having introduced a hydroxyalkyl group in which some of the hydrogen atoms of the alkyl group are substituted with fluorine atoms is effective in reducing developing defects and LER (line edge roughness: unevenness of the side walls of a line pattern).

The weight average molecular weight (Mw) (the polystyrene equivalent value determined by gel permeation chromatography (GPC)) of the component (A1) is not particularly limited, but is preferably 1,000 to 50,000, more preferably 2,000 to 30,000, and still more preferably 3,000 to 20,000.

When the Mw of the component (A1) is no more than the upper limit of the above-mentioned preferable range, the resist composition exhibits a satisfactory solubility in a resist solvent. On the other hand, when the Mw of the component (A1) is at least as large as the lower limit of the above-mentioned preferable range, dry etching resistance and the cross-sectional shape of the resist pattern becomes satisfactory.

The dispersity (Mw/Mn) of the component (A1) is not particularly limited, but is preferably 1.0 to 4.0, more preferably 1.0 to 3.0, and most preferably 1.1 to 2.0. Here, Mn is the number average molecular weight.

Component (A2)

In the resist composition of the present embodiment, as the component (A), "a base component which exhibits changed solubility in a developing solution under action of acid" other than the component (A1) (hereafter, referred to as "component (A2)") may be used in combination.

As the component (A2), there is no particular limitation, and any of the multitude of conventional base resins used within chemically amplified resist compositions may be arbitrarily selected for use.

As the component (A2), one kind of a polymer or a low molecular weight compound may be used, or a combination of two or more kinds may be used.

In the component (A), the amount of the component (A1) based on the total weight of the component (A) is preferably 25% by weight or more, more preferably 50% by weight or more, still more preferably 75% by weight or more, and may be even 100% by weight. When the amount of the component (A1) is 25% by weight or more, a resist pattern with improved lithography properties such as improvement in roughness may be reliably formed. Such effects are significant in lithography using electron beam or EUV.

In the resist composition of the present embodiment, the amount of the component (A) may be appropriately adjusted depending on the thickness of the resist film to be formed, and the like.

<Component (B)>

The component (B) is an acid generator component which generates acid upon exposure. In the resist composition of the present embodiment, the component (B) includes an acid generator (B1) containing a compound represented by general formula (b1) (hereafter, also is referred to as "component (B1)").

<<Component (B1)>>

The component (B1) is an acid generator containing a compound represented by general formula (b1) shown below.

[Chemical Formula 49.]

(b1)

In the formula, $R^{b1}$ represents an aryl group which may have a substituent; $R^{b2}$ and $R^{b3}$ each independently represents an aryl group which may have a substituent or an alkyl group which may have a substituent;

$R^{b2}$ and $R^{b3}$ may be mutually bonded to form a ring with the sulfur atom;

provided that at least one of the aryl group represented by $R^{b1}$ and the aryl group or the alkyl group represented by $R^{b2}$ or $R^{b3}$ has a substituent containing a halogen atom, and at least one of the aryl group represented by $R^{b1}$ and the aryl group or the alkyl group represented by $R^{b2}$ or $R^{b3}$ has a substituent containing a sulfonyl group; and $X^-$ represents a counteranion.

In formula (b1), examples of the aryl group represented by $R^{b1}$ include a group in which one hydrogen atom has been removed from an aromatic hydrocarbon ring such as benzene, naphthalene, anthracene, phenanthrene, biphenyl or fluorene. Among these examples, as the aryl group represented by $R^{b1}$, a group in which one hydrogen atom has been removed from benzene or naphthalene (a phenyl group or a naphthyl group) is preferable, and a group in which one hydrogen atom has been removed from benzene (a phenyl group) is more preferable.

In the formula, the aryl group represented by $R^{b2}$ or $R^{b3}$ is the same as defined for the aryl group represented by $R^{b1}$.

Among these examples, as the aryl group represented by $R^{b2}$ or $R^{b3}$, a group in which one hydrogen atom has been removed from benzene or naphthalene (a phenyl group or a naphthyl group) is preferable, and a group in which one hydrogen atom has been removed from benzene (a phenyl group) is more preferable.

In formula (b1), the alkyl group represented by $R^{b2}$ or $R^{b3}$ may be chain or cyclic.

Chain alkyl group which may have a substituent:

The chain alkyl group represented by $R^{b2}$ or $R^{b3}$ may be linear or branched.

The linear alkyl group preferably has 1 to 20 carbon atoms, more preferably 1 to 15 carbon atoms, and still more preferably 1 to 10 carbon atoms. Specific examples include a methyl group, an ethyl group, a propyl group, a butyl group, a pentyl group, a hexyl group, a heptyl group, an octyl group, a nonyl group, a decyl group, an undecyl group, a dodecyl group, a tridecyl group, an isotridecyl group, a tetradecyl group, a pentadecyl group, a hexadecyl group, an isohexadecyl group, a heptadecyl group, an octadecyl group, a nonadecyl group, an icosyl group, a henicosyl group and a docosyl group.

The branched alkyl group preferably has 3 to 20 carbon atoms, more preferably 3 to 15 carbon atoms, and still more preferably 3 to 10 carbon atoms. Specific examples include a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group and a 4-methylpentyl group.

Cyclic alkyl group which may have a substituent:

The cyclic alkyl group represented by $R^{b2}$ or $R^{b3}$ preferably has 3 to 15 carbon atoms, more preferably 4 to 12 carbon atoms, and still more preferably 5 to 10 carbon atoms. Examples thereof include groups in which one or more of the hydrogen atoms have been removed from a monocycloalkane; and groups in which one or more of the hydrogen atoms have been removed from a polycycloalkane such as a bicycloalkane, a tricycloalkane, or a tetracycloalkane. The monocycloalkane preferably has 3 to 6 carbon atoms, and specific examples thereof include cyclopentane and cyclohexane. Examples of polycycloalkanes include adamantane, norbornane, isobornane, tricyclodecane and tetracyclododecane.

Examples of the substituent for the aryl group represented by any of $R^{b1}$ to $R^{b3}$ or the alkyl group represented by $R^{b2}$ or $R^{b3}$ include an alkyl group, an alkoxy group, a halogen atom, a halogenated alkyl group, a sulfonyl group, a hydroxy group, a carbonyl group, a cyano group and an amino group, an aryl group having 6 to 20 carbon atoms, and a group represented by any one of formulae (ca-r-1) to (ca-r-7) shown below.

The alkyl group as the substituent is preferably an alkyl group of 1 to 5 carbon atoms, and a methyl group, an ethyl group, a propyl group, an n-butyl group or a tert-butyl group is particularly desirable.

The alkoxy group as the substituent is preferably an alkoxy group having 1 to 5 carbon atoms, more preferably a methoxy group, ethoxy group, n-propoxy group, isopropoxy group, n-butoxy group or tert-butoxy group, and most preferably a methoxy group or an ethoxy group.

Examples of the halogen atom for the substituent include a fluorine atom, a chlorine atom, a bromine atom and an iodine atom, and a fluorine atom is preferable.

Example of the aforementioned halogenated alkyl group includes a group in which a part or all of the hydrogen atoms within an alkyl group of 1 to 5 carbon atoms (e.g., a methyl group, an ethyl group, a propyl group, an n-butyl group or a tert-butyl group) have been substituted with the aforementioned halogen atoms.

[Chemical Formula 50.]

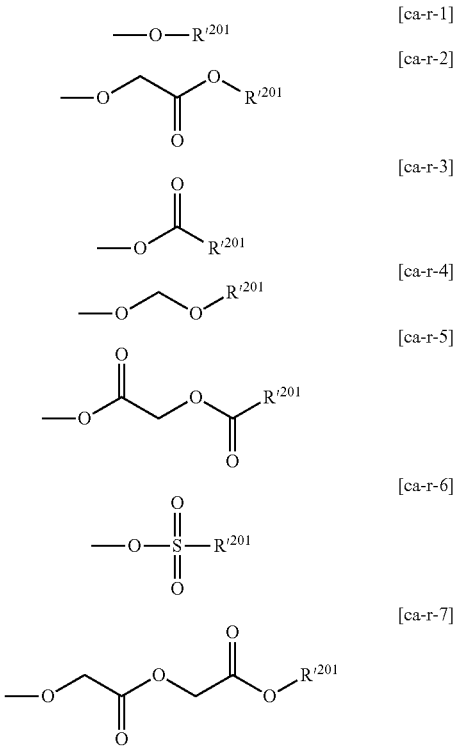

In the formulae, each $R'^{201}$ independently represents a hydrogen atom, a cyclic group which may have a substituent, a chain-like alkyl group which may have a substituent, or a chain-like alkenyl group which may have a substituent.

The cyclic group (which may have a substituent) represented by $R'^{201}$ is the same as defined for the aryl group (which may have a substituent) represented by $R^{b1}$ in the aforementioned formula (b1) and the cyclic alkyl group represented by $R^{b2}$ or $R^{b3}$ in the aforementioned formula (b1).

The chain alkyl group (which may have a substituent) represented by $R'^{201}$ is the same as defined for the chain alkyl group (which may have a substituent) represented by $R^{b2}$ or $R^{b3}$ in the aforementioned formula (b1).

Alternatively, the cyclic group (which may have a substituent) or the chain alkyl group (which may have a substituent) represented by $R'^{201}$ may be the same as defined for the acid dissociable group represented by the aforementioned formula (a1-r-2).

The chain alkenyl group (which may have a substituent) for $R'^{201}$ may be linear or branched, and preferably has 2 to 10 carbon atoms, more preferably 2 to 5 carbon atoms, still more preferably 2 to 4 carbon atoms, and most preferably 3 carbon atoms. Examples of linear alkenyl groups include a vinyl group, a propenyl group (an allyl group) and a butynyl group. Examples of branched alkenyl groups include a 1-methylvinyl group, a 2-methylvinyl group, a 1-methylpropenyl group and a 2-methylpropenyl group.

Among these examples, as the chain-like alkenyl group, a linear alkenyl group is preferable, a vinyl group or a propenyl group is more preferable, and a vinyl group is most preferable.

In formula (b1), in the case where $R^{b2}$ and $R^{b3}$ mutually bonded to form a ring with the sulfur atom, $R^{b2}$ and $R^{b3}$ may be bonded through a hetero atom such as a sulfur atom, an oxygen atom or a nitrogen atom, or a functional group such as a carbonyl group, —SO—, —COO—, —CONH— or —N($R_N$)— ($R_N$ represents an alkyl group having 1 to 5 carbon atoms). The ring containing the sulfur atom in the skeleton thereof is preferably a 3 to 10-membered ring, and most preferably a 5 to 7-membered ring. Specific examples of the ring formed include a thiophene ring, a thiazole ring, a benzothiophene ring, a thianthrene ring, a benzothiophene ring, a dibenzothiophene ring, a 9H-thioxanthene ring, a thioxanthone ring, a phenoxathiin ring, a tetrahydrothiophenium ring, and a tetrahydrothiopyranium ring.

In formula (b1), at least one of $R^{b1}$ to $R^{b3}$ represents an aryl group or alkyl group having a substituent containing a halogen atom, and at least one of $R^{b1}$ to $R^{b3}$ represents an aryl group or alkyl group having a substituent containing a sulfonyl group.

Regarding $R^{b1}$ to $R^{b3}$, examples of the substituent containing a halogen atom include a halogen atom and a halogenated alkyl group. Examples of the halogen atom include a fluorine atom, a chlorine atom, a bromine atom and an iodine atom, and a fluorine atom is preferable. Examples of the halogenated alkyl group include a group in which some or all hydrogen atoms in an alkyl group having 1 to 5 carbon atoms such as a methyl group, an ethyl group, a propyl group, an n-butyl group, or a tert-butyl group have been substituted with any of the above-mentioned halogen atoms.

Regarding $R^{b1}$ to $R^{b3}$, examples of the substituent containing a sulfonyl group include a monovalent group represented by the formula: —SO$_2$—$R^{b4}$ (wherein $R^{b4}$ represents a linear or branched alkyl group which may have a substituent, an alicyclic group which may have a substituent, or an aromatic hydrocarbon group which may have a substituent).

Examples of the linear or branched alkyl group represented by $R^{b4}$ include a methyl group, an ethyl group, a propyl group, an isopropyl group, an n-butyl group, an isobutyl group, a tert-butyl group, a pentyl group, an isopentyl group and a neopentyl group, preferably a methyl group or an ethyl group, and more preferably a methyl group.

As the substituent for the linear or branched alkyl group represented by $R^{b4}$, a halogen atom, a halogenated alkyl group having 1 to 5 carbon atoms, an alkoxy group having 1 to 5 carbon atoms, a hydroxy group, a carbonyl group and a carboxy group may be mentioned.

The alicyclic hydrocarbon group represented by $R^{b4}$ preferably has 3 to 20 carbon atoms, more preferably 3 to 12 carbon atoms. The alicyclic hydrocarbon group may be polycyclic or monocyclic. As the monocyclic alicyclic hydrocarbon group, a group in which one or more hydrogen atoms have been removed from a monocycloalkane is preferable. The monocycloalkane preferably has 3 to 6 carbon atoms, and specific examples thereof include cyclobutane, cyclopentane and cyclohexane. As the polycyclic alicyclic hydrocarbon group, a group in which one or more hydrogen atoms have been removed from a polycycloalkane is preferable, and the polycyclic group preferably has 7 to 12 carbon atoms. Examples of the polycycloalkane include adamantane, norbornane, isobornane, tricyclodecane and tetracyclododecane.

As the substituent for the alicyclic hydrocarbon group represented by $R^{b4}$, the same groups as those defined for $Ra^{05}$ may be mentioned.

Examples of the aromatic hydrocarbon group represented by $R^{b4}$ include a group in which one hydrogen atom has been removed from an aromatic hydrocarbon ring such as benzene, naphthalene, anthracene, phenanthrene, biphenyl or fluorene. Among these examples, as the aryl group represented by $R^{b1}$ to $R^{b3}$, a group in which one hydrogen atom has been removed from benzene or naphthalene (a phenyl group or a naphthyl group) is preferable, and a group in which one hydrogen atom has been removed from benzene (a phenyl group) is more preferable.

As the substituent for the aromatic hydrocarbon group represented by $R^{b4}$, the same groups as those defined for $Ra^{05}$ may be mentioned.

In formula (b1), in the case where $R^{b2}$ and $R^{b3}$ are mutually bonded to form a ring with the sulfur atom, one carbon atom of the ring skeleton may be replaced by a divalent sulfonyl group. The divalent sulfonyl group may be —SO$_2$—. Alternatively, the divalent sulfonyl group may be a sulfonyl group (—SO$_2$—) having a functional group other than a sulfonyl group or an atom bonded thereto, such as —SO$_3$—, —SO$_2$NH—, and —SO$_2$N($R_N$)—. In such case, the ring formed by $R^{b2}$ and $R^{b3}$ bonded together with the sulfur atom is not particularly limited, and the ring may or may not have an aromatic ring. In the case where the ring does not contain an aromatic ring, examples of the ring include a 1,4-dithiane-1,1-dioxide ring skeleton. In the case where the ring contains an aromatic ring, examples of the ring include a condensed bicyclic ring containing at least one benzene ring or a condensed tricyclic ring containing at least one benzene ring. Regarding the skeleton formed by the sulfur atom in the formula, $R^{b2}$, $R^{b3}$ and the divalent sulfonyl group, examples of the condensed bicyclic ring include a benzo[1,3]dithiol-1,1-dioxide skeleton, and examples of the condensed tricyclic ring include a thianthrene-5,5-dioxide skeleton.

In terms of the effects of the present embodiment, in formula (b1), at least one of $R^{b1}$ to $R^{b3}$ is preferably an aryl group having a substituent containing a halogen atom, and at least one of $R^{b1}$ to $R^{b3}$ is preferably an aryl group having a substituent containing a sulfonyl group.

Further, in terms of the effects of the present embodiment, in formula (b1), at least one of $R^{b1}$ to $R^{b3}$ is preferably an aryl group having a substituent containing a halogen atom at a meta-position, and at least one of $R^{b1}$ to $R^{b3}$ is an aryl group having a substituent containing a sulfonyl group at a meta-position and/or a para-position.

In the cation moiety of the component (B1), the number of the substituent containing a halogen atom and the number of the substituent containing a sulfonyl group are not particularly limited, and may be appropriately selected depending on the kind of the anion moiety of the component (B1), and the kind of the component (A).

Specific examples of the cation of the compound represented by the aforementioned formula (b1) include cations represented by formulae (ca-01-1) to (ca-01-38) shown below.

[Chemical Formula 51.]
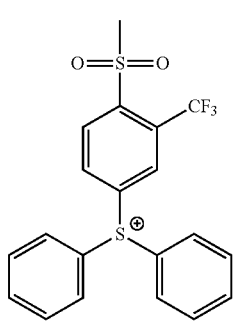
(ca-01-1)
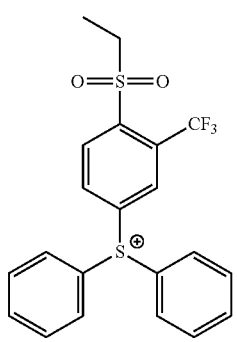
(ca-01-2)
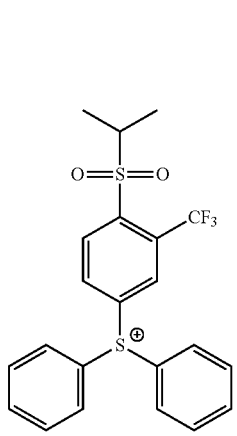
(ca-01-3)
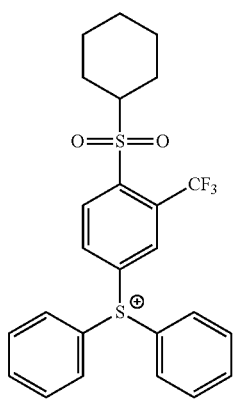
(ca-01-4)
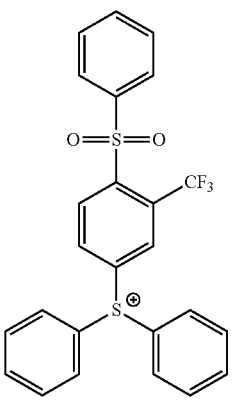
(ca-01-5)
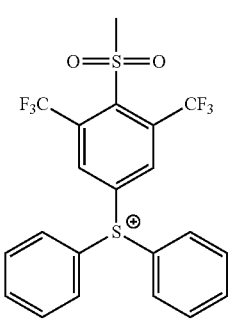
(ca-01-6)
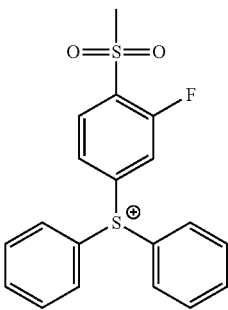
(ca-01-7)
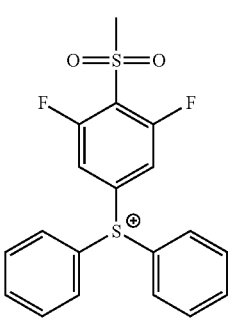
(ca-01-8)

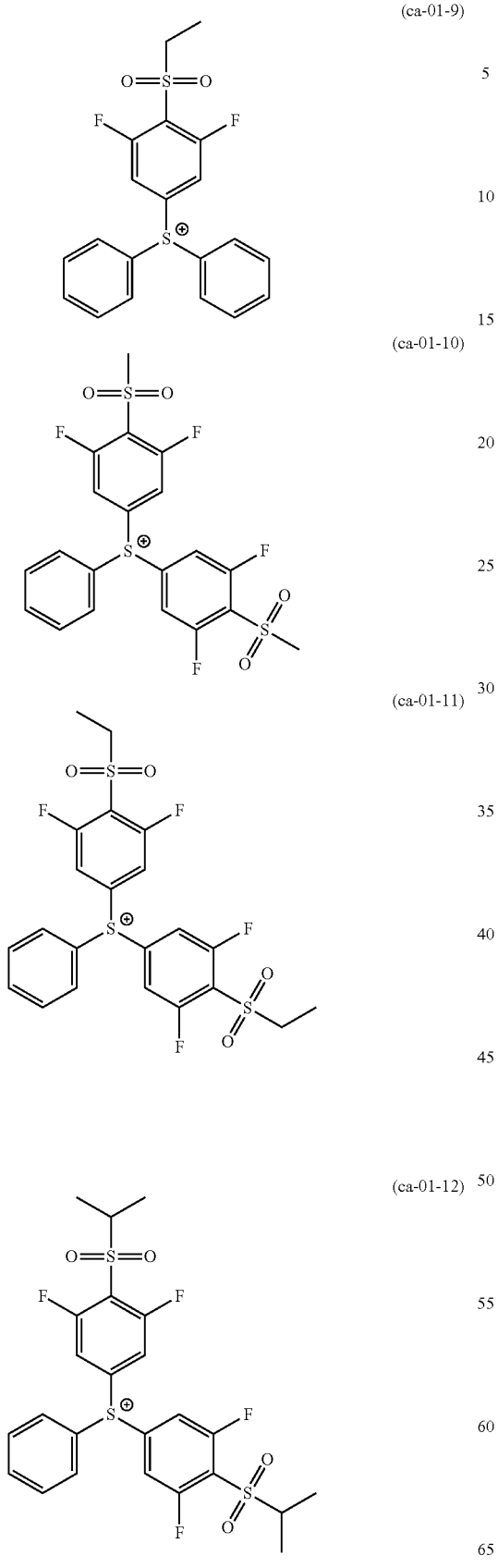
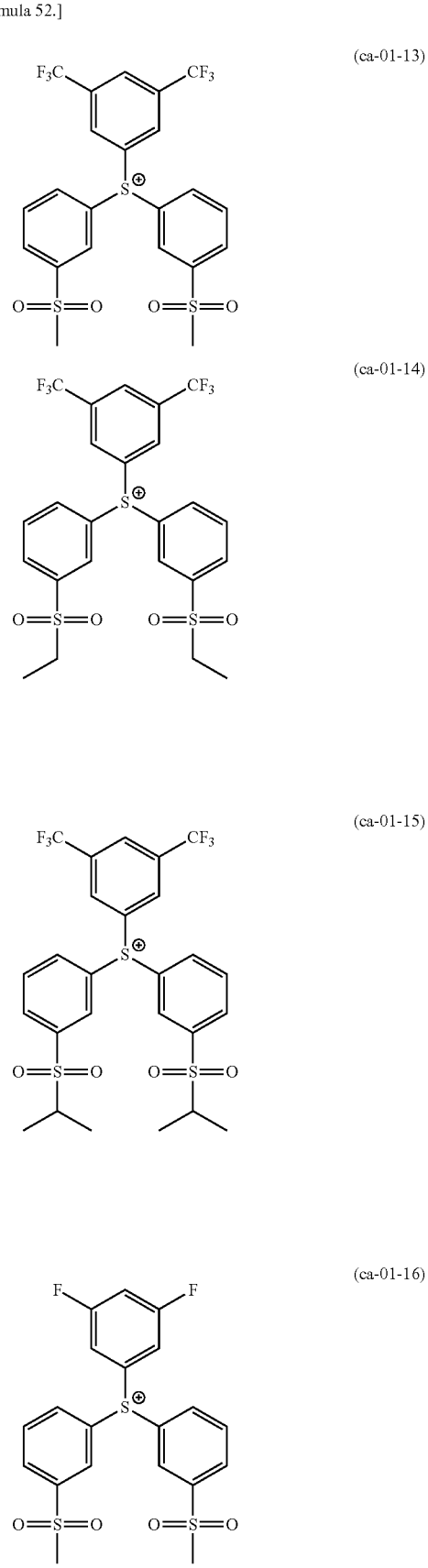

(ca-01-17)
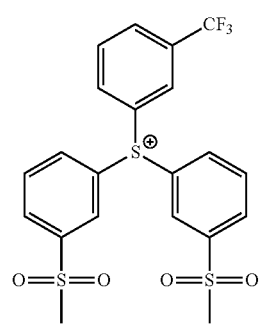
(ca-01-18)
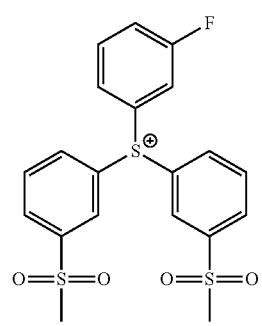
(ca-01-19)
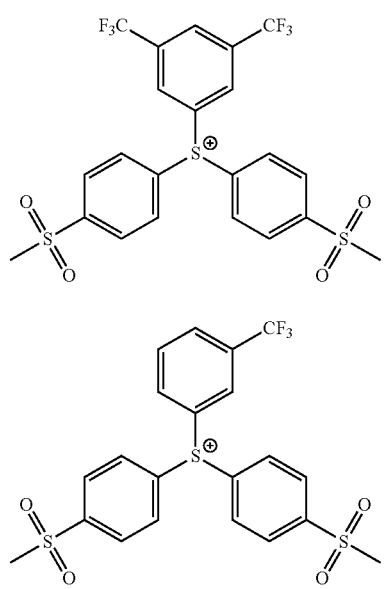
(ca-01-20)
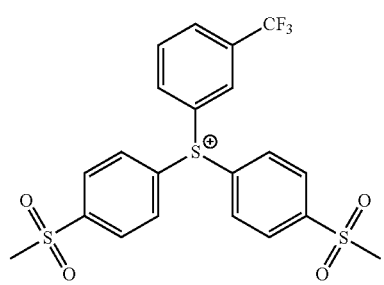
(ca-01-21)
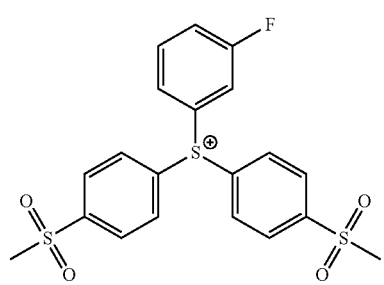
[Chemical Formula 53.]
(ca-01-22)
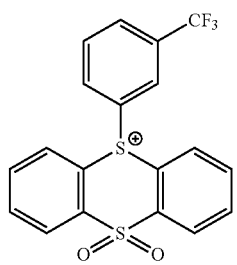
(ca-01-23)
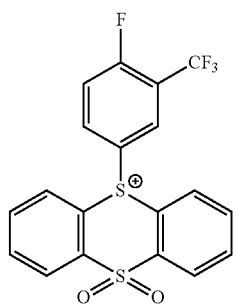
(ca-01-24)
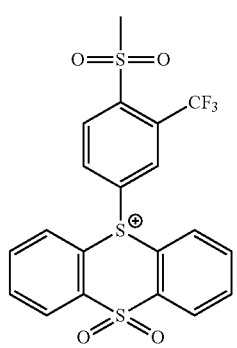
(ca-01-25)
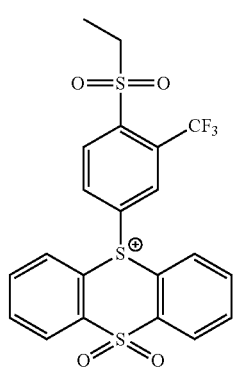

(ca-01-26)
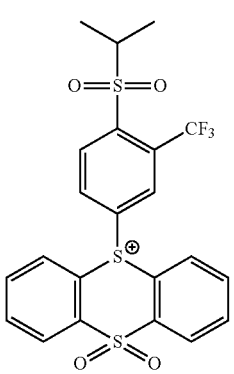
(ca-01-27)
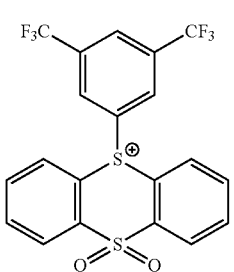
(ca-01-28)
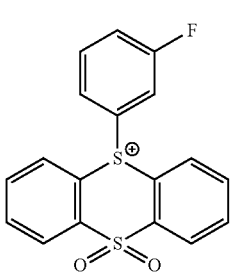
(ca-01-29)
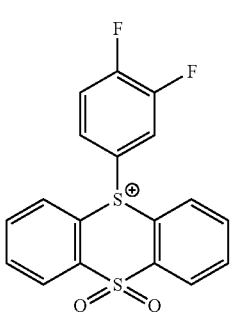
[Chemical Formula 54.]
(ca-01-30)
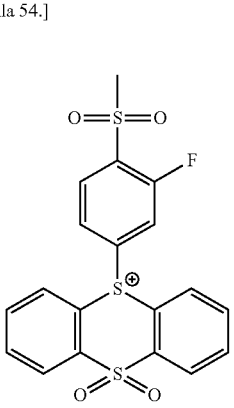
(ca-01-31)
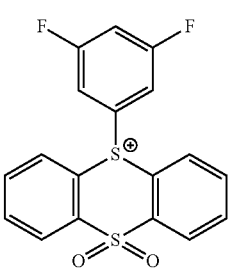
(ca-01-32)
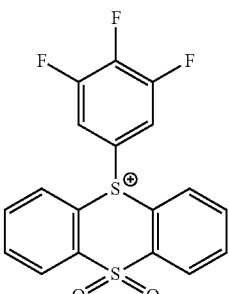
(ca-01-33)
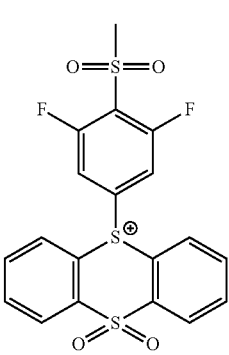
(ca-01-34)
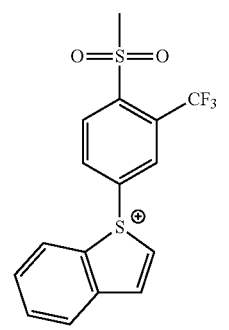
(ca-01-35)
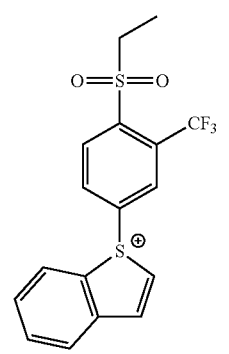

(ca-01-36)

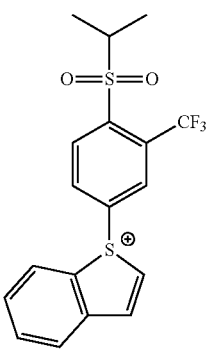

(ca-01-37)

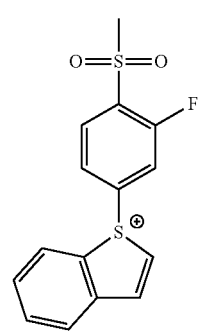

(ca-01-38)

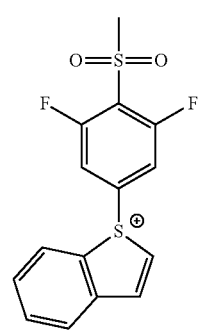

In formula (b1-1), X⁻ represents a counteranion.

X⁻ is not particularly limited, and any anion known as an anion moiety of an acid-generator component for a resist composition may be appropriately selected.

Examples of X⁻ include an anion represented by general formula (b1-1-an1) shown below, an anion represented by general formula (b1-1-an2) shown below, and an anion represented by general formula (b1-1-an3) shown below.

[Chemical Formula 55.]

(b1-1-an1)

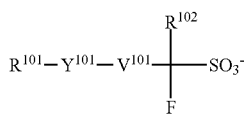

(b1-1-an2)

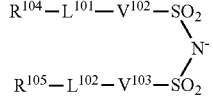

(b1-1-an3)

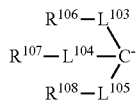

In the formulae, $R^{101}$ and $R^{104}$ to $R^{108}$ each independently represents a cyclic group which may have a substituent, a chain-like alkyl group which may have a substituent or a chain-like alkenyl group which may have a substituent, provided that $R^{104}$ and $R^{105}$ may be mutually bonded to form a ring structure; $R^{102}$ represents a fluorine atom or a fluorinated alkyl group having 1 to 5 carbon atoms; $Y^{101}$ represents a single bond or a divalent group containing an oxygen atom; $V^{101}$ to $V^{103}$ each independently represents a single bond, an alkylene group or a fluorinated alkylene group; $L^{101}$ and $L^{102}$ each independently represents a single bond or an oxygen atom; and $L^{103}$ to $L^{105}$ each independently represents a single bond, —CO— or —SO₂—.

Anion Represented by General Formula (b1-1-an1)

In the formula (b1-1-an1), $R^{101}$ represents a cyclic group which may have a substituent, a chain-like alkyl group which may have a substituent or a chain-like alkenyl group which may have a substituent.

Cyclic group which may have a substituent:

The cyclic group is preferably a cyclic hydrocarbon group, and the cyclic hydrocarbon group may be either an aromatic hydrocarbon group or an aliphatic hydrocarbon group. An "aliphatic hydrocarbon group" refers to a hydrocarbon group that has no aromaticity. The aliphatic hydrocarbon group may be either saturated or unsaturated, but in general, the aliphatic hydrocarbon group is preferably saturated.

The aromatic hydrocarbon group for $R^{101}$ is a hydrocarbon group having an aromatic ring. The aromatic hydrocarbon group preferably has 3 to 30 carbon atoms, more preferably 5 to 30 carbon atoms, still more preferably 5 to 20 carbon atoms, and most preferably 6 to 18 carbon atoms. Here, the number of carbon atoms within a substituent(s) is not included in the number of carbon atoms of the aromatic hydrocarbon group.

Examples of the aromatic ring contained in the aromatic hydrocarbon group represented by $R^{101}$ include benzene, fluorene, naphthalene, anthracene, phenanthrene and biphenyl; and aromatic hetero rings in which part of the carbon atoms constituting the aforementioned aromatic rings has been substituted with a hetero atom. Examples of the hetero atom within the aromatic hetero rings include an oxygen atom, a sulfur atom and a nitrogen atom.

Specific examples of the aromatic hydrocarbon group represented by $R^{101}$ include a group in which one hydrogen atom has been removed from an aromatic ring (an aryl group, such as a phenyl group or a naphthyl group), a group in which one hydrogen atom of the aforementioned aromatic ring has been substituted with an alkylene group (an arylalkyl group, such as a benzyl group, a phenethyl group, a 1-naphthylmethyl group, a 2-naphthylmethyl group, a 1-naphthylethyl group or a 2-naphthylethyl group), and a group in which one hydrogen atom has been removed from a condensed ring of the aforementioned aromatic ring and a bridged aliphatic ring such as bicycloheptane or bicyclooctane. The alkylene group (alkyl chain within the arylalkyl group) preferably has 1 to 4 carbon atom, more preferably 1 or 2, and most preferably 1.

Examples of the cyclic aliphatic hydrocarbon group for $R^{101}$ include aliphatic hydrocarbon groups containing a ring in the structure thereof.

As examples of the hydrocarbon group containing a ring in the structure thereof, an alicyclic hydrocarbon group (a group in which one hydrogen atom has been removed from an aliphatic hydrocarbon ring), a group in which the alicyclic hydrocarbon group is bonded to the terminal of the aforementioned chain-like aliphatic hydrocarbon group, and a group in which the alicyclic group is interposed within the aforementioned linear or branched aliphatic hydrocarbon group, can be given.

The alicyclic hydrocarbon group preferably has 3 to 20 carbon atoms, and more preferably 3 to 12 carbon atoms.

The alicyclic hydrocarbon group may be either a polycyclic group or a monocyclic group. As the monocyclic alicyclic hydrocarbon group, a group in which one or more hydrogen atoms have been removed from a monocycloalkane is preferable. The monocycloalkane preferably has 3 to 6 carbon atoms, and specific examples thereof include cyclopentane and cyclohexane. As the polycyclic alicyclic hydrocarbon group, a group in which one or more hydrogen atoms have been removed from a polycycloalkane is preferable, and the polycyclic group preferably has 7 to 30 carbon atoms. Among polycycloalkanes, a polycycloalkane having a bridged ring polycyclic skeleton, such as adamantane, norbornane, isobornane, tricyclodecane or tetracyclodpdecane, and a polycycloalkane having a condensed ring polycyclic skeleton, such as a cyclic group having a steroid skeleton are preferable.

Among these examples, as the cyclic aliphatic hydrocarbon group for $R^{101}$, a group in which one or more hydrogen atoms have been removed from a monocycloalkane or a polycycloalkane is preferable, a group in which one or more hydrogen atoms have been removed from a polycycloalkane is more preferable, an adamantyl group or a norbornyl group is still more preferable, and an adamantyl group is most preferable.

The linear aliphatic hydrocarbon group which may be bonded to the alicyclic hydrocarbon group preferably has 1 to 10 carbon atoms, more preferably 1 to 6 carbon atoms, still more preferably 1 to 4 carbon atoms, and most preferably 1 to 3 carbon atoms. As the linear aliphatic hydrocarbon group, a linear alkylene group is preferable. Specific examples thereof include a methylene group [—$CH_2$—], an ethylene group [—$(CH_2)_2$—], a trimethylene group [—$(CH_2)_3$—], a tetramethylene group [—$(CH_2)_4$—] and a pentamethylene group [—$(CH_2)_5$—].

The branched aliphatic hydrocarbon group which may be bonded to the alicyclic hydrocarbon group preferably has 2 to 10 carbon atoms, more preferably 3 to 6 carbon atoms, still more preferably 3 or 4 carbon atoms, and most preferably 3 carbon atoms. As the branched aliphatic hydrocarbon group, branched alkylene groups are preferred, and specific examples include various alkylalkylene groups, including alkylmethylene groups such as —$CH(CH_3)$—, —$CH(CH_2CH_3)$—, —$C(CH_3)_2$—, —$C(CH_3)(CH_2CH_3)$—, —$C(CH_3)(CH_2CH_2CH_3)$—, and —$C(CH_2CH_3)_2$—; alkylethylene groups such as —$CH(CH_3)CH_2$—, —$CH(CH_3)CH(CH_3)$—, —$C(CH_3)_2CH_2$—, —$CH(CH_2CH_3)CH_2$—, and —$C(CH_2CH_3)_2$—$CH_2$—; alkyltrimethylene groups such as —$CH(CH_3)CH_2CH_2$—, and —$CH_2CH(CH_3)CH_2$—; and alkyltetramethylene groups such as —$CH(CH_3)CH_2CH_2CH_2$—, and —$CH_2CH(CH_3)CH_2CH_2$—. As the alkyl group within the alkylalkylene group, a linear alkyl group of 1 to 5 carbon atoms is preferable.

The cyclic hydrocarbon group for $R^{101}$ may contain a hetero atom such as a heterocycle. Specific examples include lactone-containing cyclic groups represented by the aforementioned general formulae (a2-r-1) to (a2-r-7), the —$SO_2$— containing cyclic group represented by the aforementioned formulae (a5-r-1) to (a5-r-4), and other heterocyclic groups represented by the aforementioned chemical formulae (r-hr-1) to (r-hr-16).

As the substituent for the cyclic group for $R^{101}$, an alkyl group, an alkoxy group, a halogen atom, a halogenated alkyl group, a hydroxyl group, a carbonyl group, a nitro group or the like can be used.

The alkyl group as the substituent is preferably an alkyl group of 1 to 5 carbon atoms, and a methyl group, an ethyl group, a propyl group, an n-butyl group or a tert-butyl group is particularly desirable.

The alkoxy group as the substituent is preferably an alkoxy group having 1 to 5 carbon atoms, more preferably a methoxy group, ethoxy group, n-propoxy group, isopropoxy group, n-butoxy group or tert-butoxy group, and most preferably a methoxy group or an ethoxy group.

Examples of the halogen atom for the substituent include a fluorine atom, a chlorine atom, a bromine atom and an iodine atom, and a fluorine atom is preferable.

Example of the aforementioned halogenated alkyl group includes a group in which a part or all of the hydrogen atoms within an alkyl group of 1 to 5 carbon atoms (e.g., a methyl group, an ethyl group, a propyl group, an n-butyl group or a tert-butyl group) have been substituted with the aforementioned halogen atoms.

The carbonyl group as the substituent is a group that substitutes a methylene group (—$CH_2$—) constituting the cyclic hydrocarbon group.

Chain alkyl group which may have a substituent:

The chain-like alkyl group for $R^{101}$ may be linear or branched.

The linear alkyl group preferably has 1 to 20 carbon atoms, more preferably 1 to 15, and most preferably 1 to 10. Specific examples include a methyl group, an ethyl group, a propyl group, a butyl group, a pentyl group, a hexyl group, a heptyl group, an octyl group, a nonyl group, a decyl group, an undecyl group, a dodecyl group, a tridecyl group, an isotridecyl group, a tetradecyl group, a pentadecyl group, a hexadecyl group, an isohexadecyl group, a heptadecyl group, an octadecyl group, a nonadecyl group, an icosyl group, a henicosyl group and a docosyl group.

The branched alkyl group preferably has 3 to 20 carbon atoms, more preferably 3 to 15, and most preferably 3 to 10. Specific examples include a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group and a 4-methylpentyl group.

Chain alkenyl group which may have a substituent:

The chain-like alkenyl group for $R^{101}$ may be linear or branched, and preferably has 2 to 10 carbon atoms, more preferably 2 to 5 carbon atoms, still more preferably 2 to 4 carbon atoms, and most preferably 3 carbon atoms. Examples of linear alkenyl groups include a vinyl group, a propenyl group (an allyl group) and a butynyl group. Examples of branched alkenyl groups include a 1-methylvinyl group, a 2-methylvinyl group, a 1-methylpropenyl group and a 2-methylpropenyl group.

Among these examples, as the chain-like alkenyl group, a linear alkenyl group is preferable, a vinyl group or a propenyl group is more preferable, and a vinyl group is most preferable.

As the substituent for the chain-like alkyl group or alkenyl group for $R^{101}$, an alkoxy group, a halogen atom, a halogenated alkyl group, a hydroxyl group, a carbonyl group, a nitro group, an amino group, a cyclic group for $R^{101}$ or the like can be used.

Among the above examples, as $R^{101}$, a cyclic group which may have a substituent is preferable, and a cyclic hydrocarbon group which may have a substituent is more preferable. Specifically, a phenyl group, a naphthyl group, a group in which one or more hydrogen atoms have been removed from a polycycloalkane, a lactone-containing cyclic group represented by any one of the aforementioned formula (a2-r-1) to (a2-r-7), and an —$SO_2$— containing cyclic group represented by any one of the aforementioned formula (a5-r-1) to (a5-r-4).

In formula (b1-1-an1), $Y^{101}$ represents a single bond or a divalent linking group containing an oxygen atom.

In the case where $Y^{101}$ is a divalent linking group containing an oxygen atom, $Y^{10}1$ may contain an atom other than an oxygen atom. Examples of atoms other than an oxygen atom include a carbon atom, a hydrogen atom, a sulfur atom and a nitrogen atom.

Examples of divalent linking groups containing an oxygen atom include non-hydrocarbon, oxygen atom-containing linking groups such as an oxygen atom (an ether bond; —O—), an ester bond (—C(=O)—O—), an oxycarbonyl group (—O—C(=O)—), an amido bond (—C(=O)—NH—), a carbonyl group (—C(=O)—) and a carbonate bond (—O—C(=O)—O—); and combinations of the aforementioned non-hydrocarbon, hetero atom-containing linking groups with an alkylene group. Furthermore, the combinations may have a sulfonyl group (—$SO_2$—) bonded thereto. Examples of divalent linking groups containing an oxygen atom include linking groups represented by general formulae (y-a1-1) to (y-a1-7) shown below.

[Chemical Formula 56.]

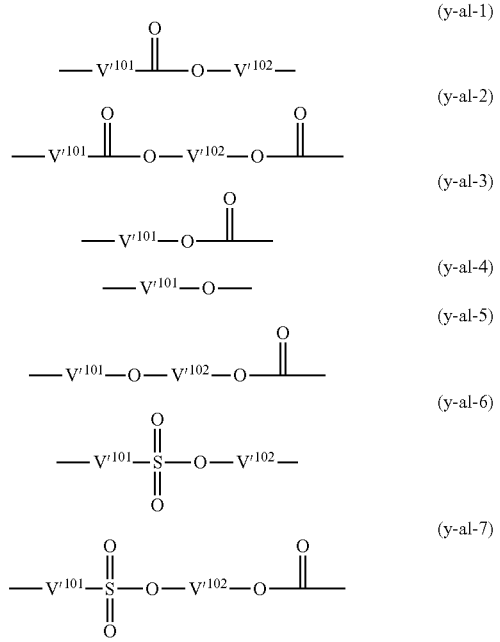

(y-a1-1)
(y-a1-2)
(y-a1-3)
(y-a1-4)
(y-a1-5)
(y-a1-6)
(y-a1-7)

In the formulae, $V'^{101}$ represents a single bond or an alkylene group of 1 to 5 carbon atoms; $V'^{102}$ represents a divalent saturated hydrocarbon group of 1 to 30 carbon atoms.

The divalent saturated hydrocarbon group for $V'^{102}$ is preferably an alkylene group of 1 to 30 carbon atoms, more preferably an alkylene group of 1 to 10 carbon atoms, and still more preferably an alkylene group of 1 to 5 carbon atoms.

The alkylene group for $V'^{101}$ and $V'^{102}$ may be a linear alkylene group or a branched alkylene group, and a linear alkylene group is preferable.

Specific examples of the alkylene group for $V'^{101}$ and $V'^{102}$ include a methylene group [—$CH_2$—]; an alkylmethylene group, such as —CH($CH_3$)—, —CH($CH_2CH_3$)—, —C($CH_3$)$_2$—, —C($CH_3$)($CH_2CH_3$)—, —C($CH_3$)($CH_2CH_2CH_3$)— and —C($CH_2CH_3$)$_2$—; an ethylene group [—$CH_2CH_2$—]; an alkylethylene group, such as —CH($CH_3$)$CH_2$—, —CH($CH_3$)CH($CH_3$)—, —C($CH_3$)$_2CH_2$— and —CH($CH_2CH_3$)$CH_2$—; a trimethylene group (n-propylene group) [—$CH_2CH_2CH_2$—]; an alkyltrimethylene group, such as —CH($CH_3$)$CH_2CH_2$— and —$CH_2$CH($CH_3$)$CH_2$—; a tetramethylene group [—$CH_2CH_2CH_2CH_2$—]; an alkyltetramethylene group, such as —CH($CH_3$)$CH_2CH_2CH_2$—, —$CH_2$CH($CH_3$)$CH_2CH_2$—; and a pentamethylene group [—$CH_2CH_2CH_2CH_2CH_2$—].

Further, part of methylene group within the alkylene group for $V'^{101}$ and $V'^{102}$ may be substituted with a divalent aliphatic cyclic group of 5 to 10 carbon atoms. The aliphatic cyclic group is preferably a divalent group in which one hydrogen atom has been removed from the cyclic aliphatic hydrocarbon group (monocyclic aliphatic hydrocarbon group or polycyclic aliphatic hydrocarbon group) for $Ra'^3$ in the aforementioned formula (a1-r-1), and a cyclohexylene group, 1,5-adamantylene group or 2,6-adamantylene group is preferable.

$Y^{101}$ is preferably a divalent linking group containing an ether bond or a divalent linking group containing an ester bond, and groups represented by the aforementioned formulas (y-a1-1) to (y-a1-5) are preferable.

In formula (b1-1-an1), $V^{101}$ represents a single bond, an alkylene group or a fluorinated alkylene group. The alkylene group and the fluorinated alkylene group for $V^{101}$ preferably has 1 to 4 carbon atoms. Examples of the fluorinated alkylene group for $V^{101}$ include a group in which part or all of the hydrogen atoms within the alkylene group for $V^{101}$ have been substituted with fluorine. Among these examples, as $V^{101}$, a single bond or a fluorinated alkylene group of 1 to 4 carbon atoms is preferable.

In formula (b1-1-an1), $R^{102}$ represents a fluorine atom or a fluorinated alkyl group of 1 to 5 carbon atoms. $R^{102}$ is preferably a fluorine atom or a perfluoroalkyl group of 1 to 5 carbon atoms, and more preferably a fluorine atom.

As a specific example of the anion moiety represented by the aforementioned formula (b1-1-an1), in the case where $Y^{101}$ a single bond, a fluorinated alkylsulfonate anion such as a trifluoromethanesulfonate anion or a perfluorobutanesulfonate anion can be mentioned; and in the case where $Y^{101}$ represents a divalent linking group containing an oxygen atom, anions represented by formulae (an-1) to (an-3) shown below can be mentioned.

[Chemical Formula 57.]

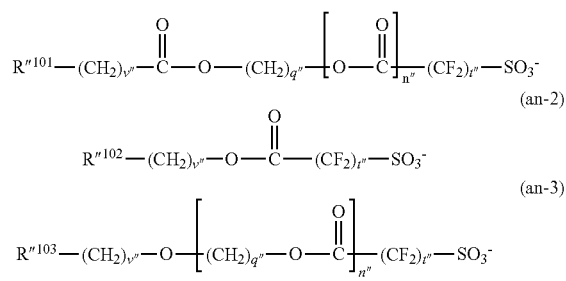

In the formulae, $R''^{101}$ represents an aliphatic cyclic group which may have a substituent, a group represented by any one of the aforementioned formulas (r-hr-1) to (r-hr-6) or a chain-like alkyl group which may have a substituent; $R''^{102}$ represents an aliphatic cyclic group which may have a substituent, a lactone-containing cyclic group represented by any one of the aforementioned formulae (a2-r-1) to (a2-r-7) or an —$SO_2$— containing cyclic group represented by any one of the aforementioned formulae (a5-r-1) to (a5-r-4); $R''^{103}$ represents an aromatic cyclic group which may have a substituent, an aliphatic cyclic group which may have a substituent or a chain-like alkenyl group which may have a substituent; v″ represents an integer of 0 to 3; q″ represents an integer of 1 to 20; t″ represents an integer of 1 to 3; and n″ represents 0 or 1.

As the aliphatic cyclic group for $R''^{101}$, $R''^{102}$ and $R''^{103}$ which may have a substituent, the same groups as the cyclic aliphatic hydrocarbon group for $R^{101}$ described above are preferable. As the substituent, the same groups as those described above for substituting the cyclic aliphatic hydrocarbon group for $R^{101}$ can be mentioned.

As the aromatic cyclic group for $R''^{103}$ which may have a substituent, the same groups as the aromatic hydrocarbon group for the cyclic hydrocarbon group represented by $R^{101}$ described above are preferable. The substituent is the same as defined for the substituent for the aromatic hydrocarbon group represented by $R^{101}$.

As the chain-like alkyl group for $R''^{101}$ which may have a substituent, the same groups as those described above for $R^{101}$ are preferable. As the chain-like alkenyl group for $R''^{103}$ which may have a substituent, the same groups as those described above for $R^{101}$ are preferable.

Anion Represented by General Formula (b1-1-an2) In formula (b1-1-an2), $R^{104}$ and $R^{105}$ each independently represents a cyclic group which may have a substituent, a chain-like alkyl group which may have a substituent or a chain-like alkenyl group which may have a substituent, and is the same as defined for $R^{101}$ in formula (b1-1-an1). $R^{104}$ and $R^{105}$ may be mutually bonded to form a ring.

As $R^{104}$ and $R^{105}$, a chain-like alkyl group which may have a substituent is preferable, and a linear or branched alkyl group or a linear or branched fluorinated alkyl group is more preferable.

The chain-like alkyl group preferably has 1 to 10 carbon atoms, more preferably 1 to 7 carbon atoms, and still more preferably 1 to 3 carbon atoms. The smaller the number of carbon atoms of the chain-like alkyl group for $R^{104}$ and $R^{105}$, the more the solubility in a resist solvent is improved. Further, in the chain-like alkyl group for $R^{104}$ and $R^{105}$, it is preferable that the number of hydrogen atoms substituted with fluorine atoms is as large as possible because the acid strength increases. The fluorination ratio of the chain-like alkyl group is preferably from 70 to 100%, more preferably from 90 to 100%, and it is particularly desirable that the chain-like alkyl group be a perfluoroalkyl group in which all hydrogen atoms are substituted with fluorine atoms.

In formula (b1-1-an2), $V^{102}$ and $V^{103}$ each independently represents a single bond, an alkylene group or a fluorinated alkylene group, and is the same as defined for $V^{101}$ in formula (b1-1-an1).

In formula (b1-1-an2), $L^{101}$ and $L^{102}$ each independently represents a single bond or an oxygen atom.

Anion Represented by General Formula (b1-1-an3)

In formula (b1-1-an3), $R^{106}$ to $R^{108}$ each independently represents a cyclic group which may have a substituent, a chain-like alkyl group which may have a substituent or a chain-like alkenyl group which may have a substituent, and is the same as defined for $R^{101}$ in formula (b1-1-an1).

In formula (b1-1-an3), $L^{103}$ to $L^{105}$ each independently represents a single bond, —CO— or —$SO_2$—.

In the aforementioned formula (b1-1), X⁻ may be $R^{109}$— $SO_3$—. $R^{109}$ represents a cyclic group which may have a substituent, a chain alkyl group which may have a substituent, or a chain alkenyl group which may have a substituent, and is the same as defined for $R^{101}$ in the aforementioned formula (b1-1-an1). However, in $R^{109}$, the carbon atom adjacent to the S atom has a fluorine atom bonded thereto.

Alternatively, in the aforementioned formula (b1-1), X⁻ may be a halogen anion. Examples of the halogen anion include a fluoride ion, a chloride ion, a bromide ion and an iodide ion.

Among these examples, as the anion moiety of the component (B1), an anion represented by general formula (b1-1-an1) is preferable. Among these, an anion represented by any one of the aforementioned general formulae (an-1) to (an-3) is more preferable, and an anion represented by the aforementioned general formula (an-1) or (an-2) is more preferable.

Preferable examples of the component (B1) include a combination of an anion represented by any one of the aforementioned formulae (b1-1-an1) to (b1-1-an3) (more preferably an anion represented by any one of general formulae (an-1) to (an-3)) with a cation represented by any one of formulae (ca-01-1) to (ca-01-38). Specific examples of the component (B1) are shown below, although the component (B1) is not limited to these examples.

[Chemical Formula 58.]

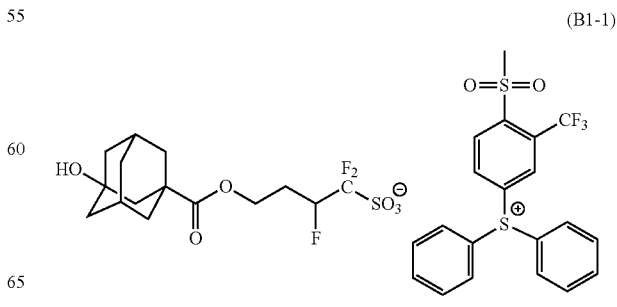

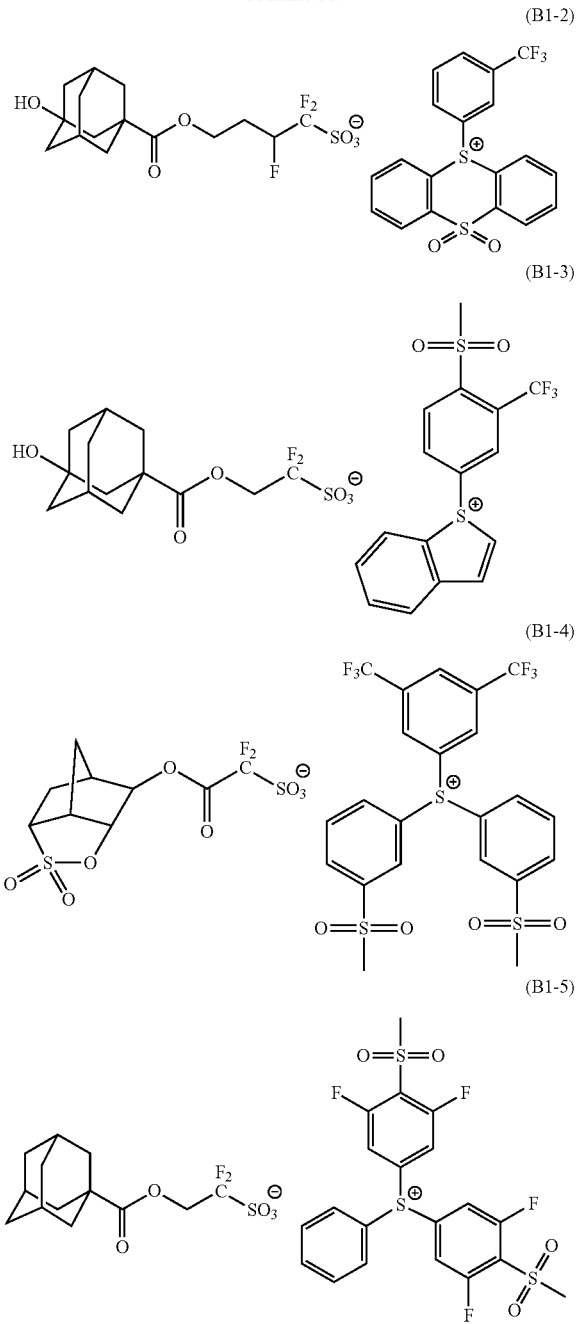

more preferably 95% by weight or more. The amount of the component (B1) within the component (B) may be even 100% by weight.

When the amount of the component (B1) is at least as large as the lower limit of the above-mentioned preferable range, in the formation of a resist pattern, sensitivity and various lithography properties such as line width roughness (LWR) and pattern shape are improved. On the other hand, in the case where the amount of the component (B1) is no more than the upper limit of the above-mentioned preferable range, when each of the components of the resist composition are dissolved in an organic solvent, a homogeneous solution may be more reliably obtained and the storage stability of the resist composition becomes satisfactory.

<<Component (B2)>>

The resist composition of the present embodiment may contain an acid generator other than the component (B1) (hereafter, referred to as "component (B2)"), as long as the effects of the present invention are not impaired.

As the component (B2), there is no particular limitation, and any of the known acid generators used in conventional chemically amplified resist compositions may be used.

Examples of these acid generators are numerous, and include onium salt acid generators such as iodonium salts and sulfonium salts; oxime sulfonate acid generators; diazomethane acid generators such as bisalkyl or bisaryl sulfonyl diazomethanes and poly(bis-sulfonyl)diazomethanes; nitrobenzylsulfonate acid generators; iminosulfonate acid generators; and disulfone acid generators.

As the onium salt acid generator, a compound represented by general formula (b-1) below (hereafter, sometimes referred to as "component (b-1)"), a compound represented by general formula (b-2) below (hereafter, sometimes referred to as "component (b-2)") or a compound represented by general formula (b-3) below (hereafter, sometimes referred to as "component (b-3)") may be mentioned. However, the component (b-1) does not include compounds which fall under the category of the component (B1).

[Chemical Formula 59.]

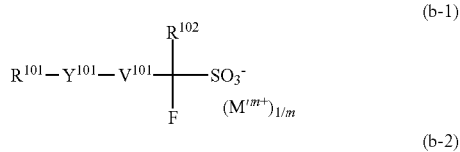

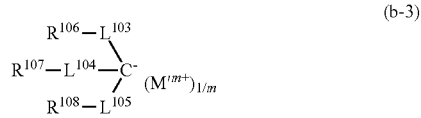

In the resist composition of the present embodiment, as the component (B1), one kind of compound may be used, or two or more kinds of compounds may be used in combination.

In the resist composition of the present embodiment, the amount of the component (B1) relative to 100 parts by weight of the component (A) is preferably within a range from 5 to 65 parts by weight, more preferably from 5 to 55 parts by weight, still more preferably from 10 to 45 parts by weight, and most preferably 10 to 40 parts by weight.

In the resist composition, the amount of the component (B1) within the entire component (B) capable of generating acid which acts on the component (A) is, for example, 50% by weight or more, preferably 70% by weight or more, and In the formulae, $R^{101}$ and $R^{104}$ to $R^{108}$ each independently represents a cyclic group which may have a substituent, a chain-like alkyl group which may have a substituent or a chain-like alkenyl group which may have a substituent, provided that $R^{104}$ and $R^{105}$ may be mutually bonded to form a ring; $R^{102}$ represents a fluorine atom or a fluorinated alkyl group of 1 to 5 carbon atoms; $Y^{101}$ represents a single bond or a divalent linking group containing an oxygen atom; $V^{101}$ to $V^{103}$ each independently represents a single bond, an alkylene group or a fluorinated alkylene group; $L^{101}$ and $L^{102}$ each independently represents a single bond or an oxygen atom; $L^{103}$ to $L^{105}$ each independently represents a single bond, —CO— or —SO$_2$—; and m represents an integer of 1 or more; and $M'^{m+}$ represents an m-valent onium cation.

In formulae (b-1), (b-2) and (b-3), $R^{101}$ and $R^{104}$ to $R^{108}$ are the same as defined for $R^{101}$ and $R^{104}$ to $R^{108}$ in the aforementioned formulae (b1-1-an1) to (b1-1-an3), respectively.

In formulae (b-1), (b-2) and (b-3), $R^{104}$ and $R^{105}$ are the same as defined for $R^{104}$ and $R^{105}$ in the aforementioned formulae (b1-1-an1) to (b1-1-an3), respectively.

In formulae (b-1), (b-2) and (b-3), $Y^{101}$ is the same as defined for $Y^{101}$ in the aforementioned formulae (b1-1-an1) to (b1-1-an3).

In formulae (b-1), (b-2) and (b-3), $V^{101}$ to $V^{103}$ are the same as defined for $V^{101}$ to $V^{103}$ in the aforementioned formulae (b1-1-an1) to (b1-1-an3), respectively.

In formulae (b-1), (b-2) and (b-3), $L^{101}$ and $L^{102}$ are the same as defined for $L^{101}$ and $L^{102}$ in the aforementioned formulae (b1-1-an1) to (b1-1-an3), respectively.

In formulae (b-1), (b-2) and (b-3), $L^{103}$ to $L^{105}$ are the same as defined for $L^{103}$ to $L^{105}$ in the aforementioned formulae (b1-1-an1) to (b1-1-an3), respectively.

In formulae (b-1), (b-2), and (b-3), m represents an integer of 1 or greater, $M'^{m+}$ represents an m-valent onium cation, and preferable examples thereof include a sulfonium cation and an iodonium cation.

Preferable examples of the cation moiety $((M'^{m+})/m)$ include an organic cation represented by any of general formulae (ca-1) to (ca-4) shown below. However, cations which fall under the definition of the cation moiety of the compound represented by general formula (b1) are excluded.

[Chemical Formula 60.]

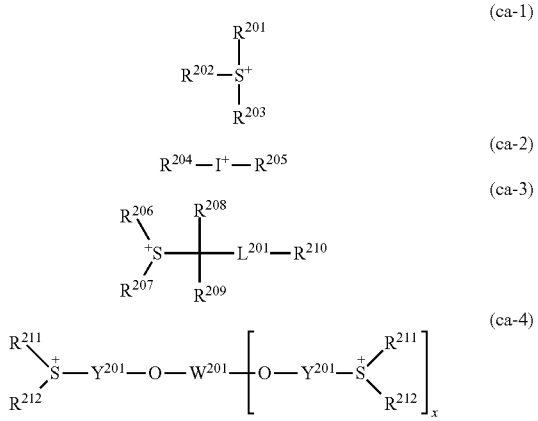

In the formulae, $R^{201}$ to $R^{207}$, $R^{211}$ and $R^{212}$ each independently represents an aryl group which may have a substituent, an alkyl group which may have a substituent, or an alkenyl group which may have a substituent. $R^{201}$ to $R^{203}$, $R^{206}$ and $R^{207}$, and $R^{211}$ and $R^{212}$ may be mutually bonded to form a ring with the sulfur atom. $R^{208}$ and $R^{209}$ each independently represents a hydrogen atom or an alkyl group of 1 to 5 carbon atoms. $R^{210}$ represents an aryl group which may have a substituent, an alkyl group which may have a substituent, an alkenyl group which may have a substituent, or an —SO$_2$— containing cyclic group which may have a substituent. $L^{201}$ represents —C(=O)— or —C(=O)—O—. Each $Y^{201}$ independently represents an arylene group, an alkylene group or an alkenylene group. x represents 1 or 2. $W^{201}$ represents an (x+1) valent linking group.

The aryl group represented by $R^{201}$ to $R^{207}$, $R^{211}$ and $R^{212}$ is the same as defined for the aryl group represented by $R^{b1}$ in the aforementioned formula (b1).

The alkyl group represented by $R^{201}$ to $R^{207}$, $R^{211}$ and $R^{212}$ is the same as the alkyl group represented by $R^{b2}$ and $R^{b3}$ in the aforementioned formula (b1).

The alkenyl group for $R^{201}$ to $R^{207}$, $R^{211}$ and $R^{212}$ preferably has 2 to 10 carbon atoms.

Specific examples of the substituent which $R^{201}$ to $R^{207}$ and $R^{210}$ to $R^{212}$ may have include an alkyl group, a halogen atom, a halogenated alkyl group, a carbonyl group, a cyano group, an amino group, an aryl group, and groups represented by the aforementioned general formulae (ca-r-1) to (ca-r-7).

In the case where $R^{201}$ to $R^{203}$, $R^{206}$ and $R^{207}$ or $R^{211}$ and $R^{212}$ are mutually bonded to form a ring with the sulfur atom, the ring is the same as defined for the case where $R^{b2}$ and $R^{b3}$ in the aforementioned formula (b1) are mutually bonded to form a ring with the sulfur atom.

$R^{208}$ and $R^{209}$ each independently represents a hydrogen atom or an alkyl group of 1 to 5 carbon atoms, preferably a hydrogen atom or an alkyl group of 1 to 3 carbon atoms, and when $R^{208}$ and $R^{209}$ each represents an alkyl group, $R^{208}$ and $R^{209}$ may be mutually bonded to form a ring.

$R^{210}$ represents an aryl group which may have a substituent, an alkyl group which may have a substituent, an alkenyl group which may have a substituent, or an —SO$_2$— containing cyclic group which may have a substituent.

Examples of the aryl group for $R^{210}$ include an unsubstituted aryl group of 6 to 20 carbon atoms, and a phenyl group or a naphthyl group is preferable.

As the alkyl group for $R^{210}$, a chain-like or cyclic alkyl group having 1 to 30 carbon atoms is preferable.

The alkenyl group for $R^{210}$ preferably has 2 to 10 carbon atoms.

As the —SO$_2$— containing cyclic group for $R^{210}$ which may have a substituent, an "—SO$_2$— containing polycyclic group" is preferable, and a group represented by the aforementioned general formula (a5-r-1) is more preferable.

Each $Y^{201}$ independently represents an arylene group, an alkylene group or an alkenylene group.

Examples of the arylene group for $Y^{201}$ include groups in which one hydrogen atom has been removed from an aryl group given as an example of the aromatic hydrocarbon group for $R^{101}$ in the aforementioned formula (b1-1-an1).

Examples of the alkylene group and alkenylene group for $Y^{201}$ include groups in which one hydrogen atom has been removed from the chain-like alkyl group or the chain-like alkenyl group given as an example of $R^{101}$ in the aforementioned formula (b1-1-an1).

In the formula (ca-4), x represents 1 or 2.

$W^{201}$ represents a linking group having a valency of (x+1), i.e., a divalent or trivalent linking group.

As the divalent linking group for $W^{201}$, a divalent hydrocarbon group which may have a substituent is preferable, and as examples thereof, the same hydrocarbon groups (which may have a substituent) as those described above for $Y^{a21}$ in the general formula (a2-1) can be mentioned. The divalent linking group for $W^{201}$ may be linear, branched or cyclic, and cyclic is more preferable. Among these, an arylene group having two carbonyl groups, each bonded to the terminal thereof is preferable. Examples of the arylene group include a phenylene group and a naphthylene group, and a phenylene group is particularly desirable.

As the trivalent linking group for $W^{201}$, a group in which one hydrogen atom has been removed from the aforementioned divalent linking group for $W^{201}$ and a group in which the divalent linking group has been bonded to another divalent linking group can be mentioned. The trivalent linking group for $W^{201}$ is preferably a group in which 2 carbonyl groups are bonded to an arylene group.

Specific examples of preferable cations represented by formula (ca-1) include cations represented by formulae (ca-1-1) to (ca-1-71) shown below.

[Chemical Formula 61.]

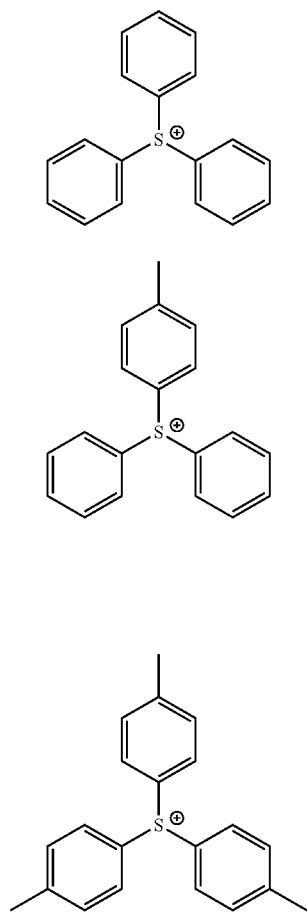

(ca-1-1)

(ca-1-2)

(ca-1-3)

(ca-1-4)

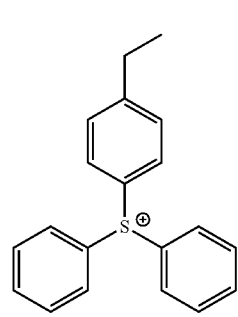

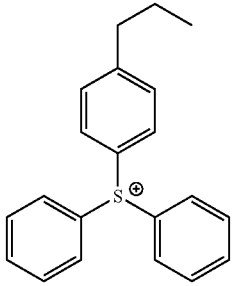

(ca-1-5)

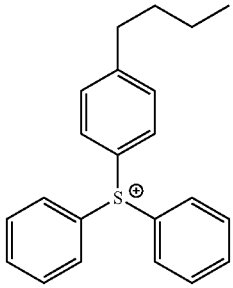

(ca-1-6)

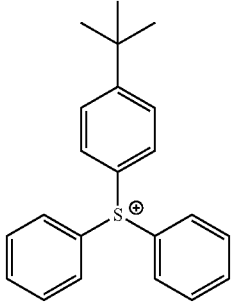

(ca-1-7)

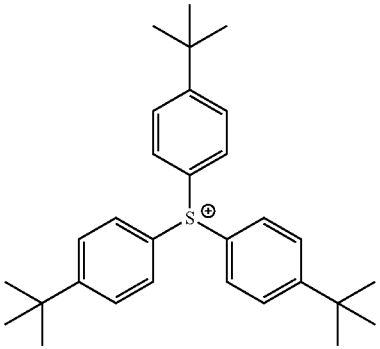

(ca-1-8)

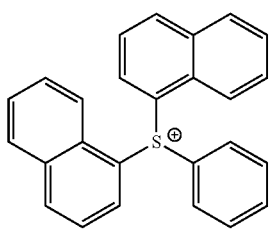

(ca-1-9)

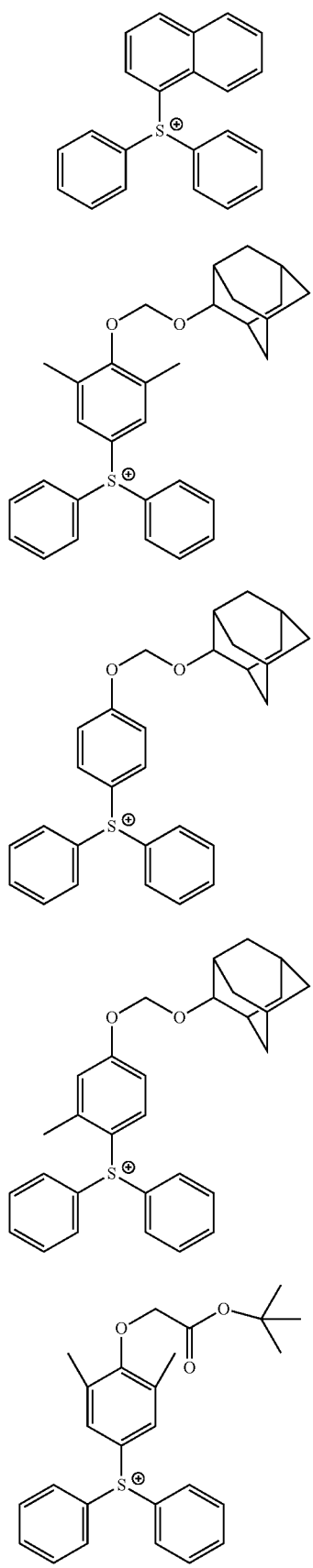
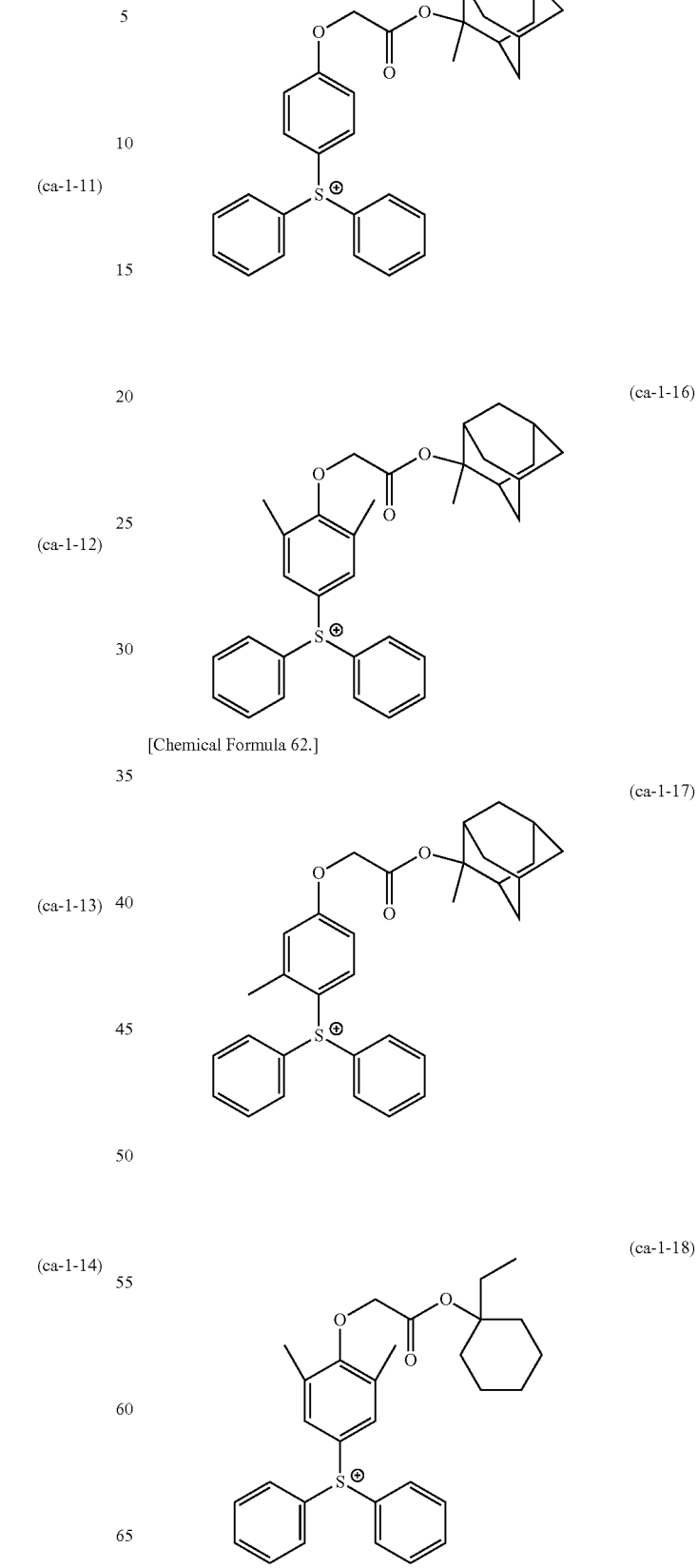

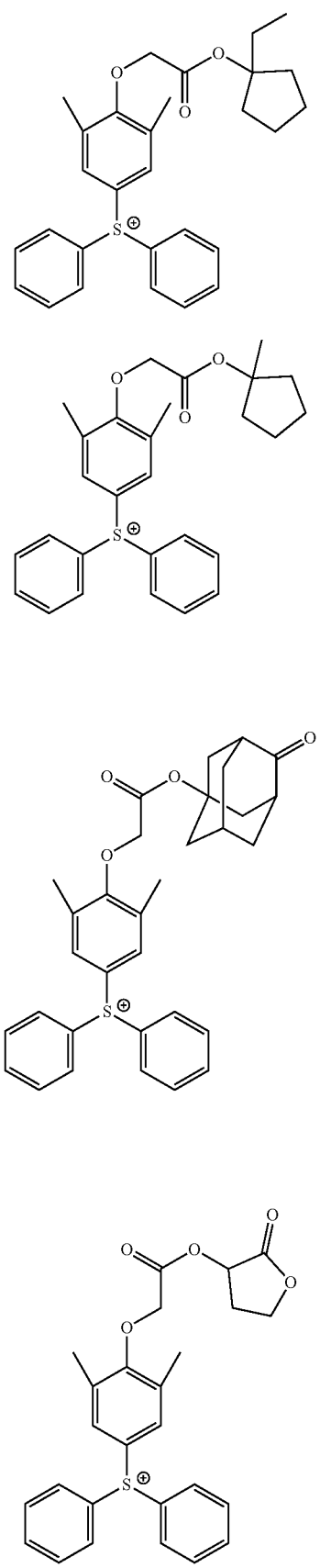
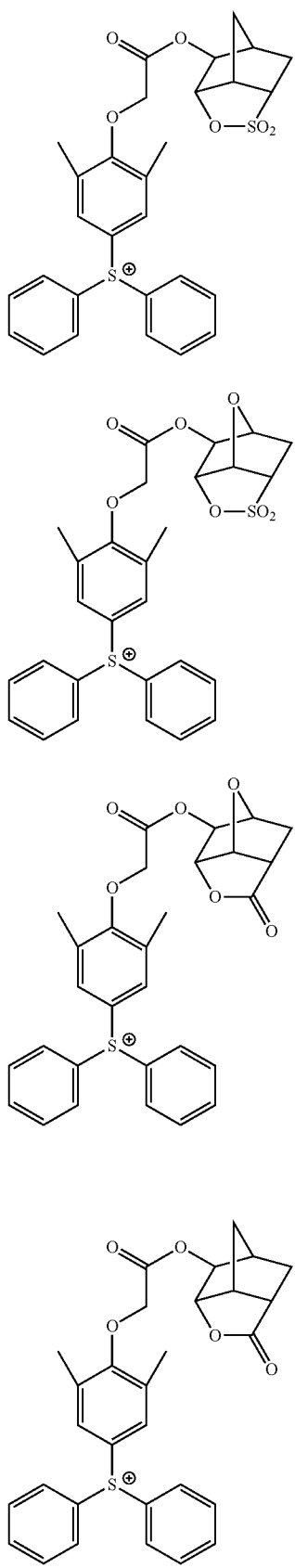

(ca-1-27)
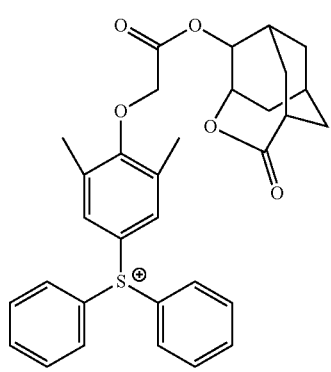
(ca-1-28)
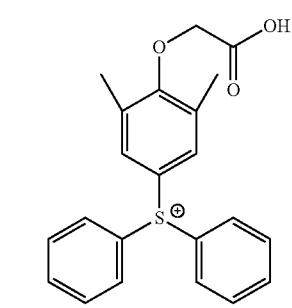
(ca-1-29)
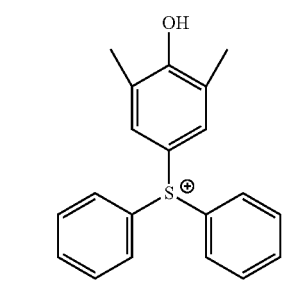
(ca-1-30)
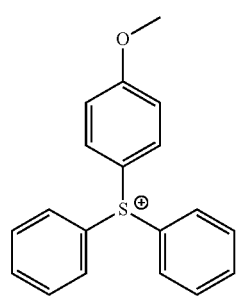
(ca-1-31)
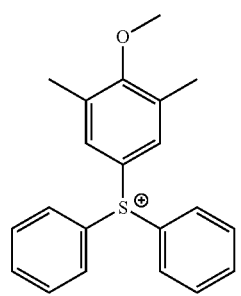
(ca-1-32)
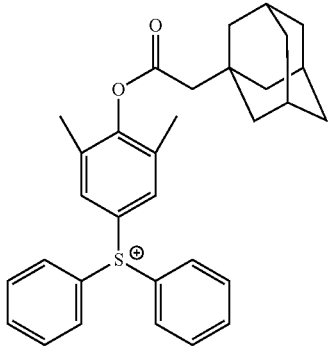
(ca-1-33)
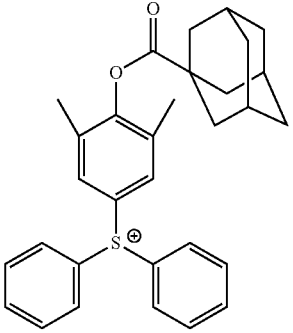
[Chemical Formula 63.]
(ca-1-34)
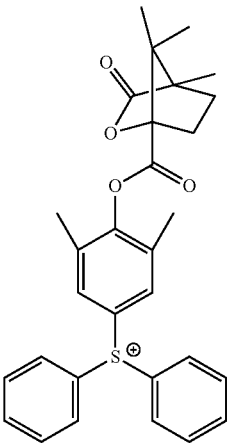
(ca-1-35)
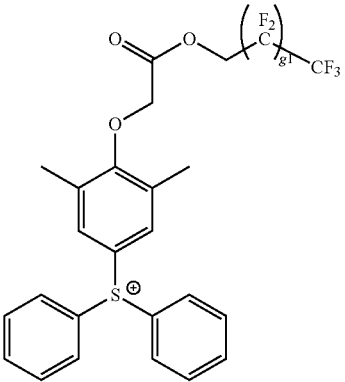

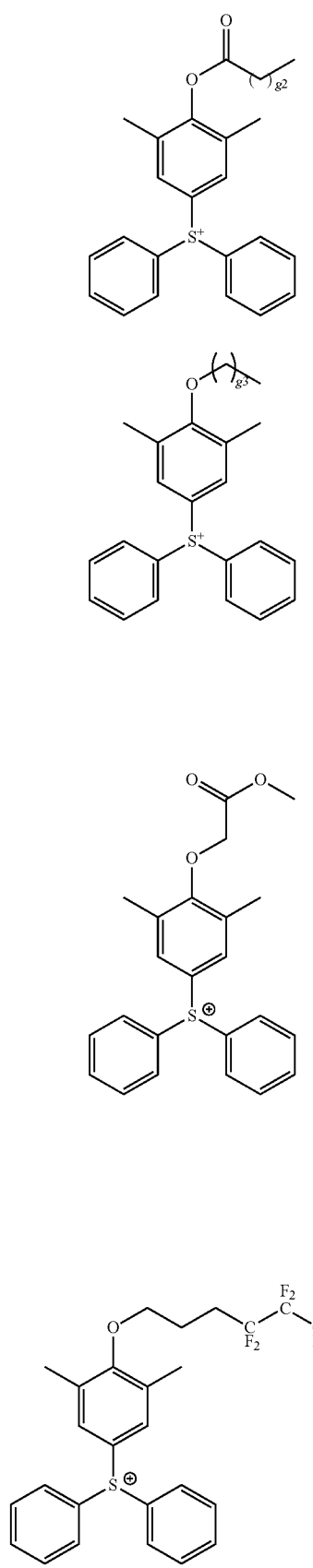
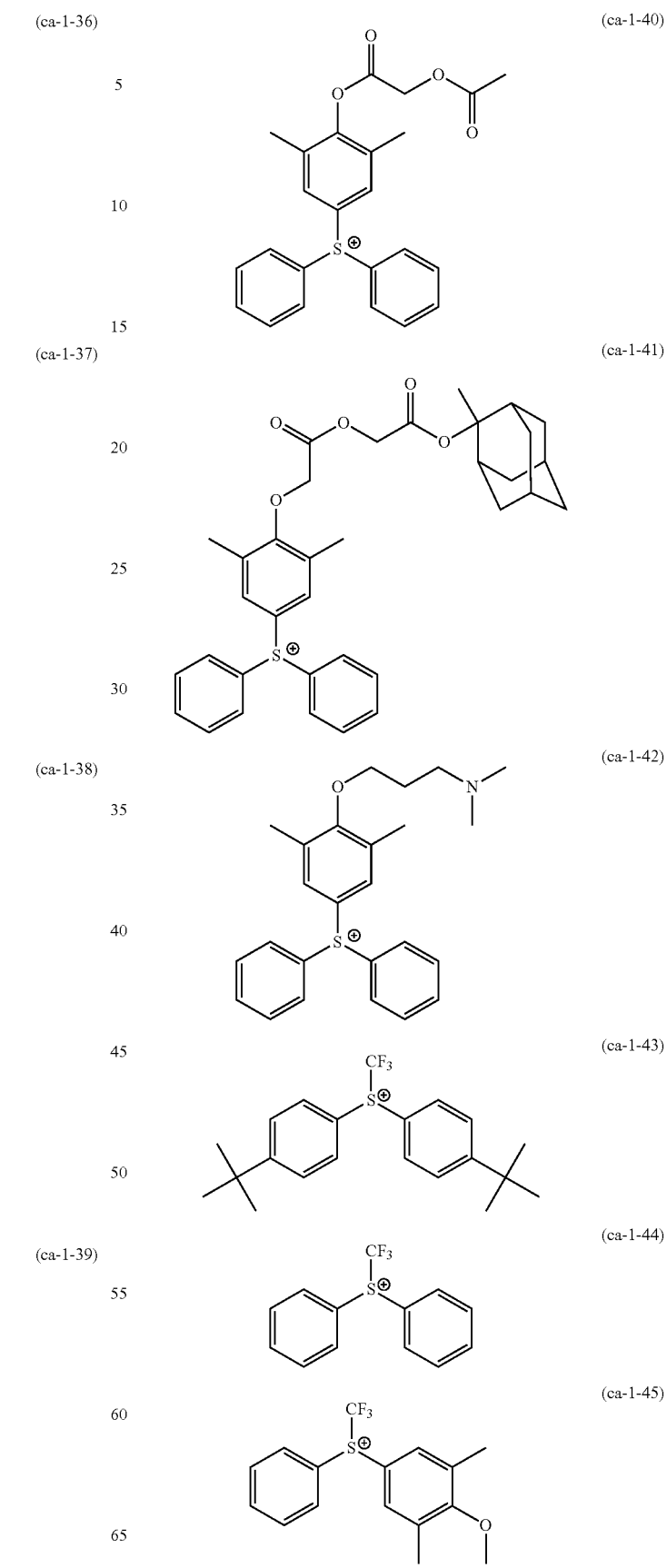

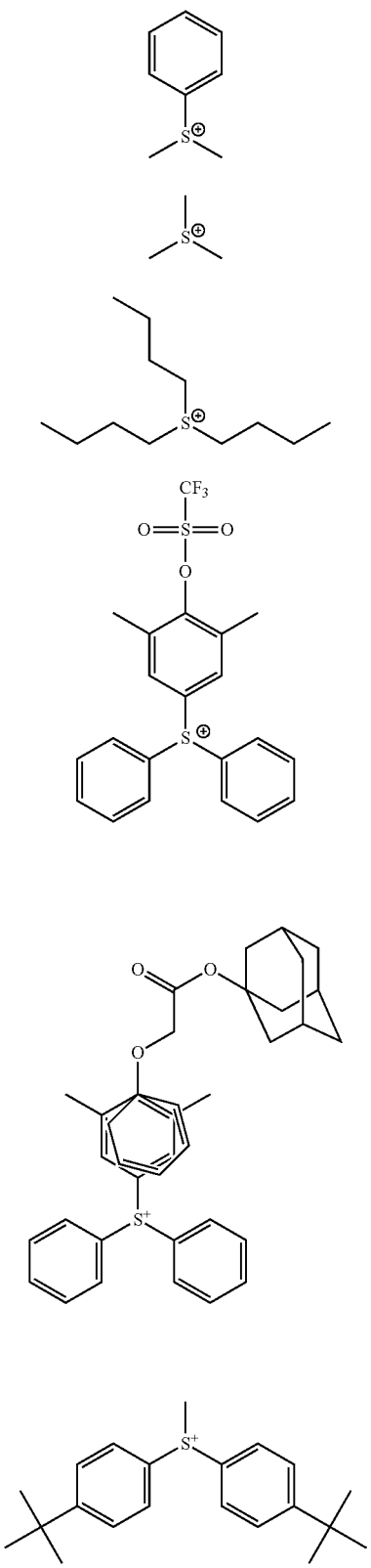
In the formulae, g1, g2 and g3 represent recurring numbers, wherein g1 is an integer of 1 to 5, g2 is an integer of 0 to 20, and g3 is an integer of 0 to 20.
[Chemical Formula 64.]

(ca-1-57)
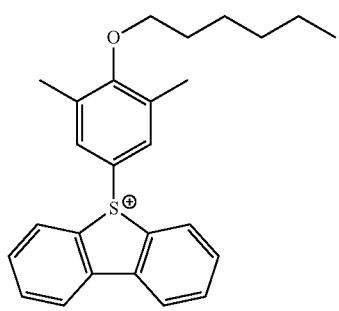
(ca-1-58)
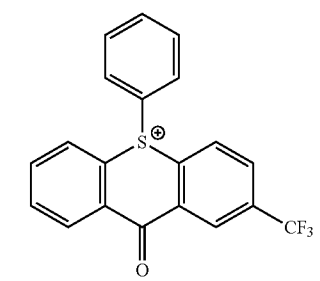
(ca-1-59)
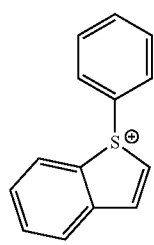
(ca-1-60)
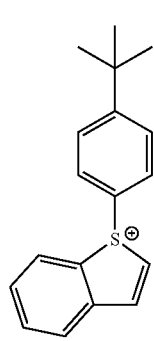
(ca-1-61)
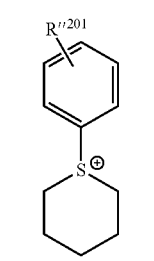
(ca-1-62)
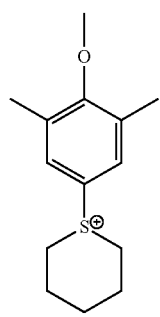
(ca-1-63)
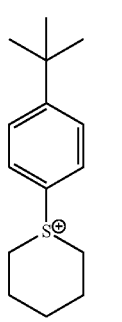
(ca-1-64)
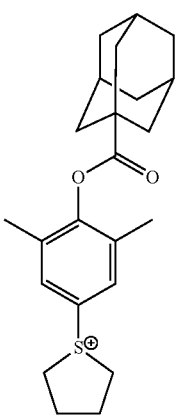
(ca-1-65)
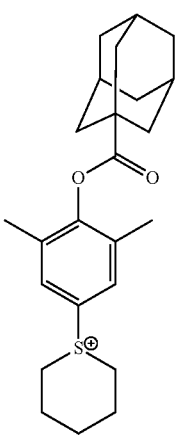

-continued (ca-1-66)

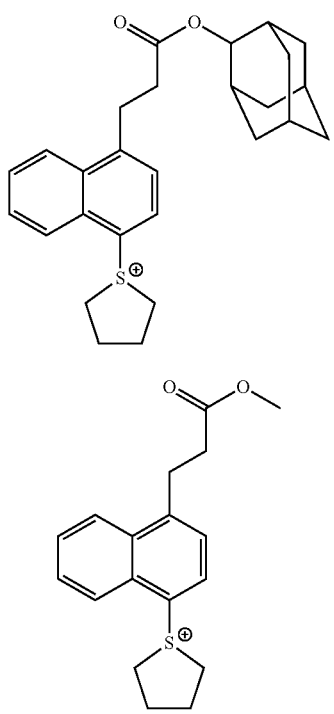

[Chemical Formula 65.]

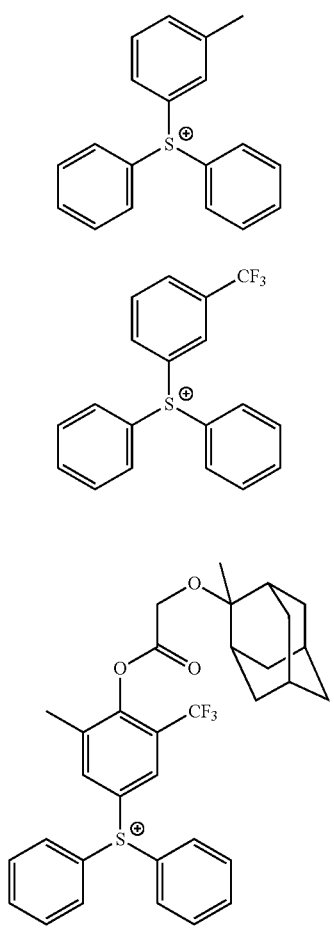

-continued (ca-1-71)

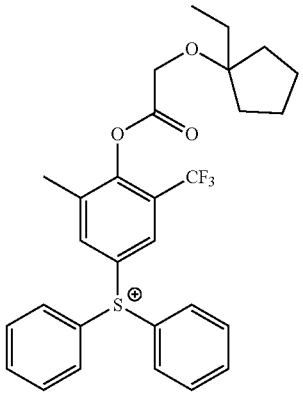

In the formulae, $R''^{201}$ represents a hydrogen atom or a substituent, and as the substituent, the same groups as those described above for substituting $R^{201}$ to $R^{207}$ and $R^{210}$ to $R^{212}$ can be mentioned.

Specific examples of preferable cations represented by the formula (ca-2) include a dihphenyliodonium cation and a bis(4-tert-butylphenyl)iodonium cation.

Specific examples of preferable cations represented by formula (ca-3) include cations represented by formulae (ca-3-1) to (ca-3-6) shown below.

[Chemical Formula 66.]

(ca-3-1)

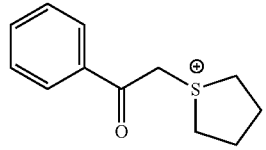

(ca-3-2)

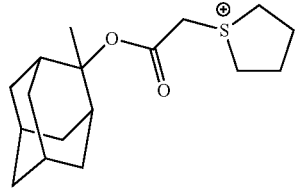

(ca-3-3)

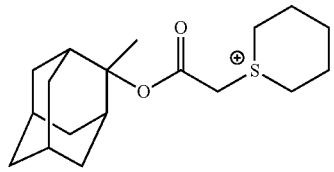

(ca-3-4)

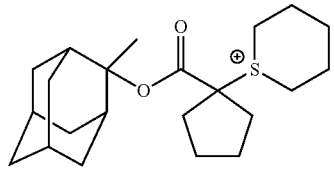

(ca-3-5)

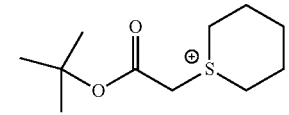

-continued (ca-3-6)

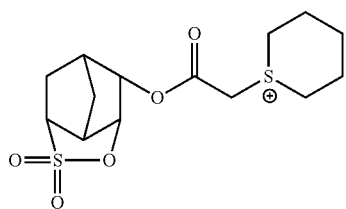

Specific examples of preferable cations represented by formula (ca-4) include cations represented by formulae (ca-4-1) and (ca-4-2) shown below.

[Chemical Formula 67.]

(ca-4-1)

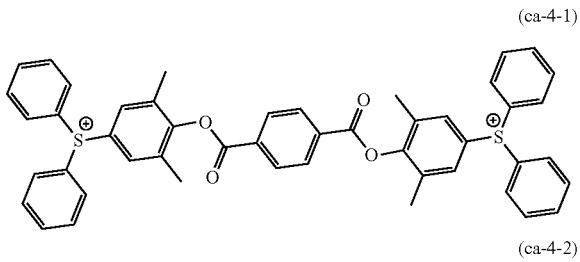

(ca-4-2)

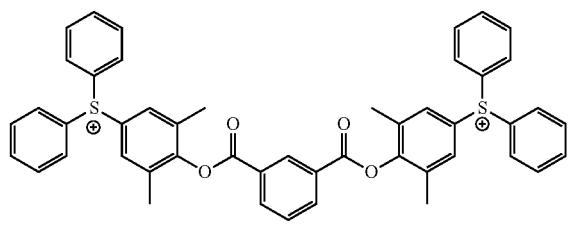

Among the above examples, as the cation moiety (($M'^{m+}$)$_{1/m}$), a cation represented by general formula (ca-1) is preferable, and a cation represented by any one of formulae (ca-1-1) to (ca-1-71) is more preferable.

In the resist composition of the present embodiment, as the component (B2), one kind of compound may be used, or two or more kinds of compounds may be used in combination.

When the resist composition contains the component (B2), the amount of the component (B2) relative to 100 parts by weight of the component (A) is preferably 50 parts by weight or less, more preferably 1 to 40 parts by weight, and still more preferably 5 to 30 parts by weight.

When the amount of the component (B2) is within the above-mentioned range, formation of a resist pattern may be satisfactorily performed.

<<Acid Diffusion Control Agent (D)>>

The resist composition according to the present embodiment may include an acid diffusion control agent component (hereafter, sometimes referred to as "component (D)"), in addition to the component (A), or in addition to the component (A) and the component (B). The component (D) functions as an acid diffusion control agent, i.e., a quencher which traps the acid generated in the resist composition upon exposure.

The component (D) may be a photodecomposable base (D1) (hereafter, referred to as "component (D1)") which is decomposed upon exposure and then loses the ability of controlling of acid diffusion, or a nitrogen-containing organic compound (D2) (hereafter, referred to as "component (D2)") which does not fall under the definition of component (D1).

Component (D1)

When a resist pattern is formed using a resist composition containing the component (D1), the contrast between exposed portions and unexposed portions of the resist film is improved.

The component (D1) is not particularly limited, as long as it is decomposed upon exposure and then loses the ability of controlling of acid diffusion. As the component (D1), at least one compound selected from the group consisting of a compound represented by general formula (d1-1) shown below (hereafter, referred to as "component (d1-1)"), a compound represented by general formula (d1-2) shown below (hereafter, referred to as "component (d1-2)") and a compound represented by general formula (d1-3) shown below (hereafter, referred to as "component (d1-3)") is preferably used.

At exposed portions of the resist film, the components (d1-1) to (d1-3) are decomposed and then lose the ability of controlling of acid diffusion (i.e., basicity), and therefore the components (d1-1) to (d1-3) cannot function as a quencher, whereas at unexposed portions, the components (d1-1) to (d1-3) functions as a quencher.

[Chemical Formula 68.]

(d1-1)

(d1-2)

(d1-3)
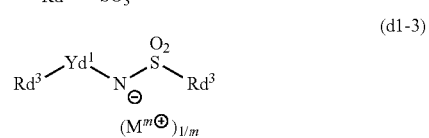

In the formulae, $Rd^1$ to $Rd^4$ represent a cyclic group which may have a substituent, a chain-like alkyl group which may have a substituent or a chain-like alkenyl group which may have a substituent, provided that, the carbon atom adjacent to the sulfur atom within the $Rd^2$ in the formula (d1-2) has no fluorine atom bonded thereto; $Yd^1$ represents a single bond or a divalent linking group; m represents an integer of 1 or more; and each $M^{m+}$ independently represents an organic cation having a valency of m.

Cation Moiety

In the aforementioned formulae, each $M^{m+}$ independently represents a m-valent organic cation.

In the present specification, regarding the m-valent organic cation in formulae (d1-1) to (d1-3), a component (D1) which has the same cation as in general formula (b1) is sometimes referred to as component (D11).

A component (D1) which does not have the same cation as in general formula (b1) is sometimes referred to as component (D12).

In the resist composition of the present embodiment, as the component (D1), either of the component (D11) and the component (D12) may be used alone, or two or more kinds may be used.

Examples of the m-valent organic cation represented by $M^{m+}$ include the same organic cation as the cation moiety in the aforementioned general formula (b1), and an organic cation represented by the aforementioned general formulae (ca-1) to (ca-4).

{Component (d1-1)}

Anion Moiety

In formula (d1-1), $Rd^1$ represents a cyclic group which may have a substituent, a chain-like alkyl group which may have a substituent or a chain-like alkenyl group which may have a substituent, and is the same groups as those defined above for $R^{101}$ in the aforementioned formula (b-1).

Among these, as the group for $Rd^1$, an aromatic hydrocarbon group which may have a substituent, an aliphatic cyclic group which may have a substituent and a chain-like alkyl group which may have a substituent are preferable. Examples of the substituent for these groups include a hydroxy group, an oxo group, an alkyl group, an aryl group, a fluorine atom, a fluorinated alkyl group, a lactone-containing cyclic group represented by any one of the aforementioned formulae (a2-r-1) to (a2-r-7), an ether bond, an ester bond, and a combination thereof. In the case where an ether bond or an ester bond is included as the substituent, the substituent may be bonded via an alkylene group, and a linking group represented by any one of the aforementioned formulae (y-a1-1) to (y-a1-5) is preferable as the substituent.

Preferable examples of the aromatic hydrocarbon group include a phenyl group, a naphthyl group, and a polycyclic structure (for example, a polycyclic structure formed of a ring structure having a bicyclooctane skeleton and a ring structure other than the bicyclooctane skeleton) containing a bicyclooctane skeleton.

Examples of the aliphatic cyclic group include groups in which one or more hydrogen atoms have been removed from a polycycloalkane such as adamantane, norbornane, isobornane, tricyclodecane or tetracyclododecane.

The chain-like alkyl group preferably has 1 to 10 carbon atoms, and specific examples thereof include a linear alkyl group such as a methyl group, an ethyl group, a propyl group, a butyl group, a pentyl group, a hexyl group, a heptyl group, an octyl group, a nonyl or a decyl group, and a branched alkyl group such as a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group or a 4-methylpentyl group.

In the case where the chain-like alkyl group is a fluorinated alkyl group having a fluorine atom or a fluorinated alkyl group, the fluorinated alkyl group preferably has 1 to 11 carbon atoms, more preferably 1 to 8 carbon atoms, and still more preferably 1 to 4 carbon atoms. The fluorinated alkyl group may contain an atom other than fluorine. Examples of the atom other than fluorine include an oxygen atom, a sulfur atom and a nitrogen atom.

As $Rd^1$, a fluorinated alkyl group in which part or all of the hydrogen atoms constituting a linear alkyl group have been substituted with fluorine atom(s) is preferable, and a fluorinated alkyl group in which all of the hydrogen atoms constituting a linear alkyl group have been substituted with fluorine atoms (i.e., a linear perfluoroalkyl group) is particularly desirable.

Specific examples of preferable anion moieties for the component (d1-1) are shown below.

[Chemical Formula 69.]

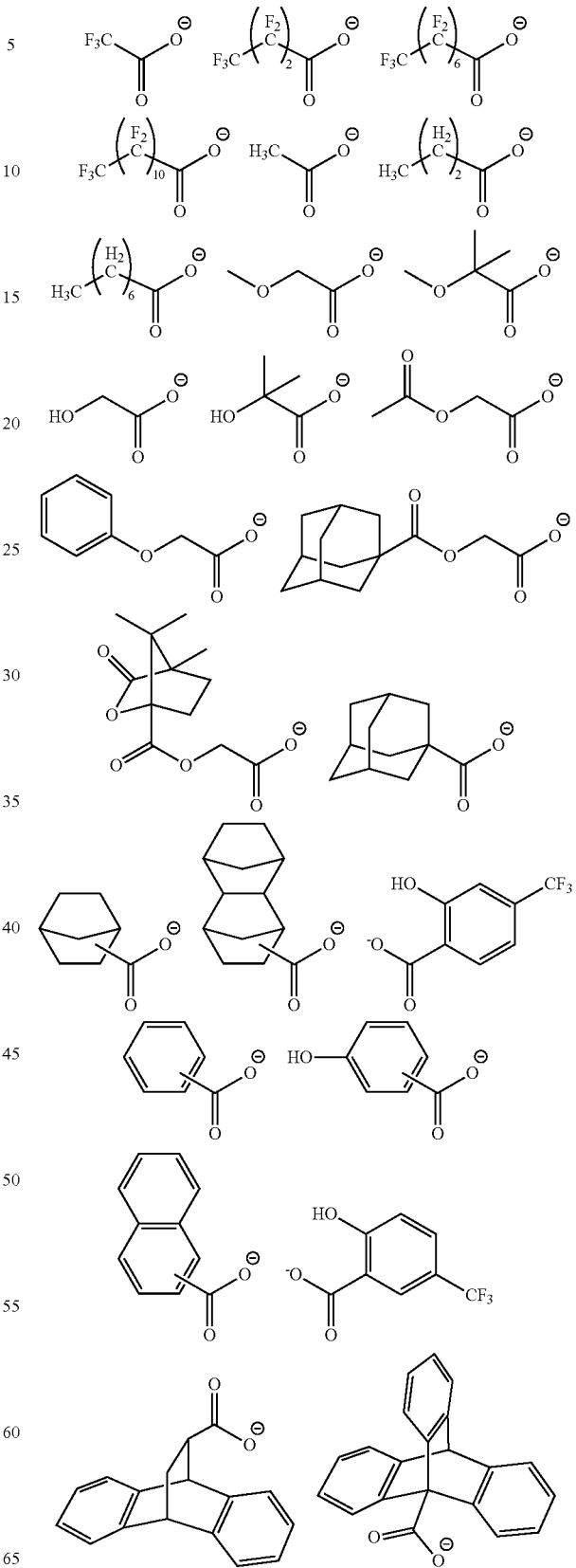

As the component (d1-1), one kind of compound may be used, or two or more kinds of compounds may be used in combination.

{Component (d1-2)}

Anion Moiety

In formula (d1-2), $Rd^2$ represents a cyclic group which may have a substituent, a chain-like alkyl group which may have a substituent or a chain-like alkenyl group which may have a substituent, and is the same groups as those defined above for $R^{101}$ in the aforementioned formula (b-1).

However, the carbon atom adjacent to the sulfur atom within $Rd^2$ group has no fluorine atom bonded thereto (i.e., the carbon atom adjacent to the sulfur atom within $Rd^2$ group does not substituted with a fluorine atom). As a result, the anion of the component (d1-2) becomes an appropriately weak acid anion, thereby improving the quenching ability of the component (D).

As $Rd^2$, a chain-like alkyl group which may have a substituent or an aliphatic cyclic group which may have a substituent is preferable. The chain-like alkyl group preferably has 1 to 10 carbon atoms, and more preferably 3 to 10 carbon atoms. As the aliphatic cyclic group, a group in which one or more hydrogen atoms have been removed from adamantane, norbornane, isobornane, tricyclodecane, tetracyclododecane or camphor (which may have a substituent) is more preferable.

The hydrocarbon group for $Rd^2$ may have a substituent. As the substituent, the same groups as those described above for substituting the hydrocarbon group (e.g., aromatic hydrocarbon group, aliphatic cyclic group, chain-like alkyl group) for $Rd^1$ in the formula (d1-1) can be mentioned.

Specific examples of preferable anion moieties for the component (d1-2) are shown below.

[Chemical Formula 70.]

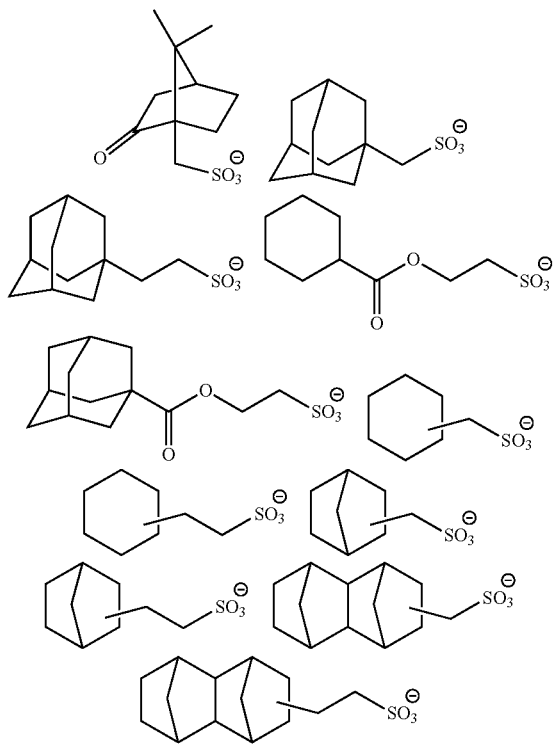

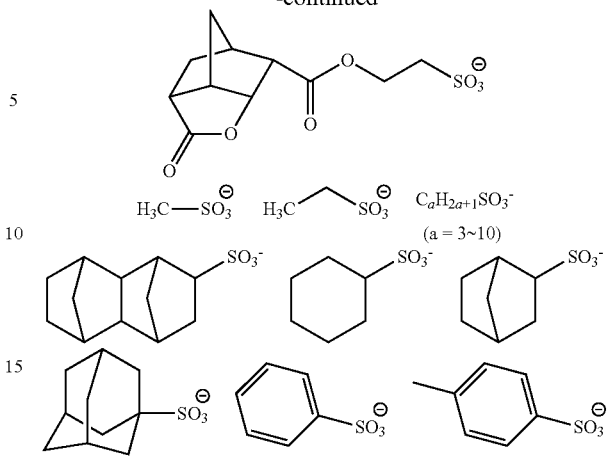

As the component (d1-2), one type of compound may be used, or two or more types of compounds may be used in combination.

{Component (d1-3)}

Anion Moiety

In formula (d1-3), $Rd^3$ represents a cyclic group which may have a substituent, a chain-like alkyl group which may have a substituent or a chain-like alkenyl group which may have a substituent, and is the same groups as those defined above for $R^{101}$ in the aforementioned formula (b-1), and a cyclic group containing a fluorine atom, a chain-like alkyl group or a chain-like alkenyl group is preferable. Among these, a fluorinated alkyl group is preferable, and more preferably the same fluorinated alkyl groups as those described above for $Rd^1$.

In formula (d1-3), $Rd^4$ represents a cyclic group which may have a substituent, a chain-like alkyl group which may have a substituent or a chain-like alkenyl group which may have a substituent, and is the same groups as those defined above for $R^{101}$ in the aforementioned formula (b-1).

Among these, an alkyl group which may have substituent, an alkoxy group which may have substituent, an alkenyl group which may have substituent or a cyclic group which may have substituent is preferable.

The alkyl group for $Rd^4$ is preferably a linear or branched alkyl group of 1 to 5 carbon atoms, and specific examples include a methyl group, an ethyl group, a propyl group, an isopropyl group, an n-butyl group, an isobutyl group, a tert-butyl group, a pentyl group, an isopentyl group, and a neopentyl group. Part of the hydrogen atoms within the alkyl group for $Rd^4$ may be substituted with a hydroxy group, a cyano group or the like.

The alkoxy group for $Rd^4$ is preferably an alkoxy group of 1 to 5 carbon atoms, and specific examples thereof include a methoxy group, an ethoxy group, an n-propoxy group, an iso-propoxy group, an n-butoxy group and a tert-butoxy group. Among these, a methoxy group and an ethoxy group are preferable.

As the alkenyl group for $Rd^4$, the same groups as those described above for $R^{101}$ in the aforementioned formula (b-1) can be mentioned, and a vinyl group, a propenyl group (an allyl group), a 1-methylpropenyl group and a 2-methylpropenyl group are preferable. These groups may have an alkyl group of 1 to 5 carbon atoms or a halogenated alkyl group of 1 to 5 carbon atoms as a substituent.

As the cyclic group for $Rd^4$, the same groups as those described above for $R^{101}$ in the aforementioned formula (b-1) can be mentioned. Among these, as the cyclic group, an alicyclic group (e.g., a group in which one or more hydrogen atoms have been removed from a cycloalkane such as cyclopentane, cyclohexane, adamantane, norbornane, isobornane, tricyclodecane or tetracyclododecane) or an aromatic group (e.g., a phenyl group or a naphthyl group) is preferable. When $Rd^4$ is an alicyclic group, the resist composition can be satisfactorily dissolved in an organic solvent, thereby improving the lithography properties.

In formula (d1-3), $Yd^1$ represents a single bond or a divalent linking group.

The divalent linking group for $Yd^1$ is not particularly limited, and examples thereof include a divalent hydrocarbon group (aliphatic hydrocarbon group, or aromatic hydrocarbon group) which may have a substituent and a divalent linking group containing a hetero atom. The divalent linking groups are the same as defined for the divalent hydrocarbon group which may have a substituent and the divalent linking group containing a hetero atom explained above as the divalent linking group for $Ya^{21}$ in the aforementioned formula (a2-1).

As $Yd^1$, a carbonyl group, an ester bond, an amide bond, an alkylene group or a combination of these is preferable. As the alkylene group, a linear or branched alkylene group is more preferable, and a methylene group or an ethylene group is still more preferable.

Specific examples of preferable anion moieties for the component (d1-3) are shown below.

[Chemical Formula 71.]

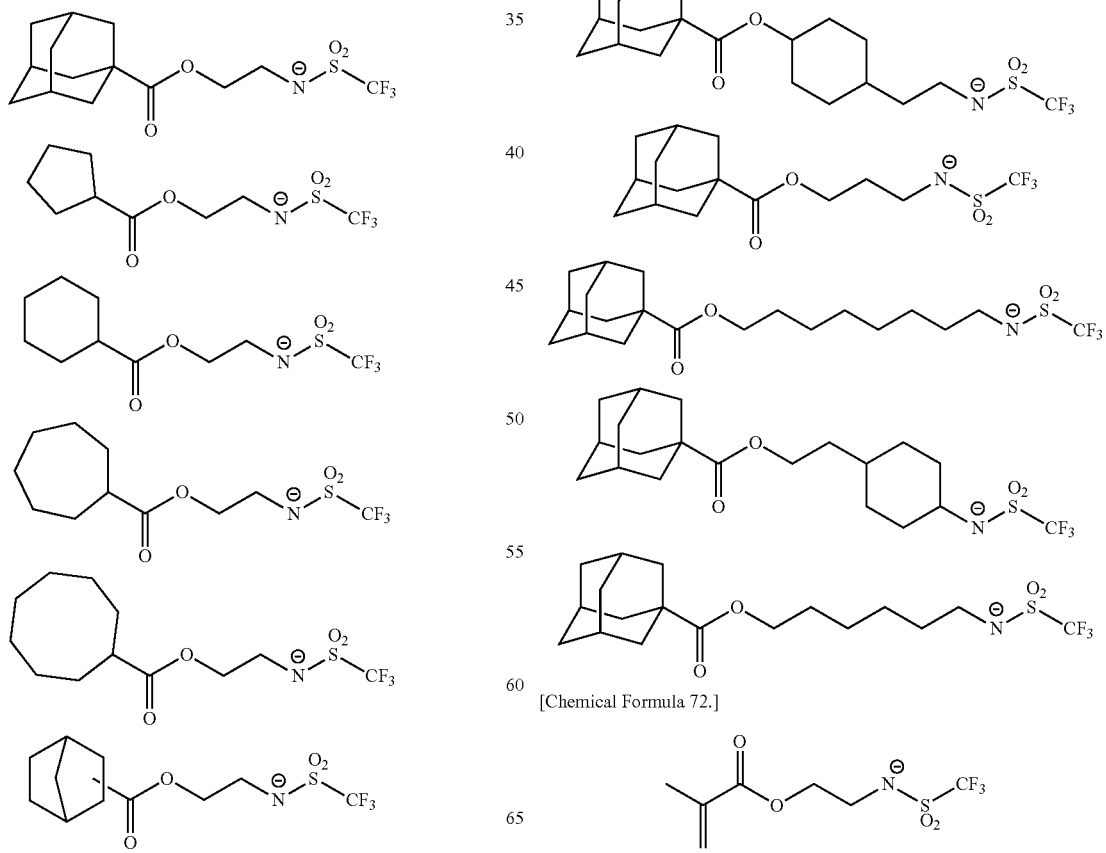

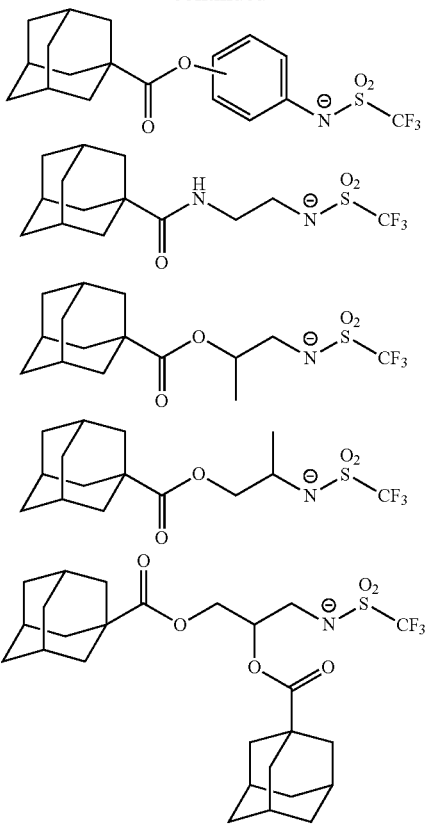

[Chemical Formula 72.]

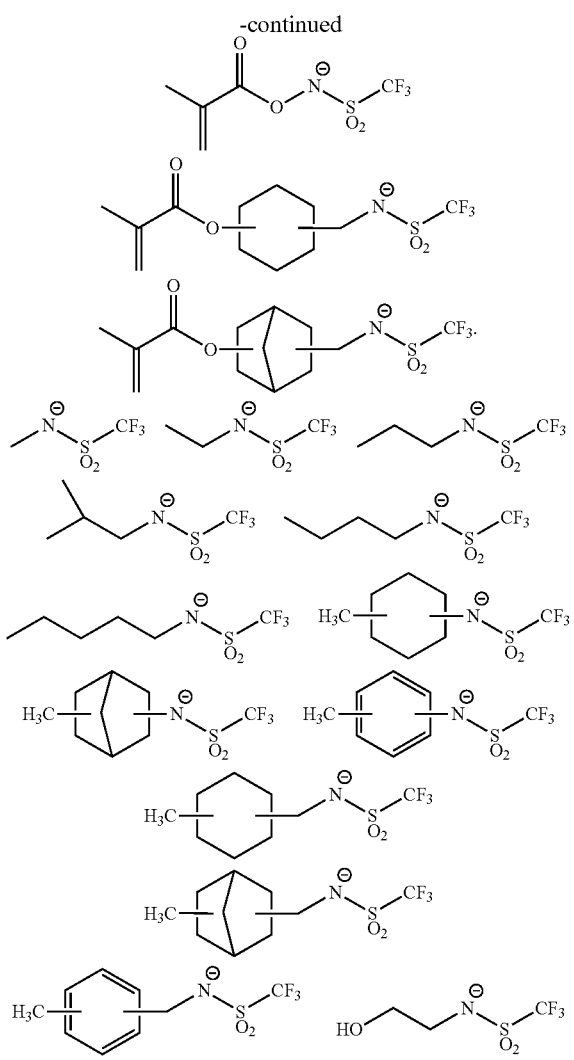

As the component (d1-3), one type of compound may be used, or two or more types of compounds may be used in combination.

As the component (D1), one type of the aforementioned components (d1-1) to (d1-3), or at least two types of the aforementioned components (d1-1) to (d1-3) can be used in combination.

When the resist composition contains the component (D1), the amount of the component (D1) relative to 100 parts by weight of the component (A) is preferably within a range from 0.5 to 35 parts by weight, more preferably from 1 to 25 parts by weight, and still more preferably from 2 to 20 parts by weight.

When the amount of the component (D1) is at least as large as the lower limit of the above-mentioned range, excellent lithography properties and excellent resist pattern shape can be more reliably obtained. On the other hand, when the amount of the component (D1) is no more than the upper limit of the above-mentioned range, sensitivity can be maintained at a satisfactory level, and through-put becomes excellent.

Production Method of Component (D1):

The production methods of the components (d1-1) and (d1-2) are not particularly limited, and the components (d1-1) and (d1-2) can be produced by conventional methods.

Further, the production method of the component (d1-3) is not particularly limited, and the component (d1-3) can be produced in the same manner as disclosed in US2012-0149916.

Component (D2)

The acid diffusion control component may contain a nitrogen-containing organic compound (D2) (hereafter, referred to as component (D2)) which does not fall under the definition of component (D1).

The component (D2) is not particularly limited, as long as it functions as an acid diffusion control agent, and does not fall under the definition of the component (D1). As the component (D2), any of the conventionally known compounds may be selected for use. Among these, an aliphatic amine is preferable, and a secondary aliphatic amine or tertiary aliphatic amine is more preferable.

An aliphatic amine is an amine having one or more aliphatic groups, and the aliphatic groups preferably have 1 to 12 carbon atoms.

Examples of these aliphatic amines include amines in which at least one hydrogen atom of ammonia ($NH_3$) has been substituted with an alkyl group or hydroxyalkyl group of no more than 12 carbon atoms (i.e., alkylamines or alkylalcoholamines), and cyclic amines.

Specific examples of alkylamines and alkylalcoholamines include monoalkylamines such as n-hexylamine, n-heptylamine, n-octylamine, n-nonylamine, and n-decylamine; dialkylamines such as diethylamine, di-n-propylamine, di-n-heptylamine, di-n-octylamine, and dicyclohexylamine; trialkylamines such as trimethylamine, triethylamine, tri-n-propylamine, tri-n-butylamine, tri-n-hexylamine, tri-n-pentylamine, tri-n-heptylamine, tri-n-octylamine, tri-n-nonylamine, tri-n-decylamine, and tri-n-dodecylamine; and alkyl alcohol amines such as diethanolamine, triethanolamine, diisopropanolamine, triisopropanolamine, di-n-octanolamine, and tri-n-octanolamine. Among these, trialkylamines of 5 to 10 carbon atoms are preferable, and tri-n-pentylamine and tri-n-octylamine are particularly desirable.

Examples of the cyclic amine include heterocyclic compounds containing a nitrogen atom as a hetero atom. The heterocyclic compound may be a monocyclic compound (aliphatic monocyclic amine), or a polycyclic compound (aliphatic polycyclic amine).

Specific examples of the aliphatic monocyclic amine include piperidine, and piperazine.

The aliphatic polycyclic amine preferably has 6 to 10 carbon atoms, and specific examples thereof include 1,5-diazabicyclo[4.3.0]-5-nonene, 1,8-diazabicyclo[5.4.0]-7-undecene, hexamethylenetetramine, and 1,4-diazabicyclol[2.2.2]octane.

Examples of other aliphatic amines include tris(2-methoxymethoxyethyl)amine, tris{2-(2-methoxyethoxy)ethyl}amine, tris{2-(2-methoxyethoxymethoxy)ethyl}amine, tris{2-(1-methoxyethoxy)ethyl}amine, tris{2-(1-ethoxyethoxy)ethyl}amine, tris{2-(1-ethoxypropoxy)ethyl}amine, tris[2-{2-(2-hydroxyethoxy)ethoxy}ethyl]amine and triethanolamine triacetate, and triethanolamine triacetate is preferable.

Further, as the component (D2), an aromatic amine may be used.

Examples of aromatic amines include 4-dimethylaminopyridine, pyrrole, indole, pyrazole, imidazole and derivatives thereof, as well as tribenzylamine, 2,6-diisopropylaniline and N-tert-butoxycarbonylpyrrolidine.

As the component (D2), one type of compound may be used alone, or two or more types may be used in combination.

When the resist composition contains the component (D2), the amount of the component (D2) is typically used in an amount within a range from 0.01 to 5 parts by weight, relative to 100 parts by weight of the component (A). When the amount of the component (D) is within the above-mentioned range, the shape of the resist pattern and the post exposure stability of the latent image formed by the pattern-wise exposure of the resist layer are improved.

<<Component (E): At Least One Compound Selected from the Group Consisting of Organic Carboxylic Acids, and Phosphorus Oxo Acids and Derivatives Thereof>>

In the resist composition of the present embodiment, for preventing any deterioration in sensitivity, and improving the resist pattern shape and the post exposure stability of the latent image formed by the pattern-wise exposure of the resist layer, at least one compound (E) (hereafter referred to as the component (E)) selected from the group consisting of an organic carboxylic acid, or a phosphorus oxo acid or derivative thereof may be added.

Examples of suitable organic carboxylic acids include acetic acid, malonic acid, citric acid, malic acid, succinic acid, benzoic acid, and salicylic acid.

Examples of phosphorus oxo acids include phosphoric acid, phosphonic acid and phosphinic acid. Among these, phosphonic acid is particularly desirable.

Examples of oxo acid derivatives include esters in which a hydrogen atom within the above-mentioned oxo acids is substituted with a hydrocarbon group. Examples of the hydrocarbon group include an alkyl group of 1 to 5 carbon atoms and an aryl group of 6 to 15 carbon atoms.

Examples of phosphoric acid derivatives include phosphoric acid esters such as di-n-butyl phosphate and diphenyl phosphate.

Examples of phosphonic acid derivatives include phosphonic acid esters such as dimethyl phosphonate, di-n-butyl phosphonate, phenylphosphonic acid, diphenyl phosphonate and dibenzyl phosphonate.

Examples of phosphinic acid derivatives include phosphinic acid esters and phenylphosphinic acid.

In the resist composition of the present embodiment, as the component (E), one kind of compound may be used, or two or more kinds of compounds may be used in combination.

When the resist composition contains the component (E), the amount of the component (E) is typically used in an amount within a range from 0.01 to 5 parts by weight, relative to 100 parts by weight of the component (A).

<<Component (F): Fluorine Additive>>

In the present embodiment, the resist composition may further include a fluorine additive (hereafter, referred to as "component (F)") for imparting water repellency to the resist film, or improving lithography properties.

As the component (F), for example, a fluorine-containing polymeric compound described in Japanese Unexamined Patent Application, First Publication No. 2010-002870, Japanese Unexamined Patent Application, First Publication No. 2010-032994, Japanese Unexamined Patent Application, First Publication No. 2010-277043, Japanese Unexamined Patent Application, First Publication No. 2011-13569, and Japanese Unexamined Patent Application, First Publication No. 2011-128226 can be used.

Specific examples of the component (F) include polymers having a structural unit (f1) represented by general formula (f1-1) shown below. As the polymer, a polymer (homopolymer) consisting of a structural unit (f1) represented by formula (f1-1) shown below; a copolymer of the structural unit (f1) and the aforementioned structural unit (a1); and a copolymer of the structural unit (f1), a structural unit derived from acrylic acid or methacrylic acid and the aforementioned structural unit (a1) are preferable. As the structural unit (a1) to be copolymerized with the structural unit (f1), a structural unit derived from 1-ethyl-1-cyclooctyl (meth)acrylate or a structural unit derived from 1-methyl-1-adamantyl (meth)acrylate is preferable.

[Chemical Formula 73.]

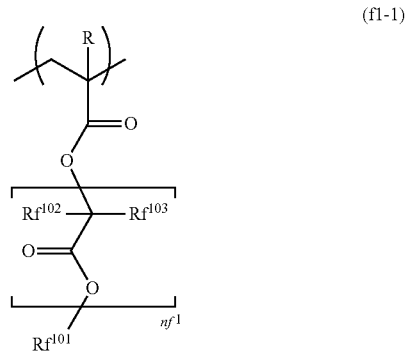

(f1-1)

In the formula, R is the same as defined above: $Rf^{102}$ and $Rf^{103}$ each independently represents a hydrogen atom, a halogen atom, an alkyl group of 1 to 5 carbon atoms, or a halogenated alkyl group of 1 to 5 carbon atoms, provided that $Rf^{102}$ and $Rf^{103}$ may be the same or different; $nf^1$ represents an integer of 1 to 5; and $Rf^{101}$ represents an organic group containing a fluorine atom.

In formula (f1-1), R bonded to the carbon atom on the α-position is the same as defined above. As R, a hydrogen atom or a methyl group is preferable.

In formula (f1-1), examples of the halogen atom for $Rf^{102}$ and $Rf^{103}$ include a fluorine atom, a chlorine atom, a bromine atom and an iodine atom, and a fluorine atom is particularly desirable. Examples of the alkyl group of 1 to 5 carbon atoms for $Rf^{102}$ and $Rf^{103}$ include the same alkyl group of 1 to 5 carbon atoms as those described above for R, and a methyl group or an ethyl group is preferable. Specific examples of the halogenated alkyl group of 1 to 5 carbon atoms represented by $Rf^{102}$ or $Rf^{103}$ include groups in which part or all of the hydrogen atoms of the aforementioned alkyl groups of 1 to 5 carbon atoms have been substituted with halogen atoms.

Examples of the halogen atom include a fluorine atom, a chlorine atom, a bromine atom and an iodine atom, and a fluorine atom is particularly desirable. Among these examples, as $Rf^{102}$ and $Rf^{103}$, a hydrogen atom, a fluorine atom or an alkyl group of 1 to 5 carbon atoms is preferable, and a hydrogen atom, a fluorine atom, a methyl group or an ethyl group is more preferable.

In formula (f1-1), $nf^1$ represents an integer of 1 to 5, preferably an integer of 1 to 3, and more preferably 1 or 2.

In formula (f1-1), $Rf^{101}$ represents an organic group containing a fluorine atom, and is preferably a hydrocarbon group containing a fluorine atom.

The hydrocarbon group containing a fluorine atom may be linear, branched or cyclic, and preferably has 1 to 20 carbon atoms, more preferably 1 to 15 carbon atoms, and most preferably 1 to 10 carbon atoms.

It is preferable that the hydrocarbon group having a fluorine atom has 25% or more of the hydrogen atoms within the hydrocarbon group fluorinated, more preferably 50% or more, and most preferably 60% or more, as the hydrophobicity of the resist film during immersion exposure is enhanced.

Among these, as $Rf^{101}$, a fluorinated hydrocarbon group of 1 to 6 carbon atoms is preferable, and a trifluoromethyl group, —$CH_2$—$CF_3$, —$CH_2$—$CF_2$—$CF_3$, —$CH(CF_3)_2$, —$CH_2$—$CH_2$—$CF_3$, and —$CH_2$—$CH_2$—$CF_2$—$CF_2$—$CF_2$—$CF_3$ are most preferable.

The weight average molecular weight (Mw) (the polystyrene equivalent value determined by gel permeation chromatography) of the component (F) is preferably 1,000 to 50,000, more preferably 5,000 to 40,000, and most preferably 10,000 to 30,000. When the weight average molecular weight (Mw) is no more than the upper limit of the above-mentioned range, the resist may exhibit satisfactory solubility in a resist solvent. On the other hand, when the weight average molecular weight (Mw) is at least as large as the lower limit of the above-mentioned range, the water repellency of the resist film may become satisfactory.

Further, the dispersity (Mw/Mn) of the component (F) is preferably 1.0 to 5.0, more preferably 1.0 to 3.0, and most preferably 1.2 to 2.5.

In the resist composition of the present embodiment, as the component (F), one kind of compound may be used, or two or more kinds of compounds may be used in combination.

When the resist composition contains the component (F), the component (F) is used in an amount within a range from 0.5 to 10 parts by weight, relative to 100 parts by weight of the component (A).

<<Component (S): Organic Solvent>>

The resist composition of the present embodiment may be prepared by dissolving the resist materials for the resist composition in an organic solvent (hereafter, referred to as "component (S)").

The component (S) may be any organic solvent which can dissolve the respective components to give a homogeneous solution, and any organic solvent can be appropriately selected from those which have been conventionally known as solvents for a chemically amplified resist composition.

Examples thereof include lactones such as γ-butyrolactone; ketones such as acetone, methyl ethyl ketone, cyclohexanone, methyl-n-pentyl ketone, methyl isopentyl ketone, and 2-heptanone; polyhydric alcohols, such as ethylene glycol, diethylene glycol, propylene glycol and dipropylene glycol; compounds having an ester bond, such as ethylene glycol monoacetate, diethylene glycol monoacetate, propylene glycol monoacetate, and dipropylene glycol monoacetate; polyhydric alcohol derivatives including compounds having an ether bond, such as a monoalkylether (e.g., monomethylether, monoethylether, monopropylether or monobutylether) or monophenylether of any of these polyhydric alcohols or compounds having an ester bond (among these, propylene glycol monomethyl ether acetate (PGMEA) and propylene glycol monomethyl ether (PGME) are preferable); cyclic ethers such as dioxane; esters such as methyl lactate, ethyl lactate (EL), methyl acetate, ethyl acetate, butyl acetate, methyl pyruvate, ethyl pyruvate, methyl methoxypropionate, and ethyl ethoxypropionate; aromatic organic solvents such as anisole, ethylbenzylether, cresylmethylether, diphenylether, dibenzylether, phenetole, butylphenylether, ethylbenzene, diethylbenzene, pentylbenzene, isopropylbenzene, toluene, xylene, cymene and mesitylene; and dimethylsulfoxide (DMSO).

In the resist composition of the present embodiment, as the component (S), one kind of solvent may be used, or two or more kinds of compounds may be used as a mixed solvent.

Among these, PGMEA, PGME, γ-butyrolactone, EL and cyclohexanone are preferable.

Further, among the mixed solvents, a mixed solvent obtained by mixing PGMEA with a polar solvent is preferable. The mixing ratio (weight ratio) of the mixed solvent can be appropriately determined, taking into consideration the compatibility of the PGMEA with the polar solvent, but is preferably in the range of 1:9 to 9:1, more preferably from 2:8 to 8:2.

Specifically, when EL or cyclohexanone is mixed as the polar solvent, the PGMEA:EL or cyclohexanone weight ratio is preferably from 1:9 to 9:1, and more preferably from 2:8 to 8:2. Alternatively, when PGME is mixed as the polar solvent, the PGMEA:PGME weight ratio is preferably from 1:9 to 9:1, more preferably from 2:8 to 8:2, and still more preferably 3:7 to 7:3. Furthermore, a mixed solvent of PGMEA, PGME and cyclohexanone is also preferable.

Further, as the component (S), a mixed solvent of at least one of PGMEA and EL with γ-butyrolactone is also preferable. The mixing ratio (former:latter) of such a mixed solvent is preferably from 70:30 to 95:5.

The amount of the component (S) is not particularly limited, and is appropriately adjusted to a concentration which enables coating of a coating solution to a substrate. In general, the component (S) is used in an amount such that the solid content of the resist composition becomes within the range from 0.1 to 20% by weight, and preferably from 0.2 to 15% by weight.

If desired, other miscible additives can also be added to the resist composition of the present invention. Examples of such miscible additives include additive resins for improving the performance of the resist film, dissolution inhibitors, plasticizers, stabilizers, colorants, halation prevention agents, and dyes.

After dissolving the resist materials in the organic solvent (S), the resist composition of the present embodiment may have impurities or the like removed by using a polyimide porous film, a polyamide-imide porous film, or the like. For example, the resist composition may be subjected to filtration using a filter formed of a polyimide porous membrane, a filter formed of a polyamide-imide porous film, or a filter formed of a polyimide porous membrane and a polyamide-imide porous film. Examples of the polyimide porous membrane and the polyamide-imide porous film include those described in Japanese Unexamined Patent Application, First Publication No. 2016-155121.

The resist composition according to the present embodiment described above includes an acid generator (B1) containing a compound represented by general formula (b1).

In formula (b1), at least one of $R^{b1}$ to $R^{b3}$ is an aryl group or alkyl group having a substituent containing a halogen atom, and at least one of $R^{b1}$ to $R^{b3}$ is an aryl group or an alkyl group having a substituent containing a sulfonyl group. By virtue of the cation moiety of the component (B1) having both a substituent containing a halogen atom and a substituent containing a sulfonyl group, reactivity of the resist composition and solubility of the resist composition in a developing solution is enhanced. By virtue of including the component (B1), according to the resist composition of the present embodiment, it is presumed that lithography properties (reduced roughness) can be improved, and sensitivity can be enhanced.

(Method of Forming a Resist Pattern)

The method of forming a resist pattern according to the second aspect of the present invention includes: using a resist composition according to the first aspect to form a resist film on a substrate; exposing the resist film; and developing the exposed resist film to form a resist pattern.

The method for forming a resist pattern according to the present embodiment can be performed, for example, as follows.

Firstly, a resist composition of the first aspect is applied to a substrate using a spinner or the like, and a bake treatment (post applied bake (PAB)) is conducted at a temperature of 80 to 150° C. for 40 to 120 seconds, preferably 60 to 90 seconds, to form a resist film.

Following selective exposure of the thus formed resist film, either by exposure through a mask having a predetermined pattern formed thereon (mask pattern) using an exposure apparatus such an electron beam lithography apparatus or an EUV exposure apparatus, or by patterning via direct irradiation with an electron beam without using a mask pattern, baking treatment (post exposure baking (PEB)) is conducted under temperature conditions of 80 to 150° C. for 40 to 120 seconds, and preferably 60 to 90 seconds.

Next, the resist film is subjected to a developing treatment. The developing treatment is conducted using an alkali developing solution in the case of an alkali developing process, and a developing solution containing an organic solvent (organic developing solution) in the case of a solvent developing process.

After the developing treatment, it is preferable to conduct a rinse treatment. The rinse treatment is preferably conducted using pure water in the case of an alkali developing process, and a rinse solution containing an organic solvent in the case of a solvent developing process.

In the case of a solvent developing process, after the developing treatment or the rinsing, the developing solution or the rinse liquid remaining on the pattern can be removed by a treatment using a supercritical fluid.

After the developing treatment or the rinse treatment, drying is conducted. If desired, bake treatment (post bake) can be conducted following the developing.

In this manner, a resist pattern can be formed.

The substrate is not specifically limited and a conventionally known substrate can be used. For example, substrates for electronic components, and such substrates having wiring patterns formed thereon can be used. Specific examples of the material of the substrate include metals such as silicon wafer, copper, chromium, iron and aluminum; and glass. Suitable materials for the wiring pattern include copper, aluminum, nickel, and gold.

Further, as the substrate, any one of the above-mentioned substrates provided with an inorganic and/or organic film on the surface thereof may be used. As the inorganic film, an inorganic antireflection film (inorganic BARC) can be used. As the organic film, an organic antireflection film (organic BARC) and an organic film such as a lower-layer organic film used in a multilayer resist method can be used.

Here, a "multilayer resist method" is method in which at least one layer of an organic film (lower-layer organic film) and at least one layer of a resist film (upper resist film) are provided on a substrate, and a resist pattern formed on the upper resist film is used as a mask to conduct patterning of the lower-layer organic film. This method is considered as being capable of forming a pattern with a high aspect ratio. More specifically, in the multilayer resist method, a desired thickness can be ensured by the lower-layer organic film, and as a result, the thickness of the resist film can be reduced, and an extremely fine pattern with a high aspect ratio can be formed.

The multilayer resist method is broadly classified into a method in which a double-layer structure consisting of an upper-layer resist film and a lower-layer organic film is formed (double-layer resist method), and a method in which a multilayer structure having at least three layers consisting of an upper-layer resist film, a lower-layer organic film and at least one intermediate layer (thin metal film or the like) provided between the upper-layer resist film and the lower-layer organic film (triple-layer resist method).

The wavelength to be used for exposure is not particularly limited and the exposure can be conducted using radiation such as ArF excimer laser, KrF excimer laser, $F_2$ excimer laser, extreme ultraviolet rays (EUV), vacuum ultraviolet rays (VUV), electron beam (EB), X-rays, and soft X-rays. The resist composition of the present embodiment is effective to KrF excimer laser, ArF excimer laser, EB and EUV, and more effective to ArF excimer laser, EB and EUV, and most effective to EB and EUV. That is, the method of forming a resist pattern according to the present embodiment is effective in the case where the step of exposing the resist film includes exposing the resist film with extreme ultraviolet rays (EUV) or electron beam (EB).

The exposure of the resist film can be either a general exposure (dry exposure) conducted in air or an inert gas such as nitrogen, or immersion exposure (immersion lithography).

In immersion lithography, the region between the resist film and the lens at the lowermost point of the exposure apparatus is pre-filled with a solvent (immersion medium) that has a larger refractive index than the refractive index of air, and the exposure (immersion exposure) is conducted in this state.

The immersion medium preferably exhibits a refractive index larger than the refractive index of air but smaller than the refractive index of the resist film to be exposed. The refractive index of the immersion medium is not particularly limited as long as it satisfies the above-mentioned requirements.

Examples of this immersion medium which exhibits a refractive index that is larger than the refractive index of air but smaller than the refractive index of the resist film include water, fluorine-based inert liquids, silicon-based solvents and hydrocarbon-based solvents.

Specific examples of the fluorine-based inert liquids include liquids containing a fluorine-based compound such as $C_3HCl_2F_5$, $C_4F_9OCH_3$, $C_4F_9OC_2H_5$ or $C_5H_3F_7$ as the main component, which have a boiling point within a range from 70 to 180° C. and preferably from 80 to 160° C. A fluorine-based inert liquid having a boiling point within the above-mentioned range is advantageous in that the removal of the immersion medium after the exposure can be conducted by a simple method.

As a fluorine-based inert liquid, a perfluoroalkyl compound in which all of the hydrogen atoms of the alkyl group are substituted with fluorine atoms is particularly desirable. Examples of these perfluoroalkyl compounds include perfluoroalkylether compounds and perfluoroalkylamine compounds.

Specifically, one example of a suitable perfluoroalkylether compound is perfluoro(2-butyl-tetrahydrofuran) (boiling point 102° C.), and an example of a suitable perfluoroalkylamine compound is perfluorotributylamine (boiling point 174° C.).

As the immersion medium, water is preferable in terms of cost, safety, environment and versatility.

As an example of the alkali developing solution used in an alkali developing process, a 0.1 to 10% by weight aqueous solution of tetramethylammonium hydroxide (TMAH) can be given.

As the organic solvent contained in the organic developing solution used in a solvent developing process, any of the conventional organic solvents can be used which are capable of dissolving the component (A) (prior to exposure). Specific examples of the organic solvent include polar solvents such as ketone solvents, ester solvents, alcohol solvents, nitrile solvents, amide solvents and ether solvents, and hydrocarbon solvents.

A ketone solvent is an organic solvent containing C—C(=O)—C within the structure thereof. An ester solvent is an organic solvent containing C—C(=O)—O—C within the structure thereof. An alcohol solvent is an organic solvent containing an alcoholic hydroxy group in the structure thereof. An "alcoholic hydroxy group" refers to a hydroxy group bonded to a carbon atom of an aliphatic hydrocarbon group. A nitrile solvent is an organic solvent containing a nitrile group in the structure thereof. An amide solvent is an organic solvent containing an amide group within the structure thereof. An ether solvent is an organic solvent containing C—O—C within the structure thereof.

Some organic solvents have a plurality of the functional groups which characterizes the aforementioned solvents within the structure thereof. In such a case, the organic solvent can be classified as any type of the solvent having the characteristic functional group. For example, diethyleneglycol monomethylether can be classified as either an alcohol solvent or an ether solvent.

A hydrocarbon solvent consists of a hydrocarbon which may be halogenated, and does not have any substituent other than a halogen atom. Examples of the halogen atom include a fluorine atom, a chlorine atom, a bromine atom and an iodine atom, and a fluorine atom is preferable.

As the organic solvent contained in the organic developing solution, among these, a polar solvent is preferable, and ketone solvents, ester solvents and nitrile solvents are preferable.

Examples of ketone solvents include 1-octanone, 2-octanone, 1-nonanone, 2-nonanone, acetone, 4-heptanone, 1-hexanone, 2-hexanone, diisobutyl ketone, cyclohexanone, methylcyclohexanone, phenylacetone, methyl ethyl ketone, methyl isobutyl ketone, acetylacetone, acetonylacetone, ionone, diacetonylalcohol, acetylcarbinol, acetophenone, methyl naphthyl ketone, isophorone, propylenecarbonate, γ-butyrolactone and methyl amyl ketone (2-heptanone). Among these examples, as a ketone solvent, methyl amyl ketone (2-heptanone) is preferable.

Examples of ester solvents include methyl acetate, butyl acetate, ethyl acetate, isopropyl acetate, amyl acetate, isoamyl acetate, ethyl methoxyacetate, ethyl ethoxyacetate, propylene glycol monomethyl ether acetate, ethylene glycol monoethyl ether acetate, ethylene glycol monopropyl ether acetate, ethylene glycol monobutyl ether acetate, ethylene glycol monophenyl ether acetate, diethylene glycol monomethyl ether acetate, diethylene glycol monopropyl ether acetate, diethylene glycol monoethyl ether acetate, diethylene glycol monophenyl ether acetate, diethylene glycol monobutyl ether acetate, diethylene glycol monoethyl ether acetate, 2-methoxybutyl acetate, 3-methoxybutyl acetate, 4-methoxybutyl acetate, 3-methyl-3-methoxybutyl acetate, 3-ethyl-3-methoxybutyl acetate, propylene glycol monomethyl ether acetate, propylene glycol monoethyl acetate, propylene glycol monopropyl ether acetate, 2-ethoxybutyl acetate, 4-ethoxybutyl acetate, 4-propoxybutyl acetate, 2-methoxypentyl acetate, 3-methoxypentyl acetate, 4-methoxypentyl acetate, 2-methyl-3-methoxypentyl acetate, 3-methyl-3-methoxypentyl acetate, 3-methyl-4-methoxypentyl acetate, 4-methyl-4-methoxypentyl acetate, propylene glycol diacetate, methyl formate, ethyl formate, butyl formate, propyl formate, ethyl lactate, butyl lactate, propyl lactate, ethyl carbonate, propyl carbonate, butyl carbonate, methyl pyruvate, ethyl pyruvate, propyl pyruvate, butyl pyruvate, methyl acetoacetate, ethyl acetoacetate, methyl propionate, ethyl propionate, propyl propionate, isopropyl propionate, methyl 2-hydroxypropionate, ethyl 2-hydroxypropionate, methyl-3-methoxypropionate, ethyl-3-methoxypropionate, ethyl-3-ethoxypropionate and propyl-3-methoxypropionate. Among these examples, as an ester solvent, butyl acetate is preferable.

Examples of nitrile solvents include acetonitrile, propionitrile, valeronitrile, and butyronitrile.

If desired, the organic developing solution may have a conventional additive blended. Examples of the additive include surfactants. The surfactant is not particularly limited, and for example, an ionic or non-ionic fluorine and/or silicon surfactant can be used.

As the surfactant, a non-ionic surfactant is preferable, and a non-ionic fluorine surfactant or a non-ionic silicon surfactant is more preferable.

When a surfactant is added, the amount thereof based on the total amount of the organic developing solution is generally 0.001 to 5% by weight, preferably 0.005 to 2% by weight, and more preferably 0.01 to 0.5% by weight.

The developing treatment can be performed by a conventional developing method. Examples thereof include a method in which the substrate is immersed in the developing solution for a predetermined time (a dip method), a method in which the developing solution is cast up on the surface of the substrate by surface tension and maintained for a predetermined period (a puddle method), a method in which the developing solution is sprayed onto the surface of the substrate (spray method), and a method in which the developing solution is continuously ejected from a developing solution ejecting nozzle while scanning at a constant rate to apply the developing solution to the substrate while rotating the substrate at a constant rate (dynamic dispense method).

As the organic solvent contained in the rinse liquid used in the rinse treatment after the developing treatment in the case of a solvent developing process, any of the aforementioned organic solvents contained in the organic developing solution can be used which hardly dissolves the resist pattern. In general, at least one solvent selected from the group consisting of hydrocarbon solvents, ketone solvents, ester solvents, alcohol solvents, amide solvents and ether solvents is used. Among these, at least one solvent selected from the group consisting of hydrocarbon solvents, ketone solvents, ester solvents, alcohol solvents and amide solvents is preferable, more preferably at least one solvent selected from the group consisting of alcohol solvents and ester solvents, and an alcohol solvent is particularly desirable.

The alcohol solvent used for the rinse liquid is preferably a monohydric alcohol of 6 to 8 carbon atoms, and the monohydric alcohol may be linear, branched or cyclic. Specific examples thereof include 1-hexanol, 1-heptanol, 1-octanol, 2-hexanol, 2-heptanol, 2-octanol, 3-hexanol, 3-heptanol, 3-octanol, 4-octanol and benzyl alcohol. Among these, 1-hexanol, 2-heptanol and 2-hexanol are preferable, and 1-hexanol and 2-hexanol are more preferable.

As the organic solvent, one kind of solvent may be used alone, or two or more kinds of solvents may be used in combination. Further, an organic solvent other than the aforementioned examples or water may be mixed together. However, in consideration of the development characteristics, the amount of water within the rinse liquid, based on the total amount of the rinse liquid is preferably 30% by weight or less, more preferably 10% by weight or less, still more preferably 5% by weight or less, and most preferably 3% by weight or less.

If desired, the rinse solution may have a conventional additive blended. Examples of the additive include surfactants. Examples of the additive include surfactants. As the surfactant, the same surfactants as those described above can be mentioned, a non-ionic surfactant is preferable, and a non-ionic fluorine surfactant or a non-ionic silicon surfactant is more preferable.

When a surfactant is added, the amount thereof based on the total amount of the rinse liquid is generally 0.001 to 5% by weight, preferably 0.005 to 2% by weight, and more preferably 0.01 to 0.5% by weight.

The rinse treatment using a rinse liquid (washing treatment) can be conducted by a conventional rinse method. Examples of the rinse method include a method in which the rinse liquid is continuously applied to the substrate while rotating it at a constant rate (rotational coating method), a method in which the substrate is immersed in the rinse liquid for a predetermined time (dip method), and a method in which the rinse liquid is sprayed onto the surface of the substrate (spray method).

In the method of forming a resist pattern according to the present embodiment, by virtue of using the resist composition of the first aspect, it becomes possible to enhance sensitivity in the formation of a resist pattern, and a resist pattern having improved lithography properties (such as reduced roughness) can be formed.

(Compound)

The compound according to a third aspect of the present invention is represented by general formula (b1) shown below.

[Chemical Formula 74.]

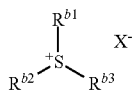

(b1)

In the formula, $R^{b1}$ represents an aryl group which may have a substituent; $R^{b2}$ and $R^{b3}$ each independently represents an aryl group which may have a substituent or an alkyl group which may have a substituent;

$R^{b2}$ and $R^{b3}$ may be mutually bonded to form a ring with the sulfur atom; provided that at least one of the aryl group represented by $R^{b1}$ and the aryl group or the alkyl group represented by $R^{b2}$ or $R^{b3}$ has a substituent containing a halogen atom, and at least one of the aryl group represented by $R^{b1}$ and the aryl group or the alkyl group represented by $R^{b2}$ or $R^{b3}$ has a substituent containing a sulfonyl group; and $X^-$ represents a counteranion.

The compound represented by general formula (b1) above is the same as the component (B1) described above for the resist composition of the present embodiment.

(Acid Generator)

The acid generator according to the fourth aspect of the present invention includes the compound of the third aspect.

The acid generator is useful as an acid-generator component for a chemically amplified resist composition. By virtue of using such acid-generator component in a chemically amplified resist composition, it becomes possible to enhance sensitivity in the formation of a resist pattern, and a resist pattern having improved lithography properties (such as reduced roughness) can be formed. In particular, by virtue of using such acid-generator component, high sensitivity to an EB or EUV exposure source can be obtained. In addition, according to a chemically amplified resist composition containing such acid-generator component, resolution performance is improved.

(Compound (Intermediate))

The compound according to a fifth aspect of the present invention is represented by general formula (bp-1).

The compound according to the fifth aspect is useful as an intermediate in producing a compound according to the third aspect.

[Chemical Formula 75.]

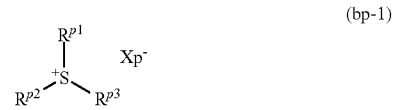

(bp-1)

In the formula, $R^{p1}$ represents an aryl group which may have a substituent; $R^{p2}$ and $R^{p3}$ each independently represents an aryl group which may have a substituent or an alkyl group which may have a substituent;

$R^{p2}$ and $R^{p3}$ may be mutually bonded to form a ring with the sulfur atom; provided that at least one of the aryl group represented by $R^{p1}$ to $R^{p3}$ is the aforementioned aryl group or alkyl group having a substituent containing a halogen atom, and at least one of $R^{p1}$ to $R^{p3}$ is an aryl group or alkyl group having a group represented by the formula: —$SR^{p4}$; $R^{p4}$ represents an alkyl group; and Xp$^-$ represents a counteranion.

In formula (bp-1), the aryl group (which may have a substituent) represented by $R^{p1}$ is the same as defined for the aryl group (which may have a substituent) represented by $R^{b1}$.

In formula (bp-1), the aryl group or alkyl group (which may have a substituent) represented by $R^{p2}$ or $R^{p3}$ is the same as defined for the aryl group or alkyl group (which may have a substituent) represented by $R^{b2}$ or $R^{b3}$ in the aforementioned formula (b1).

In formula (bp-1), at least one of $R^{p1}$ to $R^{p3}$ is the aforementioned aryl group or alkyl group having a substituent containing a halogen atom, and at least one of $R^{p1}$ to $R^{p3}$ is an aryl group or alkyl group having a group represented by the formula: —$SR^{p4}$. $R^{p4}$ represents an alkyl group.

Regarding $R^{p1}$ to $R^{p3}$, the substituent containing a halogen atom is the same as defined for the substituent containing a halogen atom described above in relation to $R^{b1}$ to $R^{b3}$ in the aforementioned formula (b1).

In the group represented by the formula: —$SR^{p4}$, the alkyl group for $R^{p4}$ is preferably a linear or branched alkyl group. Examples of the linear or branched alkyl group include a methyl group, an ethyl group, a propyl group, an isopropyl group, an n-butyl group, an isobutyl group, a tert-butyl group, a pentyl group, an isopentyl group and a neopentyl group, preferably a methyl group or an ethyl group, and more preferably a methyl group.

Further, regarding the group represented by the formula —$SR^{p4}$, in the case where $R^{p2}$ and $R^{p3}$ are mutually bonded to form a ring with the sulfur atom, and the ring is formed together with the group represented by the formula —$SR^{p4}$, the group represented by the formula —$SR^{p4}$ may be present in the ring in the form of a divalent group in which one hydrogen atom has been removed from the alkyl group $R^{p4}$, or a divalent group "—S—" (i.e., —$SR^{p4'}$—($R^{p4'}$ represents an alkylene group or a single bond).

In formula (bp-1), examples of the counteranion represented by $Xp^-$ include a halogen anion (Cl$^-$, Br$^-$, I$^-$), a carboxylic acid anion (such as an acetic acid anion) and $RpSO_3^-$. Rp is an alkyl group having 1 to 5 carbon atoms (a methyl group, an ethyl group, a propyl group, an isopropyl group, an n-butyl group, an isobutyl group, a tert-butyl group, a pentyl group, an isopentyl group or a neopentyl group) or a fluorinated alkyl group having 1 to 5 carbon atoms, and is preferably a trifluoromethyl group.

(Production Method of Compound)

The method of producing a compound according to a sixth aspect of the present invention includes oxidizing a compound represented by general formula (bp-1) shown below (hereafter, referred to as "compound (bp-1)") to obtain a compound represented by general formula (b1-1) shown below (hereafter, referred to as "compound (b1-1)").

[Chemical Formula 76.]

(bp-1)

In the formula, $R^{p1}$ represents an aryl group which may have a substituent; $R^{p2}$ and $R^{p3}$ each independently represents an aryl group which may have a substituent or an alkyl group which may have a substituent;

$R^{p2}$ and $R^{p3}$ may be mutually bonded to form a ring with the sulfur atom; provided that at least one of the aryl group represented by $R^{p1}$ and the aryl group or the alkyl group represented by $R^{p2}$ or $R^{p3}$ has a substituent containing a halogen atom, and at least one of the aryl group represented by $R^{p1}$ and the aryl group or the alkyl group represented by $R^{p2}$ or $R^{p3}$ has a group represented by the formula: —$SR^{p4}$; $R^{p4}$ represents an alkyl group; and $Xp^-$ represents a counteranion.

[Chemical Formula 77.]

(b1-1)

In the formula, $R^{b11}$ represents an aryl group which may have a substituent; $R^{b12}$ and $R^{b13}$ each independently represents an aryl group which may have a substituent or an alkyl group which may have a substituent; $R^{b12}$ and $R^{b13}$ may be mutually bonded to form a ring with the sulfur atom; provided that at least one of the aryl group represented by $R^{b11}$ and the aryl group or the alkyl group represented by $R^{b12}$ or $R^{b13}$ has a substituent containing a halogen atom, and at least one of the aryl group represented by $R^{b11}$ and the aryl group or the alkyl group represented by $R^{b12}$ or $R^{b13}$ has a group represented by the formula: —$SO_2$—$R^{p4}$; $R^{p4}$ represents an alkyl group; and $Xp^-$ represents a counteranion.

The compound (bp-1) is the same as defined for the compound according to the fifth aspect described above.

In formula (b1-1), the aryl group (which may have a substituent) represented by $R^{b11}$ is the same as defined for the aryl group (which may have a substituent) represented by $R^{b1}$ in the aforementioned formula (b1).

In formula (b1-1), the aryl group or alkyl group (which may have a substituent) represented by $R^{b12}$ or $R^{b13}$ is the same as defined for the aryl group or alkyl group (which may have a substituent) represented by $R^{b2}$ or $R^{b3}$ in the aforementioned formula (b1).

In formula (b1-1), at least one of the aryl group represented by $R^{b1}$ and the aryl group or the alkyl group represented by $R^{b12}$ or $R^{b13}$ has a substituent containing a halogen atom, and at least one of the aryl group represented by $R^{b11}$ and the aryl group or the alkyl group represented by $R^{b12}$ or $R^{b13}$ has a group represented by the formula: —$SO_2$—$R^{p4}$.

Regarding $R^{b11}$ to $R^{b13}$, the substituent containing a halogen atom is the same as defined for the substituent containing a halogen atom described above in relation to $R^{b1}$ to $R^{b3}$ in the aforementioned formula (b1).

In the group represented by the formula —$SO_2$—$R^{p4}$, the alkyl group represented by $R^{p4}$ is the same as defined for the alkyl group represented by $R^{p4}$ in the "group represented by the formula: —$SR^{p4}$" described above in relation to $R^{p1}$ to $R^{p3}$ in the aforementioned formula (bp-1).

In formula (b1-1), the counteranion represented by $Xp^-$ is the same as defined for the counteranion represented by $Xp^-$ in the aforementioned formula (bp-1).

The method of oxidizing the compound (bp-1) is not particularly limited, and examples thereof include an oxidation reaction (e.g., oxone oxidation) in which the compound (bp-1) is reacted with potassium peroxymonosulfate (2$KHSO_5$. $KHSO_4$. $K_2SO_4$).

The solvent used in the oxidation reaction is not particularly limited, and examples thereof include at least one member selected from the group consisting of water and an alcohol solvent such as methanol, ethanol or isopropanol.

The reaction temperature in the oxidation reaction is not particularly limited, and is preferably 0 to 50° C., more preferably 5 to 40° C.

The reaction time in the oxidation reaction is not particularly limited, and is preferably 1 to 72 hours, more preferably 2 to 60 hours.

As the compound (bp-1), commercially available compound may be used, or the compound may be synthesized by a conventional method.

The compound (b1-1) may be subjected to a salt exchange reaction with an ammonium salt having a desired anion, so as to obtain a compound having the desired anion (acid generator (B1)).

After the salt exchange reaction, the compound in the reaction liquid may be separated and purified. The separation and purification can be conducted by a conventional method. For example, any of concentration, solvent extraction, distillation, crystallization, re-crystallization and chromatography may be used.

The structure of the compound obtained in the manner described above can be identified by a general organic analysis method such as $^1$H-nuclear magnetic resonance (NMR) spectrometry, $^{13}$C-NMR spectrometry, $^{19}$F-NMR spectrometry, infrared absorption (IR) spectrometry, mass spectrometry (MS), elementary analysis and X-ray diffraction analysis.

EXAMPLES

As follows is a description of examples of the present invention, although the scope of the present invention is by no way limited by these examples.

In the following examples, a compound represented by a chemical formula (1) is denoted as "compound (1)", and the same applies for compounds represented by other chemical formulae.

<Production of Compound>

Production Example 1

Diphenylsulfoxide (20 g, 99 mmol) and trimethylsilyltrifluoromethane sulfonate (44 g, 198 mmol) were dissolved in THF (64 g), and a THF solution of 3-trifluoromethyl-4-fluorophenylmagnesiumbromide was dropwise added thereto while maintaining the reaction system at a temperature not exceeding −5° C. The THF solution of 3-trifluoromethyl-4-fluorophenylmagnesiumbromide was prepared from 5-bromo-2-fluorobenzotrifluoride (24 g, 99 mmol), magnesium (2.4 g, 99 mmol) and THF (93 g) by a conventional method. After the dropwise addition, the reaction was continued for 1 hour to complete the reaction. The reaction liquid was added to ultrapure water (370 g) over 1 hour, and dichloromethane (490 g) was added thereto, followed by stirring for 30 minutes and removing the aqueous phase. The organic phase was washed with ultrapure water (370 g) 3 times, and the organic phase was dropwise added to methyl tert-butyl ether (MTBE) (4,900 g), followed by subjecting the precipitated solid to filtration. The residue was dried under reduced pressure, so as to obtain intermediate B1 (20.8 g, yield=43.0%).

[Chemical Formula 78.]

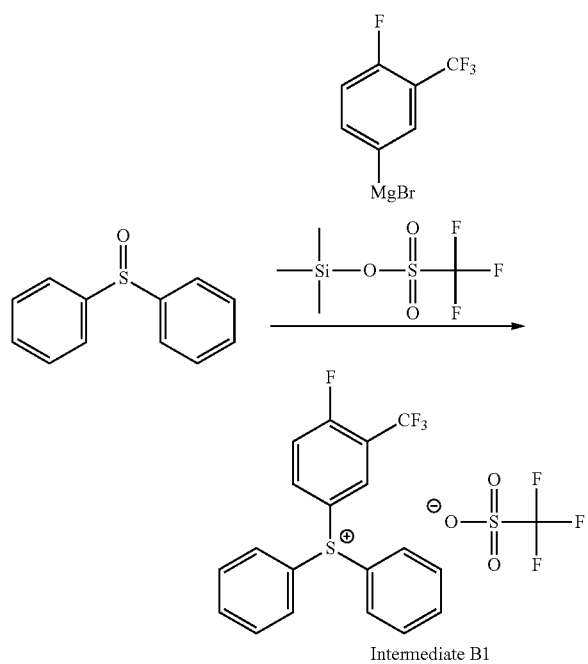

Intermediate B1 (20 g, 41 mmol) was dissolved in acetonitrile (100 g), and a 15 wt % aqueous solution of methyl mercaptan sodium (21 g, 45 mmol) was dropwise added while maintaining the reaction system at a temperature not exceeding −10° C. After the dropwise addition, the reaction was continued at −10° C. for 1 hour to complete the reaction. Then, the aqueous phase was removed, and the organic phase was concentrated using a rotary evaporator. The concentrate was dissolved in dichloromethane (190 g).

The resultant was washed with 1% hydrochloric acid (65 g), followed by washing with ultrapure water (65 g) 3 times. Then, the organic phase was dropwise added to MTBE (1,900 g), and the precipitated solid was subjected to filtration. The residue was dried under reduced pressure, so as to obtain intermediate B2 (819.6 g, yield=90.9%).

[Chemical Formula 79.]

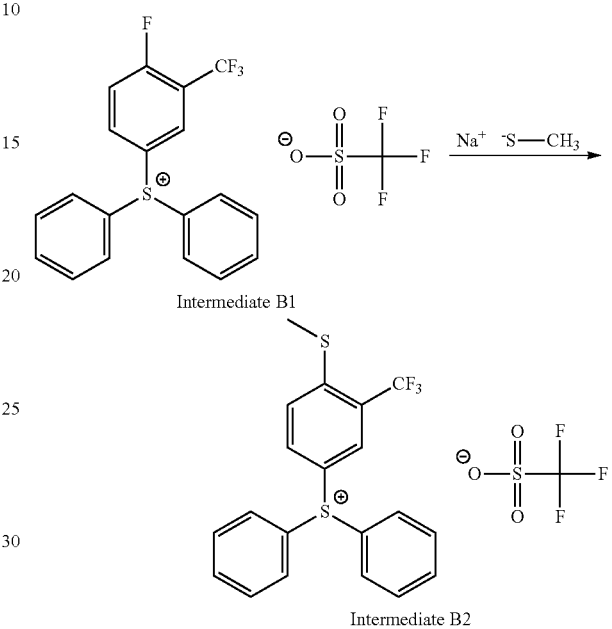

Intermediate B2 (19 g, 36 mmol) was dissolved in a mixed solution of ultrapure water (14 g) and methanol (43 g), and Oxone (registered trademark) (33 g, 54 mmol, molecular formula: $2KHSO_5 \cdot KHSO_4 K_2SO_4$, molecular weight: 614.76) was added thereto, followed by stirring at room temperature for 48 hours. The reaction liquid was subjected to filtration, and ultrapure water (29 g) and dichloromethane (180 g) were added thereto, followed by stirring for 30 minutes and removing the aqueous phase. The resultant was washed with a saturated aqueous solution of sodium hydrogen sulfite (60 g), followed by washing with ultrapure water (60 g) 3 times. The organic phase was dropwise added to MTBE (1,800 g), and the precipitated solid was subjected to filtration. The residue was dried under reduced pressure, so as to obtain precursor B1 (14.1 g, yield=70.0%).

[Chemical Formula 80.]

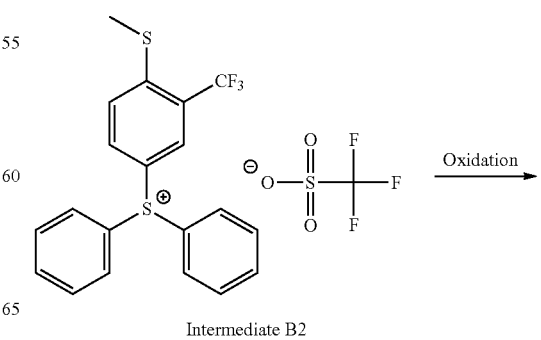

151

-continued

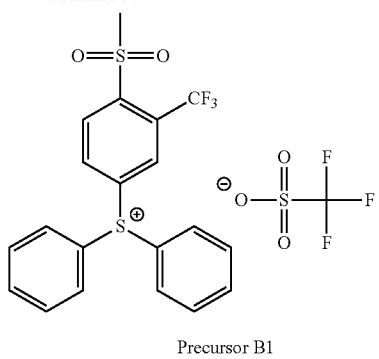

Precursor B1

Precursor B1 (12 g, 21 mmol) and compound 1 (12.7 g, 24 mmol) were dissolved in dichloromethane (100 g), and ultrapure water (30 g) was added thereto, followed by conducting a reaction at room temperature for 30 minutes. After the reaction, the aqueous phase was removed, and the organic phase was washed with ultrapure water (30 g) 4 times. The organic phase was concentrated and solidified using a rotary evaporator, so as to obtain acid generator (B1-1) (15.6 g, yield=91.2%).

[Chemical Formula 81.]

152

Production Example 2

Thianthrene-5-oxide (17 g, 73 mmol) and trimethylsilyl-trifluoromethanesulfonate (32.5 g, 146 mmol) were dissolved in THF (50 g), and a THF solution of 3-trifluoromethylphenylmagnesiumbromide was dropwise added thereto while maintaining the reaction system at a temperature not exceeding −5° C. The THF solution of trifluoromethylphenylmagnesiumbromide was prepared from 3-bromo-benzotrifluoride (16.5 g, 73 mmol), magnesium (1.8 g, 73 mmol) and THF (64 g) by a conventional method. After the dropwise addition, the reaction was continued for 1 hour to complete the reaction. The reaction liquid was added to ultrapure water (270 g) over 1 hour. Then, dichloromethane (360 g) was added, followed by stirring for 30 minutes and removing the aqueous phase. The organic phase was washed with ultrapure water (270 g) 3 times, and the organic phase was dropwise added to MTBE (3,600 g), followed by subjecting the precipitated solid to filtration. The residue was dried under reduced pressure, so as to obtain intermediate B3 (17.7 g, yield=47.5%).

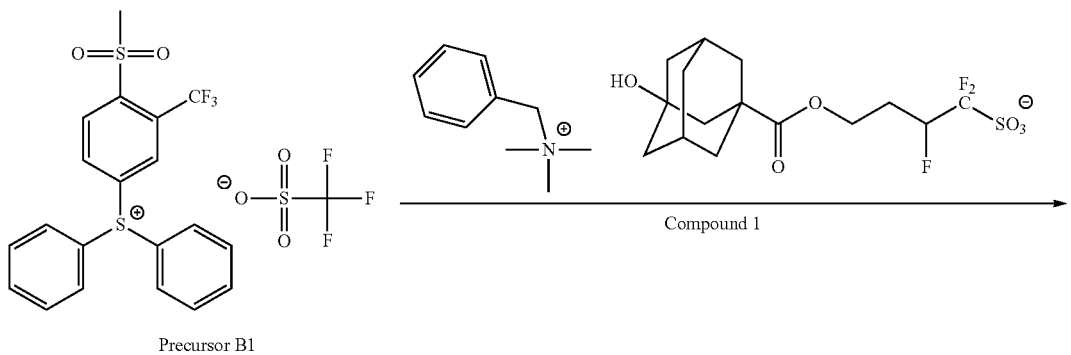

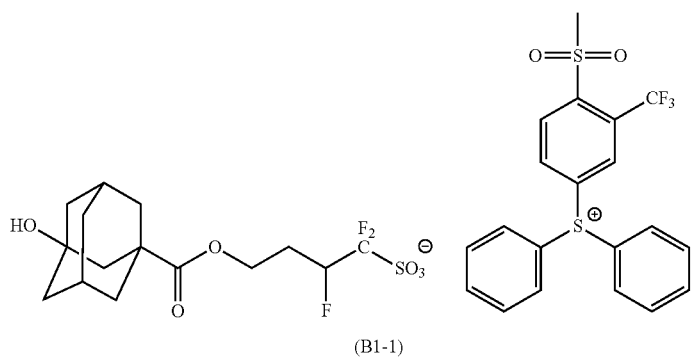

(B1-1)

[Chemical Formula 82.]

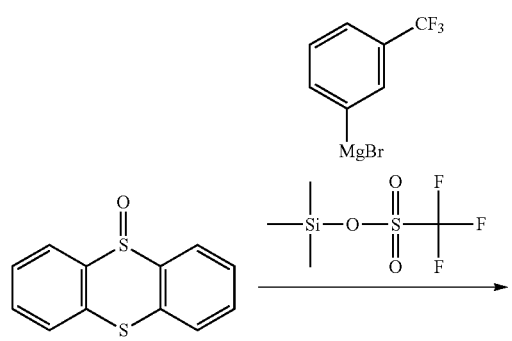

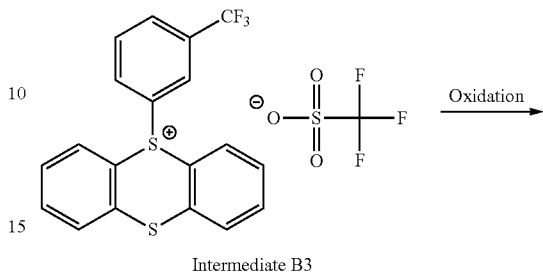

Intermediate B3 solid was subjected to filtration. The residue was dried under reduced pressure, so as to obtain precursor B2 (12.5 g, yield=73.3%).

[Chemical Formula 83.]

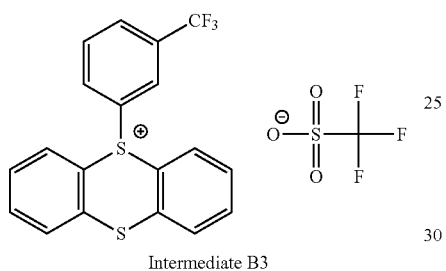

Intermediate B3

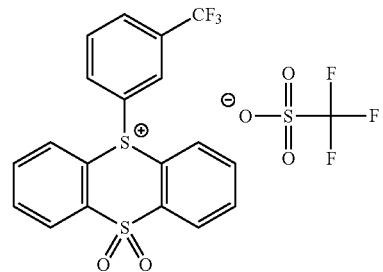

Precursor B2

Intermediate B3 (16 g, 31 mmol) was dissolved in a mixed solution of ultrapure water (12 g) and methanol (36 g), and oxone (29 g, 47 mmol) was added thereto, followed by stirring at room temperature for 48 hours. The reaction liquid was subjected to filtration, and ultrapure water (24 g) and dichloromethane (150 g) were added thereto, followed by stirring for 30 minutes and removing the aqueous phase. The resultant was washed with a saturated aqueous solution of sodium hydrogen sulfite (50 g), followed by washing with ultrapure water (50 g) 3 times. The organic phase was dropwise added to MTBE (1,500 g), and the precipitated Precursor B2 (12 g, 22 mmol) and compound 1 (13 g, 24 mmol) were dissolved in dichloromethane (100 g), and ultrapure water (30 g) was added thereto, followed by conducting a reaction at room temperature for 30 minutes.

After the reaction, the aqueous phase was removed, and the organic phase was washed with ultrapure water (30 g) 4 times. The organic phase was concentrated and solidified using a rotary evaporator, so as to obtain acid generator (B1-2) (15.9 g, yield=92.4%).

[Chemical Formula 84.]

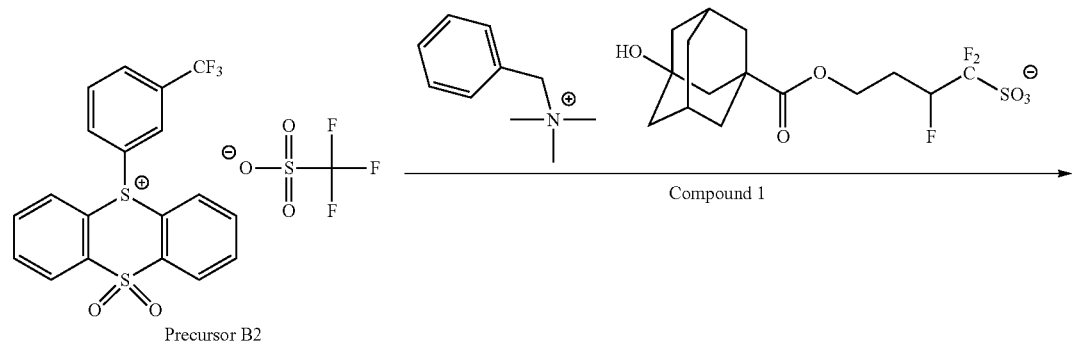

Precursor B2

Compound 1

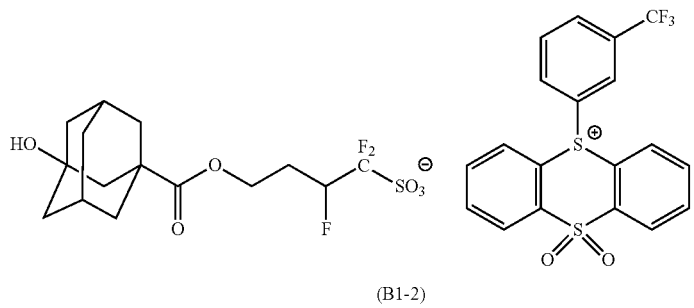

(B1-2)

Production Example 3

Benzothiophene-1-oxide (18 g, 120 mmol) and trimethylsilyltrifloromethanesulfonate (53.3 g, 240 mmol) were dissolved in THF (71 g), and a THF solution of 3-trifluoromethyl-4-fluorophenylmagnesiumbromide was dropwise added thereto while maintaining the reaction system at a temperature not exceeding −5° C. The THF solution of 3-trifluoromethyl-4-fluorophenylmagnesiumbromide was prepared from 5-bromo-2-fluorobenzotrifluoride (29.1 g, 120 mmol), magnesium (1.8 g, 120 mmol) and THF (112 g) by a conventional method. After the dropwise addition, the reaction was continued for 1 hour to complete the reaction. The reaction liquid was added to ultrapure water (430 g) over 1 hour. Then, dichloromethane (570 g) was added, followed by stirring for 30 minutes and removing the aqueous phase. The organic phase was washed with ultrapure water (430 g) 3 times, and the organic phase was dropwise added to MTBE (5,700 g), followed by subjecting the precipitated solid to filtration. The residue was dried under reduced pressure, so as to obtain intermediate B4 (21.9 g, yield=41.0%).

[Chemical Formula 85.]

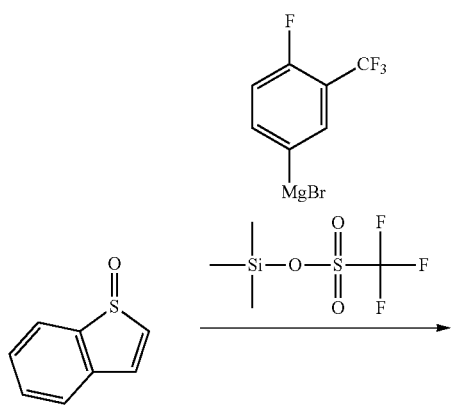

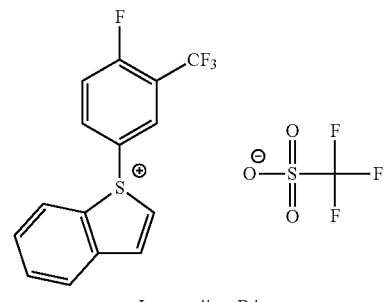

Intermediate B4

Intermediate B4 (20 g, 45 mmol) was dissolved in acetonitrile (100 g), and a 15 wt % aqueous solution of methyl mercaptan sodium (23.0 g, 49 mmol) was dropwise added while maintaining the reaction system at a temperature not exceeding −10° C. After the dropwise addition, the reaction was continued at −10° C. for 1 hour to complete the reaction. Then, the aqueous phase was removed, and the organic phase was concentrated using a rotary evaporator. The concentrate was dissolved in dichloromethane. The resultant was washed with 1% hydrochloric acid (60 g), followed by washing with ultrapure water (60 g) 3 times. Then, the organic phase was dropwise added to MTBE (1,900 g), and the precipitated solid was subjected to filtration. The residue was dried under reduced pressure, so as to obtain intermediate B5 (19.0 g, yield=89.5%).

[Chemical Formula 86.]

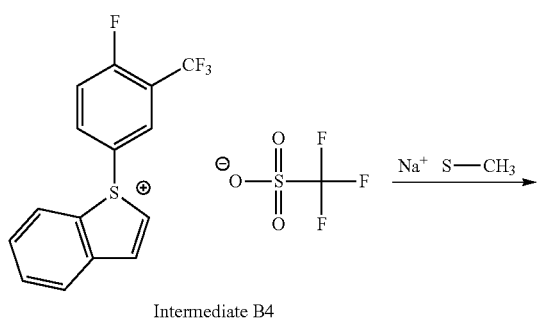

Intermediate B4

[Chemical Formula 87.]

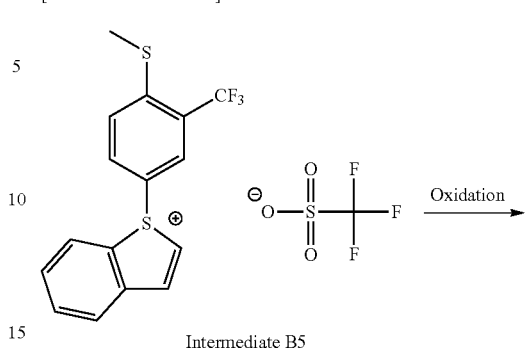

Intermediate B5

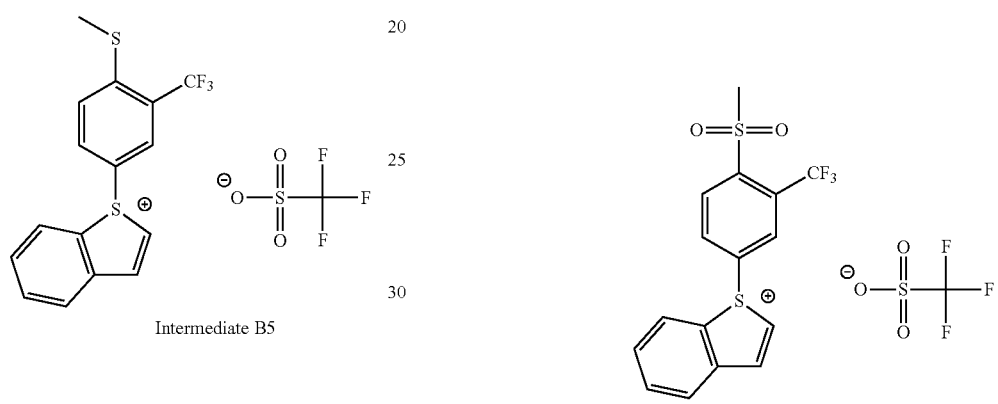

Intermediate B5

Precursor B3

Intermediate B5 (19 g, 40 mmol) was dissolved in a mixed solution of ultrapure water (14 g) and methanol (43 g), and oxone (37 g, 60 mmol) was added thereto, followed by stirring at room temperature for 48 hours. The reaction liquid was subjected to filtration, and ultrapure water (30 g) and dichloromethane (180 g) were added thereto, followed by stirring for 30 minutes and removing the aqueous phase. The resultant was washed with a saturated aqueous solution of sodium hydrogen sulfite (70 g), followed by washing with ultrapure water (60 g) 3 times. The organic phase was dropwise added to MTBE (1,800 g), and the precipitated solid was subjected to filtration. The residue was dried under reduced pressure, so as to obtain precursor B3 (14.6 g, yield=72.1%).

Precursor B3 (12 g, 24 mmol) and compound 2 (12.8 g, 26 mmol) were dissolved in dichloromethane (100 g), and ultrapure water (30 g) was added thereto, followed by conducting a reaction at room temperature for 30 minutes. After the reaction, the aqueous phase was removed, and the organic phase was washed with ultrapure water (30 g) 4 times. The organic phase was concentrated and solidified using a rotary evaporator, so as to obtain acid generator (B1-3) (14.9 g, yield=90.5%).

[Chemical Formula 88.]

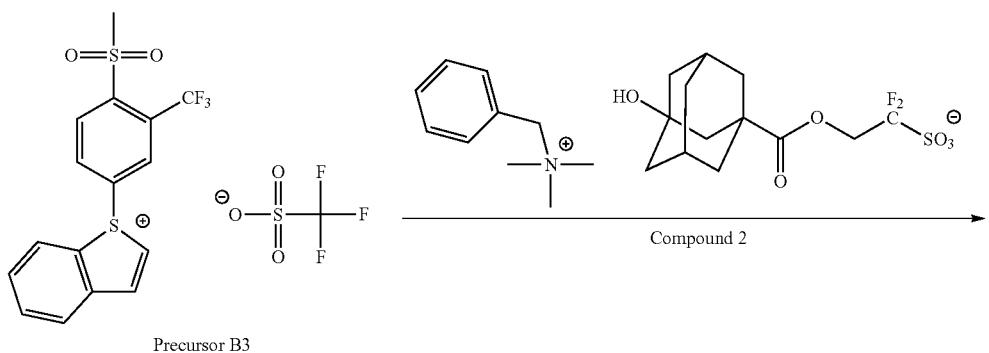

Precursor B3

Compound 2

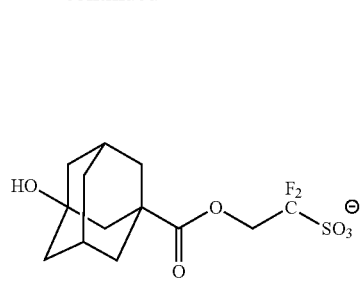
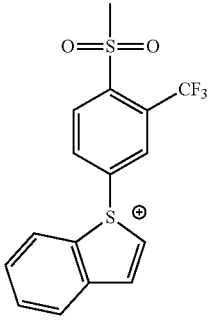

(B1-3)

Production Example 4

3-bromothioanisole (30 g, 148 mmol), magnesium (3.6 g, 148 mmol) and THF (150 g) were used to prepare a THF solution of 3-methylthiophenylmagnesiumbromide by a conventional method. The THF solution of 3-methylthiophenylmagnesiumbromide was dropwise added to a solution obtained by diluting thionyl chloride (8.8 g, 74 mmol) in THF (20 g), while maintaining the reaction system at a temperature not exceeding −5° C. After the dropwise addition, the reaction was continued at room temperature for 1 hour to complete the reaction.

The reaction liquid was added to ultrapure water (150 g) over 1 hour. Then, dichloromethane (210 g) was added, followed by stirring for 30 minutes and removing the aqueous phase. The organic phase was washed with ultrapure water (150 g) 3 times, and the organic phase was concentrated using a rotary evaporator. The concentrate was recrystallized in cyclohexane, so as to obtain intermediate B6 (10.9 g, yield=50.0%).

[Chemical Formula 89.]

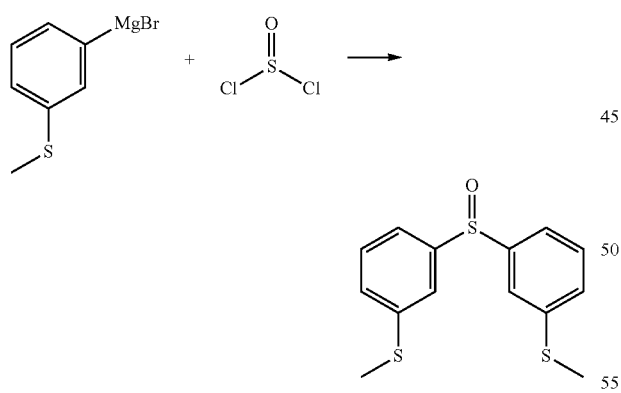

Intermediate 6 (10 g, 34 mmol) and trimethylsilyltrifluoromethanesulfonate (15.1 g, 68 mmol) were dissolved in THF (25 g), and a THF solution of 3,5-bistrifluoromethylbromobenzenemagnesiumbromide was dropwise added thereto while maintaining the reaction system at a temperature not exceeding −5° C. The THF solution of 3,5-bistrifluoromethylbromobenzenemagnesiumbromide was prepared from 3,5-bistrifluoromethylbromobenzene (10.0 g, 34 mmol), magnesium (0.8 g, 34 mmol) and THF (38 g). After the dropwise addition, the reaction was continued for 1 hour to complete the reaction. The reaction liquid was added to ultrapure water (150 g) over 1 hour. Then, dichloromethane (200 g) was added, followed by stirring for 30 minutes and removing the aqueous phase. The organic phase was washed with ultrapure water (150 g) 3 times, and the organic phase was dropwise added to MTBE (2,000 g), followed by subjecting the precipitated solid to filtration. The residue was dried under reduced pressure, so as to obtain intermediate B7 (14.2 g, yield=65.3%).

[Chemical Formula 90.]

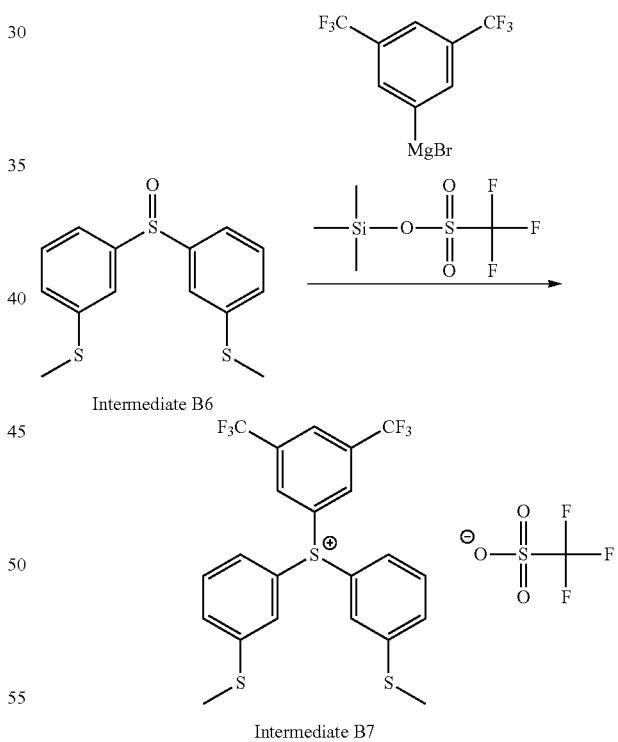

Intermediate B7

Intermediate B7 (13 g, 20 mmol) was dissolved in a mixed solution of ultrapure water (20 g) and methanol (60 g), and oxone (31 g, 51 mmol) was added thereto, followed by stirring at room temperature for 48 hours. The reaction liquid was subjected to filtration, and ultrapure water (40 g) and dichloromethane (130 g) were added thereto, followed by stirring for 30 minutes and removing the aqueous phase. The resultant was washed with a saturated aqueous solution of sodium hydrogen sulfite (60 g), followed by washing with ultrapure water (40 g) 3 times. The organic phase was dropwise added to MTBE (1,300 g), and the precipitated solid was subjected to filtration. The residue was dried under reduced pressure, so as to obtain precursor B4 (9.2 g, yield=64.1%).

[Chemical Formula 91.]

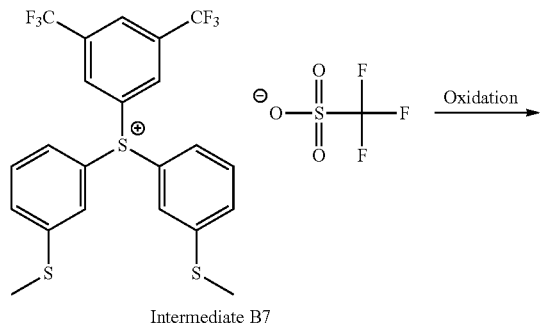

Intermediate B7

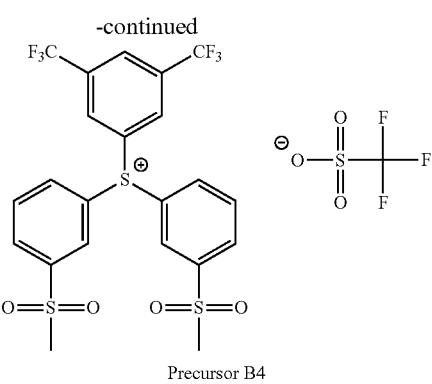

Precursor B4

Intermediate B4 (9.0 g, 13 mmol) and compound 3 (5.2 g, 14 mmol) were dissolved in dichloromethane (70 g), and ultrapure water (20 g) was added thereto, followed by conducting a reaction at room temperature for 30 minutes. After the reaction, the aqueous phase was removed, and the organic phase was washed with ultrapure water (20 g) 4 times. The organic phase was concentrated and solidified using a rotary evaporator, so as to obtain acid generator (B1-4) (10.8 g, yield=93.4%).

[Chemical Formula 92.]

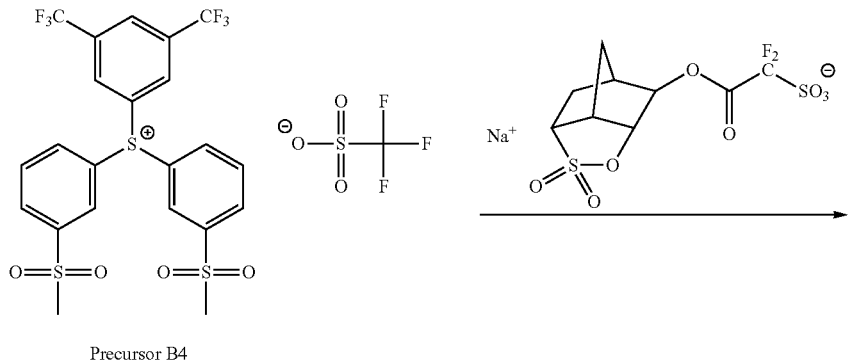

Precursor B4

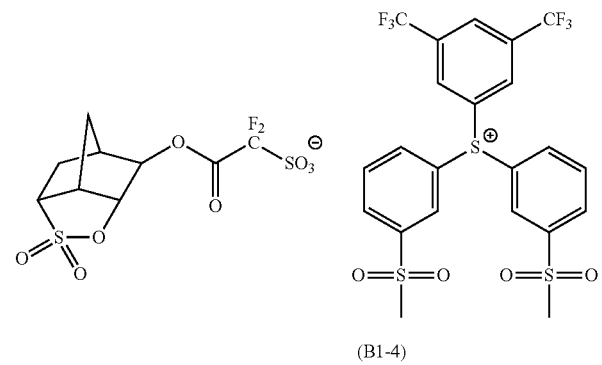

(B1-4)

Production Example 5

1-Bromo-3,4,5-trifluorobenzene (30 g, 142 mmol), magnesium (3.5 g, 142 mmol) and THF (130 g) were used to prepare a THF solution of 3,4,5-trifluorophenylmagnesiumbromide. The THF solution of 3,4,5-trifluorophenylmagnesiumbromide was dropwise added to a solution obtained by diluting thionyl chloride (8.5 g, 71 mmol) in THF (17 g), while maintaining the reaction system at a temperature not exceeding −5° C. After the dropwise addition, the reaction was continued for 1 hour to complete the reaction.

The reaction liquid was added to ultrapure water (110 g) over 1 hour. Then, dichloromethane (440 g) was added, followed by stirring for 30 minutes and removing the aqueous phase. The organic phase was washed with ultrapure water (110 g) 3 times, and the organic phase was concentrated using a rotary evaporator. The concentrate was recrystallized in cyclohexane, so as to obtain intermediate B8 (13.2 g, yield=60.0%).

[Chemical Formula 93.]

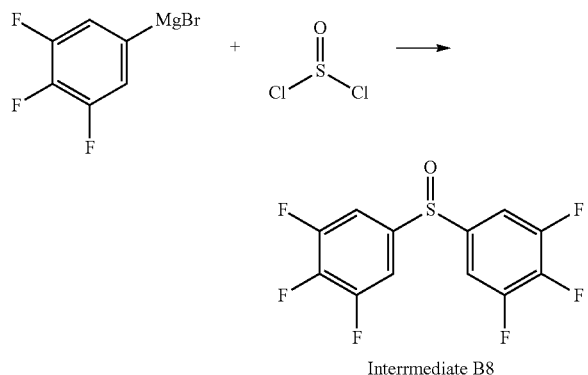

Intermediate B8 (12 g, 39 mmol) was dissolved in benzene (60 g), and trimethylsilyltrifluoromethanesulfonate (21.5 g, 97 mmol) was dropwise added thereto at room temperature.

After the dropwise addition, the reaction was continued at room temperature for 2 hours to complete the reaction. The liquid was separated into oil and benzene phase. After removing the benzene phase, the oil was dissolved in dichloromethane (180 g), followed by washing with ultrapure water (60 g) 6 times. The organic phase was concentrated and solidified using a rotary evaporator, so as to obtain intermediate B9 (17.6 g, yield=87.2%).

[Chemical Formula 94.]

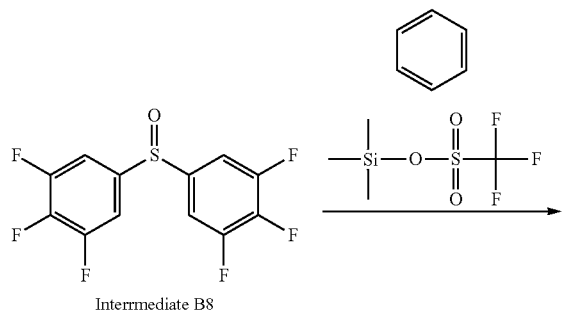

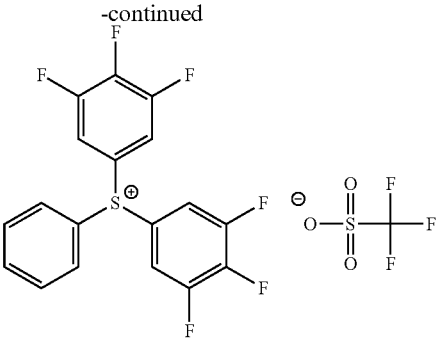

Intermediate B9 (16 g, 31 mmol) was dissolved in acetonitrile (80 g), and a 15 wt % aqueous solution of methyl mercaptan sodium (31.6 g, 68 mmol) was dropwise added while maintaining the reaction system at a temperature not exceeding −10° C. After the dropwise addition, the reaction was continued at −10° C. for 1 hour to complete the reaction. Then, the aqueous phase was removed, and the organic phase was concentrated using a rotary evaporator. The obtained concentrate was dissolved in dichloromethane (160 g). The resultant was washed with 1% hydrochloric acid (50 g), followed by washing with ultrapure water (50 g) 3 times. The organic phase was dropwise added to MTBE (1,600 g), and the precipitated solid was subjected to filtration. The residue was dried under reduced pressure, so as to obtain intermediate B10 (16.5 g, yield=92.9%).

[Chemical Formula 95.]

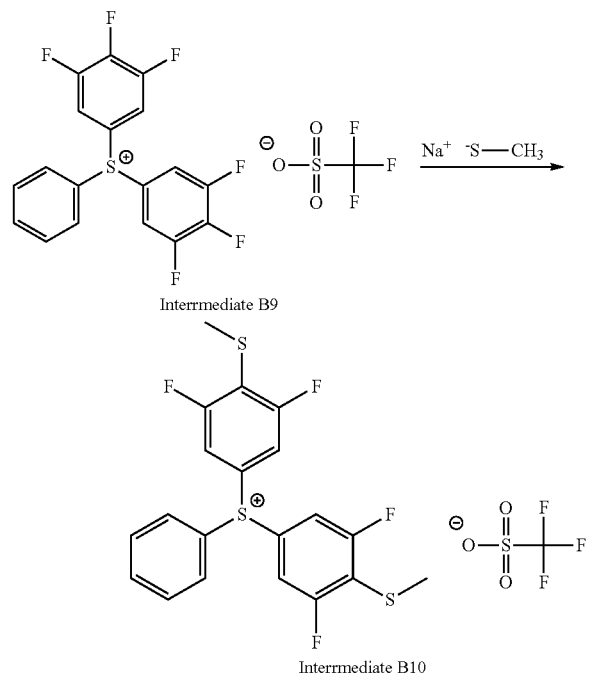

Intermediate B10 (15 g, 26 mmol) was dissolved in a mixed solution of ultrapure water (23 g) and methanol (68 g), and oxone (40 g, 65 mmol) was added thereto, followed by stirring at room temperature for 48 hours. The reaction liquid was subjected to filtration, and ultrapure water (45 g) and dichloromethane (150 g) were added thereto, followed by stirring for 30 minutes and removing the aqueous phase. The resultant was washed with a saturated aqueous solution of sodium hydrogen sulfite (75 g), followed by washing with ultrapure water (50 g) 3 times. The organic phase was dropwise added to MTBE (1,500 g), and the precipitated solid was subjected to filtration. The residue was dried under reduced pressure, so as to obtain precursor B5 (9.1 g, yield=54.4%).

[Chemical Formula 96.]

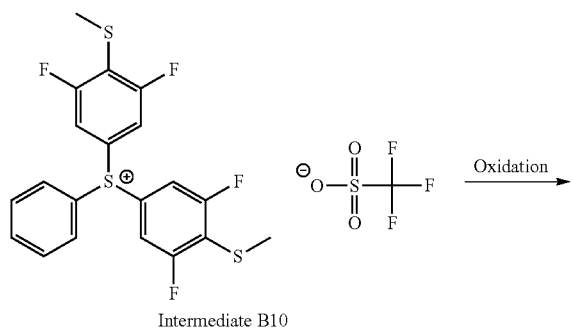

Intermediate B10

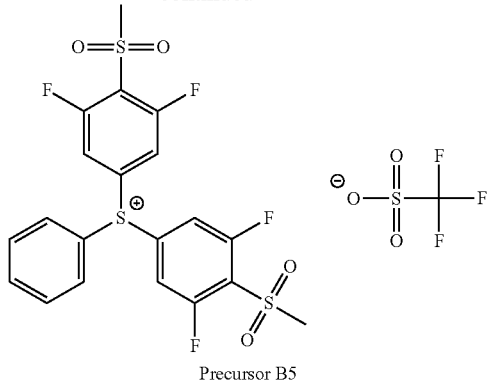

Precursor B5

Intermediate B5 (8.0 g, 12 mmol) and compound 4 (5.8 g, 14 mmol) were dissolved in dichloromethane (60 g), and ultrapure water (20 g) was added thereto, followed by conducting a reaction at room temperature for 30 minutes. After the reaction, the aqueous phase was removed, and the organic phase was washed with ultrapure water (20 g) 4 times. The organic phase was concentrated and solidified using a rotary evaporator, so as to obtain acid generator (B1-5) (9.6 g, yield=94.1%).

[Chemical Formula 97.]

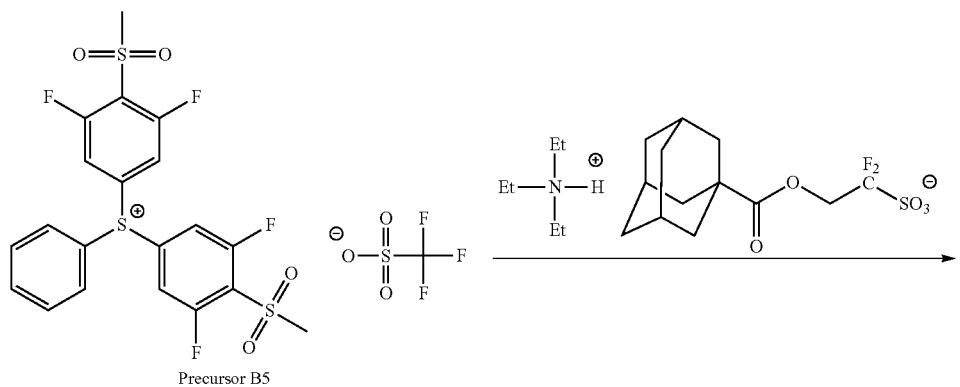

(B1-5)

Each of the obtained compounds was analyzed by NMR, and the structure thereof was identified by the following analysis results.

Compound (B1-1)

$^1$H-NMR (DMSO, 400 MHz): δ (ppm)=8.41 (s, Ph, 1H), 8.12 (d, Ph, 1H), 7.74-8.00 (m, Ph, 11H), 4.86-5.01 (m, CF2CH2, 1H), 4.55 (s, HO, 1H), 4.04-4.26 (m, CH2, 2H), 3.52 (s, CH3, 3H), 2.27-2.48 (m, CFCH, 1H), 2.10-2.18 (m, Adamantyl, 2H), 1.89-2.04 (m, CFCH, 1H1), 1.46-1.73 (m, Adamantyl, 12H)

$^{19}$F-NMR (DMSO, 376 MHz): δ(ppm)=−61.8 ppm, −112.5, −121.2, −203.2

Compound (B1-2)

$^1$H-NMR (DMSO, 400 MHz): δ(ppm)=8.75 (s, ArH, 1H), 8.49 (t, ArH, 2H), 8.32 (d, ArH, 1H), 8.00-8.22 (m, ArH, 5H), 7.88 (d, ArH, 2H), 7.50 (d, ArH, 1H), 4.86-5.01 (m, CF2CH2, 1H), 4.55 (s, HO, 1H), 4.04-4.26 (m, CH2, 2H), 2.27-2.48 (m, CFCH, 1H), 2.10-2.18 (m, Adamantyl, 2H), 1.89-2.04 (m, CFCH, 1H), 1.46-1.73 (m, Adamantyl, 12H)

$^{19}$F-NMR (DMSO, 376 MHz): δ(ppm)=−62.3 ppm, −112.5, −121.2, −203.2

Compound (B1-3)

$^1$H-NMR (DMSO, 400 MHz): δ(ppm)=8.38 (s, 1H, ArH), 8.27 (d, 2H, ArH), 8.11-8.15 (m, 2H, ArH), 7.67-7.84 (m, 4H, ArH), 4.55 (m, CF2CH2, HO, 4H), 3.56 (s, CH3, 3H), 1.46-2.18 (m, Adamantyl, 14H)

$^{19}$F-NMR (DMSO, 376 MHz): δ(ppm)=−62.1 ppm, −114.5

Compound (B1-4) $^1$H-NMR (DMSO, 400 MHz): δ (ppm)=8.60-8.80 (m, ArH, 5H), 8.41 (d, ArH, 2H), 8.28 (d, ArH, 2H), 8.06 (t, ArH, 2H), 4.78 (m, CH, 1H), 4.66 (t, CH, 1H), 3.88 (t, CH, 1H), 3.31-3.36 (m, CH, 1H), 2.47-2.49 (m, CH, 1H), 1.73-2.21 (m, CH2, 4H) $^{19}$F-NMR (DMSO, 376 MHz): δ (ppm)=−61.2, −107.7

Compound (B1-5)

$^1$H-NMR (DMSO, 400 MHz): δ (ppm)=7.98-8.07 (m, ArH, 6H), 7.94 (t, ArH, 1H), 7.83 (t, ArH, 2H), 4.55 (t, CF2CH2, 2H), 3.53 (s, CH3, 6H), 1.64-1.96 (m, Adamantyl, 15H)

$^{19}$F-NMR (DMSO, 376 MHz): δ(ppm)=−102.3, −111.2

<Production of Resist Composition>

Examples 1 to 10, Comparative Examples 1 to 10

The components shown in Tables 1 and 2 were mixed together and dissolved to obtain each resist composition.

TABLE 1

| | Component (A) | Component (B) | Component (D) | Component (S) |
|---|---|---|---|---|
| Comparative Example 1 | (A)-1 [100] | (B2)-1 [20.9] | (D)-1 [3.8] | (S)-1 [6400] |
| Comparative Example 2 | (A)-1 [100] | (B2)-2 [20.7] | (D)-1 [3.8] | (S)-1 [6400] |
| Example 1 | (A)-1 [100] | (B1)-1 [22.6] | (D)-1 [3.8] | (S)-1 [6400] |
| Example 2 | (A)-1 [100] | (B1)-2 [22.2] | (D)-1 [3.8] | (S)-1 [6400] |
| Comparative Example 3 | (A)-1 [100] | (B2)-3 [18.1] | (D)-1 [3.8] | (S)-1 [6400] |
| Example 3 | (A)-1 [100] | (B1)-3 [19.9] | (D)-1 [3.8] | (S)-1 [6400] |
| Comparative Example 4 | (A)-1 [100] | (B2)-4 [21.3] | (D)-1 [3.8] | (S)-1 [6400] |
| Example 4 | (A)-1 [100] | (B1)-4 [25.7] | (D)-1 [3.8] | (S)-1 [6400] |

TABLE 1-continued

| | Component (A) | Component (B) | Component (D) | Component (S) |
|---|---|---|---|---|
| Comparative Example 5 | (A)-1 [100] | (B2)-5 [19.8] | (D)-1 [3.8] | (S)-1 [6400] |
| Example 5 | (A)-1 [100] | (B1)-5 [23.2] | (D)-1 [3.8] | (S)-1 [6400] |

TABLE 2

| | Component (A) | Component (B) | Component (D) | Component (S) |
|---|---|---|---|---|
| Comparative Example 6 | (A)-2 [100] | (B2)-1 [20.9] | (D)-1 [3.8] | (S)-1 [6400] |
| Comparative Example 7 | (A)-2 [100] | (B2)-2 [20.7] | (D)-1 [3.8] | (S)-1 [6400] |
| Example 6 | (A)-2 [100] | (B1)-1 [22.6] | (D)-1 [3.8] | (S)-1 [6400] |
| Example 7 | (A)-2 [100] | (B1)-2 [22.2] | (D)-1 [3.8] | (S)-1 [6400] |
| Comparative Example 8 | (A)-2 [100] | (B2)-3 [18.1] | (D)-1 [3.8] | (S)-1 [6400] |
| Example 8 | (A)-2 [100] | (B1)-3 [19.9] | (D)-1 [3.8] | (S)-1 [6400] |
| Comparative Example 9 | (A)-2 [100] | (B2)-4 [21.3] | (D)-1 [3.8] | (S)-1 [6400] |
| Example 9 | (A)-2 [100] | (B1)-4 [25.7] | (D)-1 [3.8] | (S)-1 [6400] |
| Comparative Example 10 | (A)-2 [100] | (B2)-5 [19.8] | (D)-1 [3.8] | (S)-1 [6400] |
| Example 10 | (A)-2 [100] | (B1)-5 [23.2] | (D)-1 [3.8] | (S)-1 [6400] |

In Tables 1 and 2, the reference characters indicate the following. The values in brackets [ ] indicate the amount (in terms of parts by weight) of the component added.

(A)-1: Polymeric compound represented by chemical formula (A1)-1 shown below. Polymeric compound (A1)-1 was obtained by radical polymerization of monomers which derive the structural units constituting the polymeric compound, at a predetermined ratio. With respect to the polymeric compound (A1)-1, the weight average molecular weight (Mw) and the polydispersity (Mw/Mn) were determined by the polystyrene equivalent value as measured by gel permeation chromatography (GPC). As a result, it was found that the weight average molecular weight was 7,200, and the polydispersity was 1.69. The composition of the copolymer (ratio (molar ratio) of the respective structural units within the structural formula) as determined by $^{13}$C-NMR was l/m=50/50.

(A)-2: Polymeric compound represented by chemical formula (A1)-2 shown below. Polymeric compound (A1)-2 was obtained by radical polymerization of monomers which derive the structural units constituting the polymeric compound, at a predetermined ratio. With respect to the polymeric compound (A1)-2, the weight average molecular weight (Mw) and the polydispersity (Mw/Mn) were determined by the polystyrene equivalent value as measured by gel permeation chromatography (GPC). As a result, it was found that the weight average molecular weight was 6,900, and the polydispersity was 1.72. The composition of the copolymer (ratio (molar ratio) of the respective structural units within the structural formula) as determined by $^{13}$C-NMR was l/m/n=30/60/10.

[Chemical Formula 98.]

(A1)-1

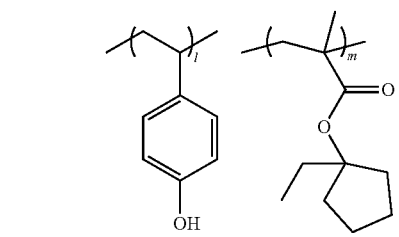

(A1)-2

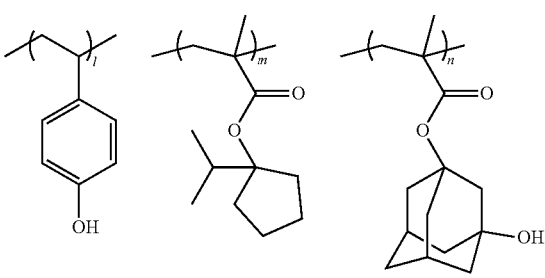

(B1)-1: Acid generator consisting of the compound (B1-1).
(B1)-2: Acid generator consisting of the compound (B1-2).
(B1)-3: Acid generator consisting of the compound (B1-3).
(B1)-4: Acid generator consisting of the compound (B1-4).
(B1)-5: Acid generator consisting of the compound (B1-5).
(B2)-1: Acid generator consisting of the compound (B2-1) shown below.
(B2)-2: Acid generator consisting of the compound (B2-2) shown below.
(B2)-3: Acid generator consisting of the compound (B2-3) shown below.
(B2)-4: Acid generator consisting of the compound (B2-4) shown below.
(B2)-5: Acid generator consisting of the compound (B2-5) shown below.
(D)-1: Acid diffusion control agent consisting of a compound represented by chemical formula (D1-1) shown below.
(S)-1: a mixed solvent of propylene glycol monomethyl ether acetate/propylene glycol monomethyl ether=60/40 (weight ratio).

[Chemical Formual 99.]

(B2-1)

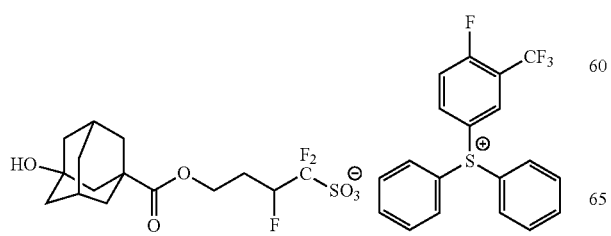

(B2-2)

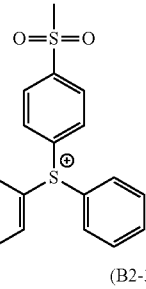

(B2-3)

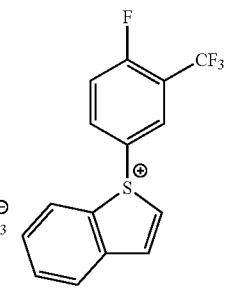

(B2-4)

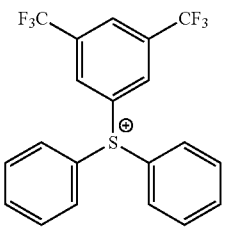

(B2-5)

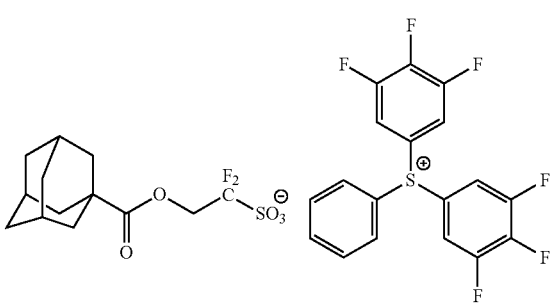

(D1-1)

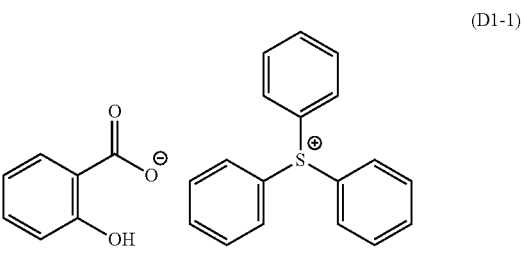

<Formation of Resist Pattern>

Each of the resist compositions of examples and comparative examples was applied to an 8-inch silicon substrate which had been treated with hexamethyldisilazane (HMDS) using a spinner, and was then prebaked (PAB) on a hot plate at 110° C. for 60 seconds and dried, thereby forming a resist film having a film thickness of 50 nm.

A drawing (exposure) was carried out on the resist film using an electron beam lithography system JEOL-JBX-9300FS (manufactured by JEOL Ltd.) with acceleration voltage of 100 kV and a target size of 1:1 line-and-space pattern (line width: 50 nm) (hereinafter referred to as an "LS pattern"). Then, a post exposure bake (PEB) treatment was conducted at 100° C. for 60 seconds.

Thereafter, alkali developing was conducted for 60 seconds at 23° C. in a 2.38% by weight aqueous solution of tetramethylammonium hydroxide (TMAH) (product name: NMD-3; manufactured by Tokyo Ohka Kogyo Co., Ltd.).

Then, water rinsing was conducted for 15 seconds using pure water.

As a result, a 1:1 LS pattern having a line width of 50 nm was formed.

[Evaluation of Optimum Exposure Dose (Eop)]

The optimum exposure dose Eop ($\mu C/cm^2$) with which the LS pattern was formed in the above formation of resist pattern was determined. The results are indicated under "Eop($\mu C/cm^2$)" in Tables 3 and 4.

[Evaluation of Line Width Roughness (LWR)]

With respect to the LS pattern formed in the above "formation of resist pattern", 3a was determined as a yardstick for indicating LWR. The results are indicated under "LWR (nm)" in Tables 3 and 4.

"3σ" indicates a value of 3 times the standard deviation (a) (i.e., 36) (unit: nm) determined by measuring the line positions at 400 points in the lengthwise direction of the line using a scanning electron microscope (product name: S-9380, manufactured by Hitachi High-Technologies Corporation; acceleration voltage: 800V).

The smaller this 3σ value is, the lower the level of roughness on the side walls of the line, indicating that an LS pattern with a uniform width was obtained.

TABLE 3

|  | Eop ($\mu C/cm^2$) | LWR (nm) |
| --- | --- | --- |
| Comparative Example 1 | 95 | 6.4 |
| Comparative Example 2 | 110 | 5.9 |
| Example 1 | 90 | 5.6 |
| Example 2 | 95 | 5.8 |
| Comparative Example 3 | 95 | 6.6 |
| Example 3 | 95 | 5.8 |
| Comparative Example 4 | 90 | 6.5 |
| Example 4 | 85 | 5.7 |
| Comparative Example 5 | 85 | 6.6 |
| Example 5 | 80 | 5.7 |

TABLE 4

|  | Eop ($\mu C/cm^2$) | LWR (nm) |
| --- | --- | --- |
| Comparative Example 6 | 100 | 6.3 |
| Comparative Example 7 | 115 | 5.8 |
| Example 6 | 95 | 5.5 |
| Example 7 | 95 | 5.7 |
| Comparative Example 8 | 100 | 6.3 |
| Example 8 | 95 | 5.6 |
| Comparative Example 9 | 90 | 6.4 |
| Example 9 | 90 | 5.5 |
| Comparative Example 10 | 90 | 6.5 |
| Example 10 | 85 | 5.4 |

As seen from the results shown in Tables 3 and 4, it was confirmed that, according to the resist compositions of Examples 1 to 10, sensitivity could be enhanced in the formation of a resist pattern, and a resist pattern having reduced roughness and a good shape could be formed.

What is claimed is:

1. A compound represented by general formula (bp-1) shown below:

(bp-1)

wherein $R^{p1}$ represents an aryl group which has a substituent containing a halogen atom and a substituent represented by the formula: —$SR^{p4}$; $R^{p2}$ and $R^{p3}$ represent an aryl group;

$R^{p1}$ represents an aryl group which has a substituent containing a halogen atom; $R^{p2}$ and $R^{p3}$ represent an alkyl group, and $R^{p2}$ and $R^{p3}$ are mutually bonded via a divalent group represented by the formula: —$SR^{p4'}$— to form a ring with the sulfur atom, $R^{p1}$ represents an aryl group which has a substituent containing a halogen atom and a substituent represented by the formula: —$SR^{p4}$; $R^{p2}$ represents an aryl group; and $R^{p3}$ represents an alkyl group, and $R^{p2}$ and $R^{p3}$ are mutually bonded to form a ring with the sulfur atom, $R^{p1}$ represents an aryl group which has a substituent containing a halogen atom; and $R^{p2}$ and $R^{p3}$ represent an aryl group which have a substituent represented by the formula: —$SR^{p4}$, or $R^{p1}$ and $R^{p2}$ represent an aryl group which have a substituent containing a halogen atom and a substituent represented by the formula: —$SR^{p4}$; and $R^{p3}$ represents an aryl group, $R^{p4}$ represents an alkyl group; $R^{p4'}$ represents an alkylene group or a single bond to form a ring; and $Xp^-$ represents a counteranion.

2. The compound according to claim 1, wherein $R^{p1}$ represents an aryl group which have a substituent containing a halogen atom and a substituent represented by the formula: —$SR^{p4}$; $R^{p2}$ and $R^{p3}$ represent an aryl group.

3. The compound according to claim 1, wherein $R^{p1}$ and $R^{p2}$ represent an aryl group which have a substituent containing a halogen atom and a substituent represented by the formula: —SR$^{p4}$; and R$^{p3}$ represents an aryl group.

4. The compound according to claim 1, wherein R$^{p1}$ represents an aryl group which has a substituent containing a halogen atom; R$^{p2}$ and R$^{p3}$ represent an alkyl group, and R$^{p2}$ and R$^{p3}$ are mutually bonded via a divalent group represented by the formula: —SR$^{p4}$- to form a ring with the sulfur atom.

5. The compound according to claim 1, wherein R$^{p1}$ represents an aryl group which has a substituent containing a halogen atom; and R$^{p2}$ and R$^{p3}$ represent an aryl group which has a substituent represented by the formula: —SR$^{p4}$.

6. The compound according to claim 1, wherein R$^{p1}$ represents an aryl group which has a substituent containing a halogen atom and a substituent represented by the formula: —SR$^{p4}$; R$^{p2}$ represents an aryl group; and R$^{p3}$ represents an alkyl group, and R$^{p2}$ and R$^{p3}$ are mutually bonded to form a ring with the sulfur atom.

7. The compound according to claim 1, wherein the substituent containing a halogen atom is a halogenated alkyl group.

8. The compound according to claim 2, wherein the substituent containing a halogen atom is a halogenated alkyl group.

9. The compound according to claim 3, wherein the substituent containing a halogen atom is a halogenated alkyl group.

10. The compound according to claim 4, wherein the substituent containing a halogen atom is a halogenated alkyl group.

11. The compound according to claim 5, wherein the substituent containing a halogen atom is a halogenated alkyl group.

12. The compound according to claim 6, wherein the substituent containing a halogen atom is a halogenated alkyl group.

13. The compound according to claim 1, wherein the Xp$^-$ represent an anion selected from the group consisting of a halogen anion, a carboxylic acid anion, and RpSO$_3^-$, and Rp is an alkyl group having 1 to 5 carbon atoms or a fluorinated alkyl group having 1 to 5 carbon atoms.

14. The compound according to claim 2, wherein the Xp$^-$ represents an anion selected from the group consisting of a halogen anion, a carboxylic acid anion, and RpSO$_3^-$, and Rp is an alkyl group having 1 to 5 carbon atoms or a fluorinated alkyl group having 1 to 5 carbon atoms.

15. The compound according to claim 3, wherein the Xp$^-$ represents an anion selected from the group consisting of a halogen anion, a carboxylic acid anion, and RpSO$_3^-$, and Rp is an alkyl group having 1 to 5 carbon atoms or a fluorinated alkyl group having 1 to 5 carbon atoms.

16. The compound according to claim 4, wherein the Xp$^-$ represents an anion selected from the group consisting of a halogen anion, a carboxylic acid anion, and RpSO$_3^-$, and Rp is an alkyl group having 1 to 5 carbon atoms or a fluorinated alkyl group having 1 to 5 carbon atoms.

17. The compound according to claim 5, wherein the Xp$^-$ represents an anion selected from the group consisting of a halogen anion, a carboxylic acid anion, and RpSO3$^-$, and Rp is an alkyl group having 1 to 5 carbon atoms or a fluorinated alkyl group having 1 to 5 carbon atoms.

18. The compound according to claim 6, wherein the Xp$^-$ represents an anion selected from the group consisting of a halogen anion, a carboxylic acid anion, and RpSO3$^-$, and Rp is an alkyl group having 1 to 5 carbon atoms or a fluorinated alkyl group having 1 to 5 carbon atoms.

\* \* \* \* \*